(12) United States Patent
Chiarle et al.

(10) Patent No.: US 11,530,253 B2
(45) Date of Patent: Dec. 20, 2022

(54) CUSTOMIZED CLASS SWITCH OF IMMUNOGLOBULIN GENES IN LYMPHOMA AND HYBRIDOMA BY CRISPR/CAS9 TECHNOLOGY

(71) Applicant: THE CHILDREN'S MEDICAL CENTER CORPORATION, Boston, MA (US)

(72) Inventors: Roberto Chiarle, Brookline, MA (US); Taek-Chin Cheong, Brighton, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 823 days.

(21) Appl. No.: 15/999,476

(22) PCT Filed: Feb. 23, 2017

(86) PCT No.: PCT/US2017/019097
§ 371 (c)(1),
(2) Date: Aug. 17, 2018

(87) PCT Pub. No.: WO2017/147278
PCT Pub. Date: Aug. 31, 2017

(65) Prior Publication Data
US 2021/0047386 A1 Feb. 18, 2021

Related U.S. Application Data

(60) Provisional application No. 62/299,864, filed on Feb. 25, 2016.

(51) Int. Cl.
| | | |
|---|---|---|
| C07K 16/00 | (2006.01) | |
| C12N 15/11 | (2006.01) | |
| C12N 9/22 | (2006.01) | |
| C12N 15/90 | (2006.01) | |

(52) U.S. Cl.
CPC ............... *C07K 16/00* (2013.01); *C12N 9/22* (2013.01); *C12N 15/11* (2013.01); *C12N 15/907* (2013.01); *C07K 2317/14* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 8,697,359 B1 | 4/2014 | Zhang | |
|---|---|---|---|
| 2005/0069921 A1* | 3/2005 | Roth | C12N 15/1082 435/6.1 |
| 2010/0076057 A1 | 3/2010 | Sontheimer et al. | |
| 2014/0017214 A1 | 1/2014 | Cost | |
| 2014/0356908 A1 | 12/2014 | Grosveld et al. | |
| 2016/0153006 A1* | 6/2016 | Zhang | C12N 15/907 424/93.7 |

FOREIGN PATENT DOCUMENTS

| CN | 103160515 A | 6/2013 |
|---|---|---|
| WO | 2010/075424 A2 | 7/2010 |
| WO | 2013/126794 A1 | 8/2013 |
| WO | 2013/142578 A1 | 9/2013 |
| WO | 2013/169398 A2 | 11/2013 |
| WO | 2013/176772 A1 | 11/2013 |
| WO | 2013/181440 A1 | 12/2013 |
| WO | 2014/011237 A1 | 1/2014 |
| WO | 2014/018423 A2 | 1/2014 |
| WO | 2014/022702 A2 | 2/2014 |
| WO | 2014/071219 A1 | 5/2014 |
| WO | 2014/204726 A9 | 12/2014 |
| WO | 2015/161276 A2 | 10/2015 |

OTHER PUBLICATIONS

Gostissa et al., IgH class switching exploits a general property of two DNA breaks to be joined in cis over long chromosomal distances (PNAS, 2014, 111:2644-2649) (Year: 2014).*
Dong et al., Orientation-Specific Joining of AID-initiated DNA Breaks Promotes Antibody Class Switching (Nature, 2015, 525:134-139) (Year: 2015).*
Cong et al., Multiplex genome engineering using CRISPR/Cas systems (Science, 2013, 339:819-823) (Year: 2013).*
Cheong et al., "Editing of mouse and human immunoglobulin genes by CRISPR-Cas9 system " Nature Communications 7(10934):1-10 (2016).
Dedeoglu et al., "Induction of activation-induced cytidine deaminase gene expression by IL-4 and CD40 ligation is dependent on STAT6 and NFKB." International Immunology 16(3):395-404 (2004).
Janeway et al. "Immunobiology: the immune system in health and disease." 5th Edition—Figure 4.20—Garland Science (2001).
Zheng et al., "Non-coding RNA generated following lariat debranching mediates targeting of AID to DNA." Cell 161 (4):762-773 (2015).

\* cited by examiner

*Primary Examiner* — Arthur S Leonard
(74) *Attorney, Agent, or Firm* — Nixon Peabody LLP; David S. Resnick; Jeanne Jodoin

(57) ABSTRACT

The present disclosure provides genetically modified antibody-producing cells comprising edited chromosomal sequences associated with immunoglobulin heavy chain constant region, the IgH locus. In particular, these cells are generated using a CRISPR/Cas 9-mediated editing process. The disclosure also provides specific guide RNA (gRNA) guide sequences that target the chromosomal sequence of immunoglobulin heavy chain constant region in the Switch regions.

16 Claims, 41 Drawing Sheets
Specification includes a Sequence Listing.

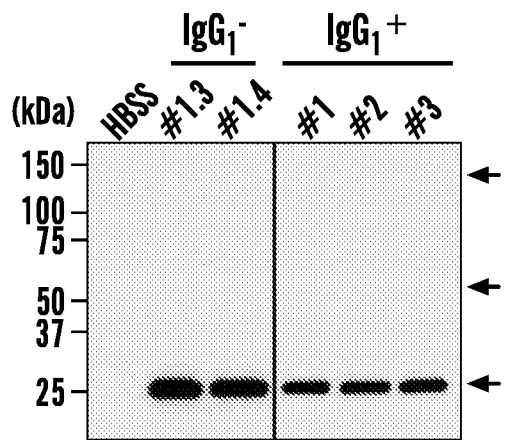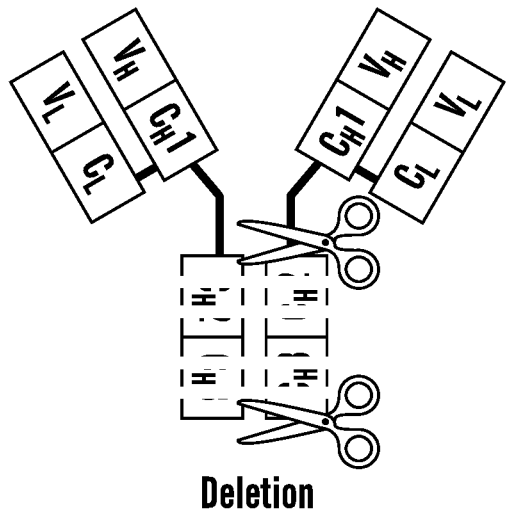
FIG. 18D
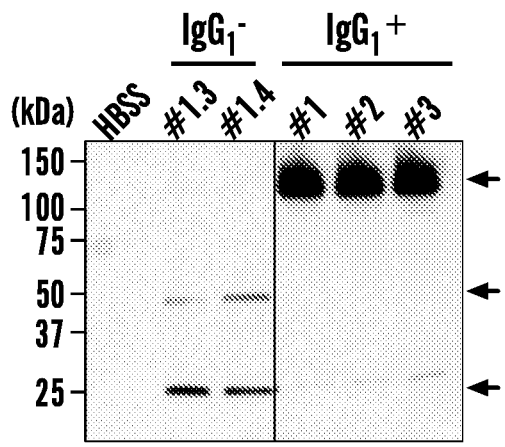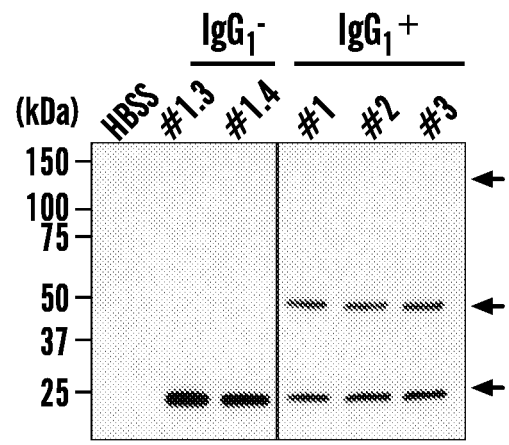
FIG. 18E
FIG. 18F

CUSTOMIZED CLASS SWITCH OF IMMUNOGLOBULIN GENES IN LYMPHOMA AND HYBRIDOMA BY CRISPR/CAS9 TECHNOLOGY

CROSS REFERENCE TO RELATED APPLICATION

This application is a 35 U.S.C. § 371 National Phase Entry Application of International Application No. PCT/US2017/019097 filed Feb. 23, 2017, which designates the U.S. and claims benefit under 35 U.S.C. § 119(e) of U.S. Provisional Application No. 62/299,864 filed Feb. 25, 2016, the contents of which are incorporated herein by reference in their entireties.

SEQUENCE LISTING

The instant application contains a Sequence Listing which has been submitted electronically in ASCII format and is hereby incorporated by reference in its entirety. The ASCII copy, created on Feb. 14, 2017, is named 701039-086381-PCT_SL.txt and is 103,859 bytes in size.

FIELD OF THE DISCLOSURE

This disclosure relates to class switch recombination (CSR) of the immunoglobulin (Ig) heavy chain genes mediated by targeted genomic editing.

BACKGROUND

Gene rearrangements editing the immunoglobulin (Ig) genes such as V(D)J recombination and class switch recombination (CSR) require the formation of DNA double strand breaks (DSBs) as the key initiating step. Under physiological conditions, DSBs are introduced at the Ig genes by the activity of B lymphocyte cell specific enzymes such as recombinase activating gene 1/2 (RAG1/2) and activation-induced cytidine deaminase, also known as AICDA and AID. During CSR, AID generates DSBs in the Ig locus by targeting repetitive sequences in the switch (S) regions that precede each Ig heavy (IgH) coding sequence. Paired DSBs in the switch regions are then joined by the classical and alternative non-homologous end joining (NHEJ) pathways to generate a switch of the IgH. This long range joining is thought to be part of a general mechanism of DNA repair where two DSBs are joined in cis over long chromosome distances. Efficient CSR can be obtained in absence of AID or S regions after the introduction of DSBs by site-specific I-SceI endonuclease.

Class switching occurs after the activation of a mature B cell via its membrane-bound antibody molecule (i.e., the cell surface B cell receptors) to generate the different classes of antibodies. Ligand or antigen binding to the cell surface B cell receptor triggers an intracellular cell signaling process that brings about CSR and produces the various classes of antibodies. The various classes of antibodies all have the same variable domains as the original antibody generated in the immature B cell during the process of V(D)J recombination, but possessing distinct constant domains in their heavy chains.

In the immature B cell's antibody immunoglobulin (Ig) heavy chain (IgH) locus, the order of arrangement of the nucleic acid sequence encoding the heavy chain segments (i.e., order of the heavy chain exons) are as follows: for human, they are μ (for IgM), δ (for IgD), γ3 (for IgG3), γ1 (for IgG1), α1 (for IgA1), γ2 (for IgG2), γ4 (for IgG4), ε (for IgE), and α2 (for IgA2); and for mouse, they are μ (for IgM), δ (for IgD), γ3 (for IgG3), γ1 (for IgG1), γ2b (for IgG2b), γ2a (for IgG2a), ε (for IgE), and γ (for IgA). Naive mature B cells produce both IgM and IgD, which are the first two heavy chain segments in the Ig locus. After activation by an antigen, these activated B cells proliferate. If these activated B cells encounter specific signaling molecules, e.g., via their CD40 and cytokine receptors, the cytokines are modulated by T helper cells, the activated B cells then undergo antibody class switching to produce IgG, IgA or IgE antibodies. Ligand or antigen binding to the cell surface B cell CD40 or cytokine receptor triggers an intracellular cell signaling process that brings about CSR. During class switching, the constant region of these activated B cells Ig heavy chain changes but the variable regions, and therefore antigenic specificity, stay the same. This allows different daughter cells from the same activated B cell to produce antibodies of different isotypes or subtypes (e.g. IgG1, IgG2 etc.). Thus, the activated B cell undergoes CSR and produces the various heavy chain classes of Ig antibodies that have target the antigen, i.e., have the same antigenic specificity.

In nature, cytokines are responsible for class switching. T cell cytokines that are responsible for class switching in mouse and humans are IL-4 and IL-5 produced by T helper 2 cells (Th2), IFN gamma (IFNγ) produced by T helper 1 cells (Th1), and TGFbeta (TGFβ) produced by T regulatory cells (Treg). In mouse, the cytokine IL-4 induces the class switching to IgG1 and IgA, IL-5 induces the class switching to IgG4, IFNγ induces the class switching to IgG2a and IgG3, and TGFβ induces the class switching to IgG2b and IgG4. In humans, the cytokine IL-4 induces the class switching to IgG1, IgG4 and IgE, IL-5 induces the class switching to IgA, IFNγ induces the class switching to IgG3, and TGFβ induces the class switching to IgA. These cytokines also may have suppressive effect on production of IgM and other subclasses that are not the induced class switched.

SUMMARY

The inventors have developed a new approach to effectuate class switch recombination (CSR) of the immunoglobulin (Ig) heavy chain genes (IgH) in vivo in mammalian cells that is (1) not dependent on any T cell cytokines, and (2) is not dependent on any intracellular B cell receptor signaling to initial the CSR therein. The new approach allows the antibody production of any class of one's choosing as desired and on demand. The new approach is based on a CRISPR/Cas9 system for targeted editing of the genome at the IgH chain locus to bring about CSR. Embodiments of the present disclosure are based on this new approach.

The new approach is an artificial means that does not depend on the activation of B cells, or the B cell membrane-bound antibody molecule (i.e., the B cell receptor), or intracellular signaling in the B cell triggered by the ligand binding of the cell-surface B cell receptor, or the T cell derived cytokines such IL-4, IL-5, IFNgamma, and TGFbeta in order to induce CSR. Applications of the CRISPR/Cas9 system to edit the genome have widely expanded to include DNA gene knock-out, deletions, chromosomal rearrangements, RNA editing and genome-wide screenings. Here, the inventors showed the application of CRISPR/Cas9 system bring about CSR in the immunoglobulin (Ig) locus of the heavy chain segment (IgH). The CRISPR/Cas9 technology was used to edit the mouse and human IgH genes in vivo and produced various Ig subclass antibodies by design and choice. By delivering a (1) Caspase 9 (Cas9) enzyme or similar enzyme and (2) specifically engineered guide RNAs (gRNAs) via vectors such as retrovirus or lentivirus into IgM+mouse B cells and hybridomas, the inventors were able to induce CSR of the IgH locus to produce to the IgH chain of the desired subclass. Similarly, the inventors induced CSR in all human B cell lines tested with high efficiency to targeted IgH subclass. Finally, the inventors engineered mouse hybridomas to secrete the Fab' fragment instead of the whole Ig using this new approach. The inventors showed that the IgH genes in mouse and human cells can be edited to obtain any desired IgH switching.

Accordingly, it is the objective of this disclosure to provide compositions, methods, and kits for inducing CSR in the IgH locus and thereby producing an antibody of a desired IgH subclass. The compositions, methods, and kits described herein do not depend on the activation of B cells, the B cell membrane-bound antibody molecule (i.e., the B cell receptor), or the T cell derived cytokines to induce CSR.

It is the objective of this disclosure to provide compositions methods, and kits for the rapid production of Fab or Fab' or F(ab')$_2$ fragments from a monoclonal antibody, more specifically, from a hybridomal clonal cell. The compositions and methods do not involve papain digestion. For example, the compositions and methods could transform a hybridoma that produces a whole Ig into a hybridoma producing only the Fab or Fab' or F(ab')$_2$ (that of course recognizes the same antigen) within one week.

Accordingly, in one embodiment, provided herein is a composition for directing CSR of an IgH chain locus in a mammalian cell to a desired IgH subclass, the composition comprising a vector comprising a nucleic acid encoding a Cas9 nuclease or nickase and nucleic acids encoding at least two gRNAs. The at least two gRNAs are non-identical, ie., they are distinct. The at least two gRNAs are engineered single strand RNA with a guide sequence at the 5'-end which is complementary to a target nucleic acid sequence on the IgH chain locus in the genome. This targeted approach provide the specificity.

In one embodiment, provided herein is a composition comprising a vector comprising a nucleic acid encoding a Cas9 nuclease or nickase and nucleic acids encoding at least two gRNAs for use in directing CSR of an IgH chain locus in a mammalian cell to a desired IgH subclass.

In another embodiment, provided herein is a composition comprising a first vector comprising a nucleic acid encoding a Cas9 nuclease or nickase, and a second vector comprising nucleic acids encoding at least two gRNAs, for use in directing CSR of an IgH chain locus in a mammalian cell to a desired IgH subclass, wherein the at least two gRNAs are distinct.

In yet another embodiment, provided herein is a composition comprising a first vector comprising a nucleic acid encoding a Cas9 nuclease or nickase, a second vector comprising a nucleic acids encoding a first gRNA, and a third vector comprising a nucleic acids encoding a second gRNA, for use in directing CSR of an IgH chain locus in a mammalian cell to a desired IgH subclass, wherein the first and second gRNAs are distinct.

In one embodiment, provided herein is a composition comprising a vector comprising a nucleic acid encoding a Cas9 nuclease or nickase and nucleic acids encoding a gRNA for use in a rapid method of production of a monoclonal antibody having a desired IgH subclass or producing a monoclonal Fab or Fab' or F(ab')$_2$ fragment.

In another embodiment, provided herein is a composition comprising a first vector comprising a nucleic acid encoding a Cas9 nuclease or nickase, and a second vector comprising nucleic acids encoding a gRNA for use in a rapid method of production of a monoclonal antibody having a desired IgH subclass or producing a monoclonal Fab or Fab' or F(ab')$_2$ fragment.

In one embodiment, provided herein is a composition comprising at least three coding nucleic acids, one nucleic acid encoding a Cas9 nuclease or nickase, a second nucleic acid encoding a first gRNA, and a third nucleic acid encoding a second gRNA, wherein the first and second gRNAs are distinct. This composition is useful for directing CSR of an IgH chain locus in a mammalian cell to a desired IgH subclass.

In one embodiment, provided herein is a composition comprising at least two coding nucleic acids, one nucleic acid encoding a Cas9 nuclease or nickase, and a second nucleic acid encoding a gRNA. This composition is useful for rapid production of a monoclonal antibody having a desired IgH subclass from a hybridoma clonal cell or for the production of a monoclonal Fab or Fab' or F(ab')$_2$ fragment from a hybridoma clonal cell.

In one embodiment, provided herein is a kit for directing CSR of an IgH chain locus in a mammalian cell to a desired IgH subclass, the kit comprising a vector comprising a nucleic acid encoding a Cas9 nuclease or nickase and nucleic acids encoding at least two gRNAs, at least two gRNAs are non-identical, ie., they are distinct, and they are designed to target a S region in an IgH chain locus in a mammalian cell, with each gRNA targeting a different S region in the IgH locus.

In one embodiment, provided herein is a kit for directing CSR of an IgH chain locus in a mammalian cell to a desired IgH subclass, the kit comprising a first vector comprising a nucleic acid encoding a Cas9 nuclease or nickase, and a second vector comprising nucleic acids encoding at least two gRNAs, wherein the first and second gRNAs are distinct.

In one embodiment, provided herein is a kit for directing CSR of an IgH chain locus in a mammalian cell to a desired IgH subclass, the kit comprising a first vector comprising a nucleic acid encoding a Cas9 nuclease or nickase, a second vector comprising a nucleic acids encoding a first gRNA, and a third vector comprising a nucleic acids encoding a second gRNA, wherein the first and second gRNAs are distinct.

In one embodiment, provided herein is a kit for directing CSR of an IgH chain locus in a mammalian cell to a desired IgH subclass, the kit comprising a nucleic acid encoding a Cas9 nuclease or nickase and nucleic acids encoding at least two gRNAs, at least two gRNAs are non-identical, ie., they are distinct, and they are designed to target a S region in an IgH chain locus in a mammalian cell, with each gRNA targeting a different S region in the IgH locus.

In one embodiment, provided herein is a kit for directing CSR of an IgH chain locus in a mammalian cell to a desired IgH subclass, the kit comprising at least three coding nucleic acids, one nucleic acid encoding a Cas9 nuclease or nickase, a second nucleic acid encoding a first gRNA, and a third nucleic acid encoding a second gRNA, wherein the first and second gRNAs are distinct.

In one embodiment, provided herein is a kit for the use in rapid method of production of monoclonal antibody of a desired IgH subclass or producing a monoclonal Fab or Fab' or F(ab')$_2$ fragment, the kit comprising a nucleic acid encoding a Cas9 nuclease or nickase and a nucleic acid encoding a gRNA, wherein the gRNA targets the papain or pepsin cleavage site of the Fc region on the antibody.

In one embodiment, provided herein is a kit for the use in rapid method of production of monoclonal antibody of a desired IgH subclass or producing a monoclonal Fab or Fab' or F(ab')$_2$ fragment, the kit comprising a nucleic acid encoding a Cas9 nuclease or nickase and a nucleic acid encoding a gRNA selected from the sequences in Table 1.

In one embodiment, provided herein is a kit for the use in rapid method of production of monoclonal antibody of a desired IgH subclass or producing a monoclonal Fab or Fab' or F(ab')$_2$ fragment, the kit comprising a vector comprising a nucleic acid encoding a Cas9 nuclease or nickase and a nucleic acid encoding a gRNA, wherein the gRNA targets the papain or pepsin cleavage site of the Fc region on the antibody.

In one embodiment, provided herein is a kit for the use in rapid method of production of monoclonal antibody of a desired IgH subclass or producing a monoclonal Fab or Fab' or F(ab')$_2$ fragment, the kit comprising a first vector comprising a nucleic acid encoding a Cas9 nuclease or nickase, and a second vector comprising nucleic acids encoding a gRNA, wherein the gRNA targets the papain or pepsin cleavage site of the Fc region on the antibody.

In one embodiment, provided herein is a method for directing CSR of an IgH chain locus in a mammalian cell to a desired IgH subclass comprising contacting the mammalian cell with a composition described herein, for example, a composition comprising a vector or vectors described herein or a composition comprising nucleic acids described herein.

In one embodiment, provided herein is a method for directing CSR of an IgH chain locus in a mammalian cell to a desired IgH subclass comprising contacting the mammalian cell with a vector or vectors comprising a nucleic acid encoding a Cas9 nuclease or nickase and nucleic acids encoding at least two gRNAs described herein, or contacting with a composition comprising the vector (s), or contacting with a composition comprising a nucleic acid encoding a Cas9 nuclease or nickase and nucleic acids encoding at least two gRNAs described herein, whereinat least two gRNAs are non-identical, ie., they are distinct, and they are designed to target a S region in an IgH chain locus in a mammalian cell, with each gRNA targeting a different S region in the IgH locus.

In one embodiment, provided herein is a rapid method of producing monoclonal antibody of a desired IgH subclass or producing a monoclonal Fab or Fab' or F(ab')$_2$ fragment, the method comprising providing a hybridoma clonal cell and contacting the hybridoma clonal cell with a vector or vector(s) comprising a nucleic acid encoding a Cas9 nuclease or nickase and nucleic acids encoding a gRNA described herein, or a composition comprising a vector comprising a nucleic acid encoding a Cas9 nuclease or nickase and nucleic acids encoding a gRNA described herein or with a composition comprising a nucleic acid encoding a Cas9 nuclease or nickase and a nucleic acid encoding a gRNA described herein, wherein the gRNA targets the papain or pepsin cleavage site of the Fc region on the antibody.

In one embodiment, provided herein is a mammalian cell comprising a vector or vectors comprising an exogenous nucleic acid encoding a Cas9 nuclease or nickase and exogenous nucleic acids encoding at least two gRNAs, wherein the at least two gRNAs are distinct.

In one embodiment, provided herein is a mammalian cell comprising an exogenous nucleic acid encoding a Cas9 nuclease or nickase and exogenous nucleic acids encoding at least two gRNAs, wherein the at least two gRNAs are distinct.

In one embodiment, provided herein is a composition comprising a population of mammalian cells comprising a vector or vectors comprising an exogenous nucleic acid encoding a Cas9 nuclease or nickase and exogenous nucleic acids encoding at least two gRNAs, wherein the at least two gRNAs are distinct.

In one embodiment, provided herein is a composition comprising a population of mammalian cells comprising an exogenous nucleic acid encoding a Cas9 nuclease or nickase and exogenous nucleic acids encoding at least two gRNAs, wherein the at least two gRNAs are distinct.

In one embodiment, provided herein is a mammalian hybridoma clonal cell comprising a vector or vectors comprising an exogenous nucleic acid encoding a Cas9 nuclease or nickase and an exogenous nucleic acid encoding a gRNA, wherein the gRNA targets the papain or pepsin cleavage site of the Fc region on the antibody.

In one embodiment, provided herein is a mammalian hybridoma clonal cell comprising an exogenous nucleic acid encoding a Cas9 nuclease or nickase and an exogenous nucleic acid encoding a gRNA, wherein the gRNA targets the papain or pepsin cleavage site of the Fc region on the antibody.

In one embodiment, provided herein is a composition comprising a population of mammalian hybridoma clonal cells comprising a vector or vectors comprising an exogenous nucleic acid encoding a Cas9 nuclease or nickase and an exogenous nucleic acid encoding a gRNA, wherein the gRNA targets the papain or pepsin cleavage site of the Fc region on the antibody.

In one embodiment, provided herein is a composition comprising a population of mammalian hybridoma clonal cells comprising comprising an exogenous nucleic acid encoding a Cas9 nuclease or nickase and a nucleic acid encoding a gRNA, wherein the gRNA targets the papain or pepsin cleavage site of the Fc region on the antibody.

In one embodiment of any composition, method, or kit described, the vector is a polycistronic vector comprising at least three coding nucleic acid sequences, wherein one nucleic acid encoding a Cas9 nuclease or nickase, a second nucleic acid encoding a first gRNA, and a third nucleic acid encoding a second gRNA, wherein the first and second gRNAs are distinct, and they are designed to target a S region in an IgH chain locus in a mammalian cell, with each gRNA targeting a different S region in the IgH locus. For example, the vector described herein is a tri-cistronic vector.

In one embodiment of any composition, method, or kit described, the vector is a mono-cistronic vector consisting essentially of a coding nucleic acid, wherein the nucleic acid encodes either a Cas9 nuclease or nickase, or a gRNA, wherein the gRNA target a S region in an IgH chain locus in a mammalian cell or targets the papain or pepsin cleavage site of the Fc region on the antibody in a mammalian cell.

In one embodiment of any composition, method, or kit described, the vector is a dicistronic vector comprising a nucleic acid encoding a Cas9 nuclease or nickase and a nucleic acid encoding a gRNA, wherein the gRNA targets the papain or pepsin cleavage site of the Fc region on the antibody.

In one embodiment of any composition, method, or kit described, the vector or vectors described expresses the Cas9 nuclease or nickase and the gRNA described in vivo in the mammalian cell.

In one embodiment of any composition, method, or kit described, the vector described herein is a viral vector. For example, a lentivirus, a retrovirus, an adenovirus, or an adeno-associated virus that are known in the art for transfections of nucleic acids into mammalian cells.

In one embodiment of any composition, method or kit described herein for the directing CSR of an IgH chain locus in a mammalian cell to a desired IgH subclass, at least two gRNAs are non-identical, ie., they are distinct, and they are designed to target a S region in an IgH chain locus in a mammalian cell, with each gRNA targeting a different S region in the IgH locus.

In one embodiment of any composition, method, or kit described, the gRNA is an engineered single strand RNA with a guide sequence at the 5'-end which is complementary to a targeted nucleic acid sequence on the IgH chain locus in the genome.

In one embodiment of any composition, method, or kit described, the targeted nucleic acid sequence on the IgH chain locus is an S region in the IgH chain locus in a mammalian cell.

In one embodiment of any composition, method, or kit described, the targeted nucleic acid sequence on the IgH chain locus is the papain or pepsin cleavage site of the Fc region on the antibody in a mammalian cell.

In one embodiment of any composition, method, or kit described, the gRNA comprises a gRNA guide sequence.

In one embodiment of any composition, method, or kit described, the gRNA guide sequence comprises a seed sequence.

In one embodiment of any composition, method, or kit described, the guide sequence is located at the the 5'-end of the gRNA.

In one embodiment of any composition, method, or kit described, the seed sequence is located at the the 5'-end of the gRNA.

In one embodiment of any composition, method, or kit described, the guide sequence is complementary to a targeted nucleic acid sequence on the IgH chain locus in the genome.

In one embodiment of any composition, method, or kit described, the seed sequence is complementary to a targeted nucleic acid sequence on the IgH chain locus in the genome.

In one embodiment of any composition, method, or kit described, the gRNA comprises a gRNA guide sequence and a Cas recognition sequence (tracrRNA). The tracrRNA is for the binding of the Cas9 nuclease or nickase which in turn is brought the targeted S region of the IgH locus by the gRNA guide sequence.

In one embodiment of any composition, method, or kit described, the gRNA consists of a gRNA guide sequence and a tracrRNA sequence.

In one embodiment of any composition, method, or kit described, the gRNA consists essentially of a gRNA guide sequence and a tracrRNA.

In one embodiment of any composition, method, or kit described, the gRNA guide sequence described herein comprises a seed region or seed sequence consisting of at least 10 consecutive nucleotides of a target sequence in a IgH gene locus present in the mammalian cell wherein the target sequence of the gRNA is contiguous to a protospacer adjacent motif (PAM) in the IgH locus.

In one embodiment of any composition, method, or kit described, the gRNA guide sequence or seed sequence described herein is from about 10 nucleotides to more than about 25 nucleotides. For example, the region of base pairing between the guide sequence and the corresponding target site sequence can be about 10, 11, 12, 13, 14, 15, 16, 17, 18, 19, 20, 22, 23, 24, 25, or more than 25 nucleotides in length. In an exemplary embodiment, the guide sequence is about 17-20 nucleotides in length, such as 20 nucleotides.

In one embodiment of any composition, method, or kit described, the seed region or seed sequence of a gRNA guide sequence is selected from the sequence disclosed in Table 1, 4, and 5.

In one embodiment of any composition, method, or kit described, the gRNA guide sequence or seed sequence described herein is complementary to the guide sequence selected from the sequence disclosed in Table 1, 4, and 5, and does not contain the PAM.

In one embodiment of any composition, method, or kit described, the gRNA guide sequence or seed sequence described herein comprises the guide sequence selected from the sequence disclosed in Table 1, 4, and 5, and does not contain the PAM.

In one embodiment of any composition, method, or kit described, the gRNA guide sequence or seed sequence described herein comprises the guide sequence selected from the sequence disclosed in Table 1, 4, and 5, and contains the PAM.

In one embodiment of any composition, method, or kit described, the gRNA guide sequence or seed sequence described herein consists of the guide sequence selected from the sequence disclosed in Table 1, 4, and 5, and does not contain the PAM.

In one embodiment of any composition, method, or kit described, the gRNA guide sequence or seed sequence described herein consists of the guide sequence selected from the sequence disclosed in Table 1, 4, and 5, and contains the PAM.

In one embodiment of any composition, method, or kit described, the gRNA guide sequence or seed sequence described herein consists essentially of the guide sequence selected from the sequence disclosed in Table 1, 4, and 5, and does not contain the PAM.

In one embodiment of any composition, method, or kit described, the gRNA guide sequence or seed sequence described herein consists essentially of the guide sequence selected from the sequence disclosed in Table 1, 4, and 5, and contains the PAM.

In one embodiment of any composition, method, or kit described, the PAM is recognized by a ribonucleoprotein complex comprising a Cas9 nuclease or nickase.

In one embodiment of any composition, method, or kit described, the PAM motif that is contiguous with the gRNA guide sequence is located at the 3'-end of the gRNA.

In one embodiment of any composition, method, or kit described, the PAM motif that is contiguous with the gRNA guide sequence is located at the 3'-end of the target sequence.

In one embodiment of any composition, method, or kit described, the PAM motif that is contiguous with the gRNA guide sequence is a three nucleotide motif, -NGG-, wherein N is any nucleotide, (A, T, G, or C; adenine=A, cytosine=C, guanine=G, thymine=T) and G is guanine.

In one embodiment of any composition, method, or kit described, the target sequence for the gRNA guide sequence is within a switch (S) region which is upstream from a gene segment/nucleic acid sequence that encode a subclass constant region of an antibody heavy chain in the IgH locus. See FIGS. 5A and 15A.

In one embodiment of any composition, method, or kit described, the target sequence for the gRNA guide sequence is located at the 5'-end of the targeted S region in the IgH locus. See FIGS. 1A and 2A.

In another embodiment of any composition or method described, the target sequence for the gRNA guide sequence is located at the 3'-end of the targeted S region in the IgH locus. See FIGS. 1A and 2A.

In one embodiment of any composition, method, or kit described, the at least two gRNAs guide sequences targeted different S regions in the IgH locus to bring about CSR (see FIGS. 1A, 2A, 7A, 7B, 11, and 12A, and Tables 1 and 4).

In one embodiment of any composition, method, or kit described, the target sequence for the gRNA guide sequence flanks an S region of an IgH locus, either the 5'-end or the 3-end of the S region.

In one embodiment of any composition, method, or kit described, the target sequence for the gRNA guide sequence flanks a gene segment/nucleic acid sequence that encode a constant region of an antibody heavy chain (as known as an exon constant region gene segment in the IgH locus).

In one embodiment of any composition, method, or kit described, the exon constant region gene segment in the IgH locus is selected from the group consisting of mu ($\mu$, delta ($\delta$), gamma ($\gamma$), alpha ($\alpha$), or epsilon ($\epsilon$).

In one embodiment of any composition, method, or kit described, the exon constant region gene segment in the IgH locus is selected from the group consisting of $\mu$ (for IgM), $\delta$ (for IgD), $\gamma3$ (for IgG3), $\gamma1$ (for IgG1), $\alpha1$ (for IgA1), $\gamma2$ (for IgG2), $\gamma4$ (for IgG4), $\epsilon$ (for IgE), and $\alpha2$ (for IgA2).

In one embodiment of any composition, method, or kit described, the exon constant region gene segment in the IgH locus is selected from the group consisting of $\mu$ (for IgM), $\delta$ (for IgD), $\gamma3$ (for IgG3), $\gamma1$ (for IgG1), $\gamma2b$ (for IgG2b), $\gamma2a$ (for IgG2a), $\epsilon$ (for IgE), and $\alpha$ (for IgA).

In one embodiment of any composition, method, or kit described, the gRNA comprises a gRNA guide sequence that comprises a seed sequence selected from Tables 1, 4 and 5.

In one embodiment of any composition, method, or kit described, the desired IgH subclass is selected from the group consisting of IgA1, IgA2, IgM, IgE, IgD, IgG1, IgG2, and IgG3 and IgG4.

In one embodiment of any composition, method, or kit described, the desired IgH subclass is selected from the group consisting of IgA, IgM, IgE, IgD, IgG1, IgG2a, IgG2b, and IgG3.

In one embodiment of any composition or method described, the mammalian cell is a B lymphocyte or a hybridoma cell.

In one embodiment of any composition or method described, the B lymphocyte is a naïve or activated B lymphocyte.

In one embodiment of any composition or method described, the mammalian cell is a human, mouse, rat, donkey, monkey, pig, horse, hamster, or guinea pig cell.

In one embodiment of any composition or method described, the B lymphocyte is derived from a mouse, a rat, a human, a donkey, a monkey, a pig, a horse, a hamster, or a guinea pig.

In one embodiment of any composition, method, or kit described, the gRNAs targeting the DNA proximal to the papain cleavage site of the IgG1 coding sequence.

In one embodiment of any composition or method described, the gRNAs' guide sequences are GATGCAACAAGTGGCCATGT (SEQ ID NO: 1) and TGTGCTCTTCCTATGCAAAC (SEQ ID NO: 2).

In one embodiment of any composition, method, or kit described, the Cas9 nuclease or nickase is a hSpCas9 nuclease, a hSaCas9 nuclease, a hSpCas9 nickase, a hSa-Cas9 nickase or a dCas9-Fold nuclease.

In one embodiment of any composition, method, or kit described, the Cas9 nuclease or nickase is modified such that the protein is human-codon optimized.

BRIEF DESCRIPTION OF THE DRAWINGS

FIG. 1B. An example chromatogram showing a perfect spliced S$\mu$ 5' and S$\gamma$1 3' genomic junction, as well as representative sequences of spliced junctions identified from 30 clones obtained in the CRISPR/Cas9 mediated CSR. Ref. Seq. in the sequence of the predicted genomic junction between S$\mu$ 5' and S$\gamma$1 3' regions. Bold sequence represent downstream sequence of the S$\gamma$1 3' region. Non-bold, regular sequence represent upstream sequence of the S$\mu$ 5' region. Underlined bases are base insertions created during the CSR; Dashes are the deleted bases during the CSR. Figure discloses SEQ ID NOS 400, 400-402, 402-407, respectively, in order of appearance.

FIG. 1C. Mouse B cells isolated from the spleen of 129S2 WT and AID-deficient mice were activated by anti-CD40 antibody and IL-4 for 1 day and then transduced with retrovirus expressing Cas9 nuclease and gRNAs used in (FIG. 1A). Empty GFP- or AID-expressing retroviruses were used as negative or positive controls, respectively. At day 4, cells were harvested, stained with IgG1 antibody, and then analyzed by flow cytometry. IgG1+ cells were gated on GFP positive population. Mean±SD; n=3 in each experimental condition. $P<0.01$; *$P<0.001$.

FIGS. 1D-1E. IgM+ hybridomas were transduced with four different combinations of lentiviruses expressing Cas9 nuclease and gRNAs as above. Representative zebra plots (FIG. 1D) and average percentages±SD of CSR (FIG. 1E) from six independent experiments are presented.

FIG. 2A. Top: Genomic organization of the human IgH constant region locus and position of the gRNAs. Bottom: Schematic representation of six possible CSR products induced by deletions between S$\mu$ and S$\gamma$3, S$\gamma$1, or S$\alpha$1 regions. Black arrows on the bottom schematic representation indicate the positions for the PCR primers designed to detect deletion. Gels show PCR amplicons obtained with the indicated primers.

FIG. 2B. Representative sequences of junctions identified from 30 clones for S$\mu$ 3' and S$\gamma$1 3' genomic region. Ref. Seq. is the sequence of the predicted genomic junction between S$\mu$ 3' and S$\gamma$1 3' region, bold sequence represent downstream sequence of the S$\gamma$1 3' region, and non-bold regular sequence represent upstream sequence of the S$\mu$ 3' region. Dashes are the deleted bases during the CSR. Figure discloses SEQ ID NOS 408 and 408-417, respectively, in order of appearance.

FIG. 2C. IgM+JEKO-1 cells were transduced with lentiviruses expressing Cas9 nuclease and gRNAs targeting S$\mu$ and S$\gamma$3, S$\gamma$1, or S$\alpha$1 flanking regions. Cells were collected, co-stained with antibodies against CD19 and IgG or IgA, and analyzed by flow cytometry. Representative zebra plots from three independent experiments are presented. Percentages of events are indicated in the corresponding quadrants.

FIG. 2D. To induce sequential CSR from IgM to IgG and then to IgA, IgM+JEKO-1 cells were transduced with lentiviruses expressing Cas9 nuclease and gRNAs targeting Sµ 3' and Sγ3 3' flanking regions to generate IgG3+ JEKO-1 cells. IgG3+ cells were transduced again with lentiviruses expressing Cas9 nuclease and gRNAs targeting Sµ 5' and Sα1 3' flanking regions. Four days later, cells were collected, co-stained with IgM, IgG, or IgA antibodies, and analyzed by flow cytometry. Representative zebra plots from three independent experiments are presented. Percentages of events are indicated in the corresponding quadrants.

FIGS. 4A-4C. To understand the growth of B cells after switch of the IgH subclass, JEKO-1 cells were co-transduced with two lentiviruses expressing Cas9 nuclease and gRNAs targeting Sµ, Sγ3 3' (FIG. 4A), Sµ, Sγ1 3' (FIG. 4B), and Sµ, Sα1 3' (FIG. 4C) flanking regions. Cells were co-stained with antibodies against IgM and IgG or IgA and analyzed by flow cytometry over time.

FIG. 4D. Statistical analysis of relative growth rates from in FIGS. 4A-4C. Data are from at least four experiments in each condition. P<0.01; *P<0.001.

FIG. 4E. JEKO-1 cells were transduced with lentiviruses expressing Cas9 nuclease and gRNAs targeting Sµ and Sγ3 regions. After 5 days, cells were transduced with retroviral vector expressing GFP as reporter and PI3KδE1021K or GFP alone (control). Cells were co-stained with antibodies against IgM and IgG to allow the gating on the IgH-negative population and analyzed by flow cytometry. After gating on the IgM-/IgG- (IgH-) population, percentages of GFP positive cells were calculated over time. Data were analyzed by FlowJo software. Mean±SD; n=3. ***P<0.001.

FIG. 5A. Top: schematic representation of mouse IgG antibody and target sites of two different gRNAs used for Fab' fragment production. By using lentiviruses expressing Cas9 nuclease and Fc 5' or Fc 5'/Fc 3' guide RNAs, Fab' fragments were produced by frameshift (left) or deletion (right) of the IgH Fc fragment, respectively. Bottom: schematic depiction of 5' gRNA (scissors) in reference to the papain cleavage site. PAM sequence is underlined in Fc 5' gRNA. Figure discloses SEQ ID NOS 436-438 and 418, respectively, in order of appearance.

FIG. 5B. IgG1+ hybridomas were transduced with lentivirus expressing Cas9 nuclease and gRNAs targeting Fc 5' or Fc 5' and Fc3' regions. gRNAs targeting Sµ 5', Sγ1 3' or Fc 3' were used as negative controls. Hybridomas were selected with puromycin, stained with IgM and IgG1 antibodies, and analyzed by flow cytometry. Representative zebra plots from three different IgG1+ hybridomas are presented. Percentages of events are indicated in the corresponding quadrants.

FIG. 5C. Histograms representing the percentages of IgG-negative cells are shown with mean±SD; n=3 hybridomas for each condition. ***P<0.001.

FIGS. 5D-5E. Western blot analyses of Fab' fragments from hybridoma supernatants. IgG1+ hybridomas were transduced with lentiviruses expressing Cas9 nuclease and gRNAs targeting Fc 5' or Fc 5' and Fc3' regions and IgG1-negative single clones were obtained by serial dilution. Examples of two clones from the frameshift approach (FIG. 5D; #1.1 and #1.2; purity>99%) and two clones from the deletion approach (FIG. 5E; #1.3 and #1.4; purity>99%) are shown. Supernatants were loaded on a SDS-PAGE in non-reducing condition, and developed with an anti-mouse kappa light chain antibody. Three different IgG1+hybridomas were used as controls.

FIG. 6A. Schematic overview of lentiCRISPR v2 vector (ADDGENE #52961).

FIG. 6B. Evaluation of the efficiency of gRNAs targeting in mouse fibroblast cells. Locus modification efficiencies were analyzed 5 days after transduction using Surveyor nuclease assay. Estimated indel formation is indicated below each target. Open white arrowheads indicate expected bands. N.D.: not detected.

FIG. 7A. Top: Schematic overview of an example of inversion between Sµ 5' and Sγ1 3'. Black little arrows indicate the primers for PCR. Cutting sites are indicated by scissors. Bottom: Detection of deletions by PCR on genomic DNA extracted from mouse fibroblast transduced with two lentiviruses expressing Cas9 nuclease and gRNAs targeting Sµ and Sγ1 flanking regions. Mouse fibroblast cells were transduced with lentiviruses, selected with puromycin (6 µg/ml), and collected at day 7 to isolate genomic DNA.

FIG. 7B. Top: Schematic overview of an example of excision circle between Sµ 5' and Sγ1 3'. Black little arrows indicate primers for PCR. Cutting sites are indicated by scissors. Bottom: Detection of excision circles by PCR on genomic DNA extracted from mouse fibroblast transduced with two lentiviruses expressing Cas9 nuclease and gRNAs targeting Sµ and Sγ1 flanking regions. Mouse fibroblast cells were transduced with lentiviruses, selected with puromycin (6 µg/ml), and collected at day 7 to isolate genomic DNA.

FIG. 8A. Schematic overview of RetroCRISPR v2 vector.

FIG. 8B. Schematic overview of RetroCRISPR v2 vector. pMSCVgfp::AID vector (ADDGENE #15925) was cut to obtain retroviral backbone and ligated with the segment from U6 promoter to puromycin isolated from LentiCRISPR v2 (FIG. 6A). GFP was amplified by PCR with primers, and replaced with puromycin in the vector.

FIGS. 8C-8D. Untouched mouse B cells isolated from the spleen of 129S2 WT (FIG. 8C) and AID-deficient (FIG. 8D) mice were activated by CD40 antibody and IL-4 for 1 day and then transduced with retrovirus expressing Cas9 nuclease and gRNAs used in (FIG. 8B). GFP expressing-retrovirus or AID expressing-retrovirus was used as negative or positive control, respectively. Three days later, cells were harvested, stained with IgG1 antibody, and then analyzed by flow cytometry. IgG1+ cells were gated on the GFP positive population. Representative zebra plots are presented and percentages of events are indicated in the corresponding quadrant.

FIG. 12A. Schematic overview of an example of an inversion resulting from gRNA targeting Sµ 5' and Sγ3 3' flanking regions. Black little arrows indicate primers for PCR. Cutting sites are indicated with scissors.

FIG. 12B. Detection of excised circle by PCR on genomic DNA extracted from JEKO-1 cells transduced with two lentiviruses expressing Cas9 nuclease and gRNAs targeting Sµ and Sγ3 or Sγ1 flanking regions.

FIG. 15A. Schematic overview of the PCR approach to distinguish between frameshift or deletion mediated removal of IgH Fc portion in single cell clones obtained from IgH negative hybridomas. Black little arrow indicates the primers for Fc 5' forward primer, the Fc 5' reverse primer and the Fc 3' reverse primer, respectively. The circle represents IgH hinge region.

FIG. 15B. Gels of PCR reactions were performed with the indicated primer sets. Four (#36, #37, #48 and #53) out of 64 clones showed deletion of the IgH Fc portion.

FIG. 16A. Examples of Sanger sequencing of the junctions of the Fc 5' region with frameshift mediated removal of the IgH Fc portion in Fab' hybridomas clones #1, #5, #10, and #12. Ref. Seq. is sequence of the predicted genomic junction of Fc 5' region. Black downward pointing arrow indicates the Cas9 cutting site. PAM sequence is underlined or boxed. Figure discloses SEQ ID NOS 428, 429, 428, 430, 428, and 431, respectively, in order of appearance.

FIG. 16B. Examples of Sanger sequencing of junctions of the Fc 5' region with deletion mediated removal of the IgH Fc portion in Fab' hybridomas clones #36, #37, #48 and #53, deletion mediated removal by way of the described Cas9/gRNA deletion. Ref. Seq. is the sequence of the predicted genomic spliced junction between Fc 5' and Fc3' regions. Bold sequence represent downstream sequence of the Fc 3' region. Non-bold sequence represent upstream sequence of the Fc 5' region. Figure discloses SEQ ID NOS 432, 433, 432, 434, 432, and 435, respectively, in order of appearance.

FIGS. 18A-18F. Detection of Fab' fragments in the supernatants of hybridomas. Western blot analyses of supernatants collected from hybridomas. IgG1-expressing hybridomas were transduced with lentiviruses expressing Cas9 nuclease and gRNAs targeting Fc 5' (frameshift) or Fc 5' and Fc 3' together (deletion). Two days later, cells were treated with puromycin (3 µg/ml) to select IgG1-negative hybridomas. Two clones from the frameshift approach (#1.1 and 1.2) and 2 clones from deletion approach (#1.3 and #1.4) as in FIG. 17 were isolated and cultured in HBSS for 1 day. Supernatants were collected, loaded on the 4-15% gradient SDS-PAGE with reducing agent (β-mercaptoethanol; FIGS. 18A, 18C, 18D, and 18F) or in non-reducing conditions (FIGS. 18B and 18E) and developed with an anti-mouse kappa light chain antibody (FIGS. 18A and 18D) or an anti-mouse IgG H&L antibody (FIGS. 18B, 18C, 18E, and 18F). 25 kDa band: kappa light chain; 50 kDa band: Fab' fragments in FIGS. 18B and 18E or IgG1 heavy chain in FIGS. 18A, 18C, 18D and 18F; 150 kDa band: whole IgG1.

DETAILED DESCRIPTION

Figure 1A:
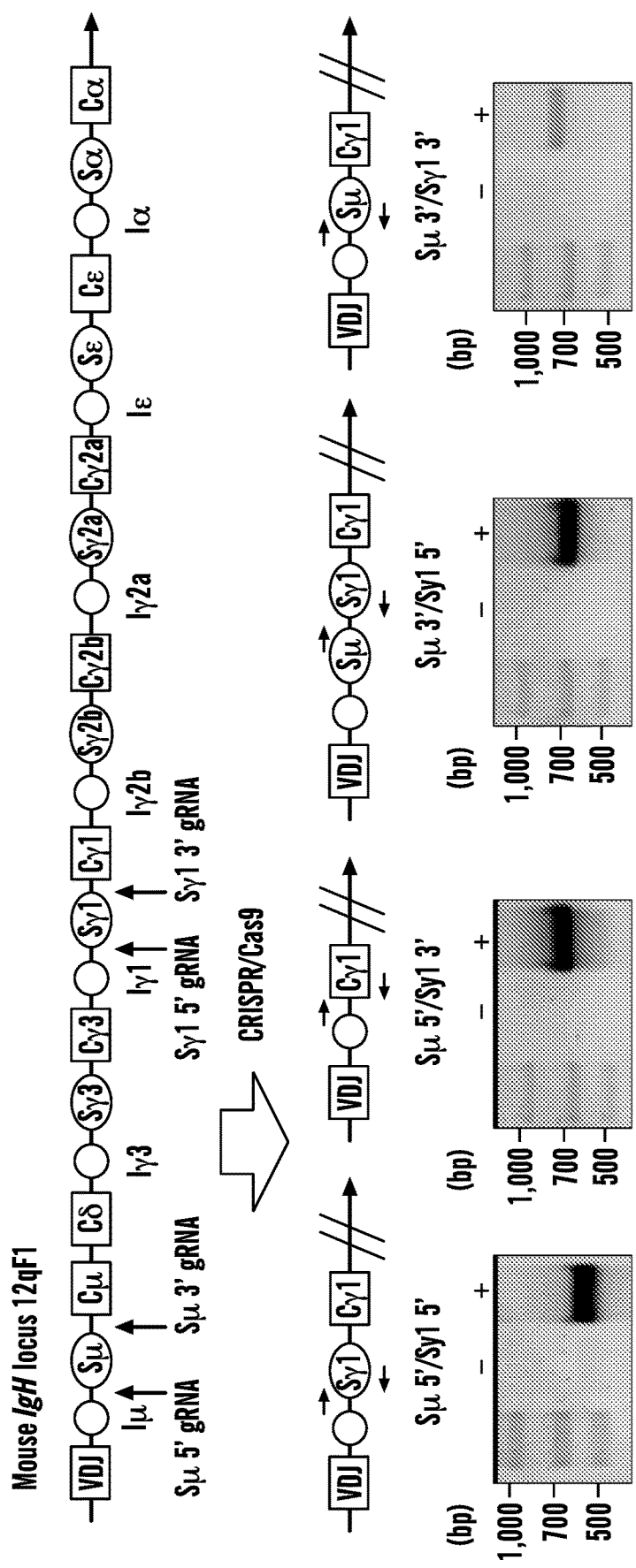
FIGS. 1A-1E. Induction of class switch recombination (CSR) by CRISPR/Cas9 system in mouse cells FIG. 1A. Top: Genomic organization of the mouse IgH constant region locus and position of the gRNAs used in this study. Bottom: Schematic representation of four possible CSR products induced by deletion of DNA segments between S$\mu$ and S$\gamma$1 regions. Black arrows on the bottom schematic representation indicate the positions for the PCR primers designed to sequence the deletion sites. Gels show PCR amplicons obtained with the indicated primers.

Unless otherwise explained, all technical and scientific terms used herein have the same meaning as commonly understood by one of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Definitions of common terms in molecular biology can be found in The Merck Manual of Diagnosis and Therapy, 19th Edition, published by Merck Sharp & Dohme Corp., 2011 (ISBN 978-0-911910-19-3) and the 2015 digital online edition at merckmanuals.com, Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties. Further, unless otherwise required by context, singular terms shall include pluralities and plural terms shall include the singular.

Unless otherwise stated, the embodiments of the present disclosure was performed using standard procedures known to one skilled in the art, for example, in Michael R. Green and Joseph Sambrook, Molecular Cloning: A Laboratory Manual, Cold Spring Harbor Laboratory Press, Cold Spring Harbor, N.Y., USA (2012); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Meolcular Biology, Vo. 203, 2003, Transgenic Mouse, edited by Marten H. Hofker and Jan van Deursen, which are all herein incorporated by reference in their entireties.

It should be understood that this invention in this disclosure is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Embodiments of the present disclosure relate to compositions, methods, and kits for directing CSR of the IgH chain genes in vivo in order to producing antibodies of any Ig subclass of one's choosing. The compositions, methods and kits described herein use the CRISPR/Cas9 system to edit the IgH chain segments (or exons) in the IgH locus, thereby inducing CSR of the IgH chain genes. The compositions, methods, and kits do not depend on the activation of B cells, the B cell membrane-bound antibody molecule (i.e., the B cell receptor), or the T cell derived cytokines to induce CSR.

Ig class switching, also known as isotype switching, isotypic commutation or CSR, is a biological mechanism that changes a B cell's production of immunoglobulin (antibodies) from one type to another, such as from the isotype IgM to the isotype IgG. During this process, the constant-region portion of the antibody heavy chain is changed, but the variable region of the Ig heavy chain stays the same (the terms "variable" and "constant" refer to changes or lack thereof between antibodies that target different epitopes). Since the variable region does not change, class switching does not affect antigen specificity. Instead, the antibody retains affinity for the same antigens, but can interact with different effector molecules.

In nature, class switching occurs after activation of a mature B cell via its membrane-bound antibody molecule (i.e., the B cell receptor) to generate the different classes of antibody, all with the same variable domains as the original antibody generated in the immature B cell during the process of V(D)J recombination, but possessing distinct constant domains in their Ig heavy chains.

Naïve mature B cells produce both IgM and IgD, which are the first two heavy chain segments in the IgH locus. After activation by antigen, these B cells proliferate. If these activated B cells encounter specific signaling molecules via their CD40 and cytokine receptors (both modulated by T helper cells), they undergo antibody class switching to produce IgG, IgA or IgE antibodies. During class switching, the constant region of the IgH chain changes but the variable regions, and therefore antigenic specificity, stay the same.

This allows different daughter cells from the same activated B cell to produce antibodies of different isotypes or subtypes (e.g. IgG1, IgG2 etc.).

In the genome, the order of arrangement of the heavy chain (IgH) exons in the IgH locus in the human genome is as follows: μ (for IgM), δ (for IgD), γ3 (for IgG3), γ1 (for IgG1), α1 (for IgA1), γ2 (for IgG2), γ4 (for IgG4), ε (for IgE), and α2 (for IgA2). There are S regions located at the 5'-end of each of these exons in the genome.

In the genome, the order of arrangement of the heavy chain (IgH) exons in the IgH locus in the mouse genome is as follows: μ (for IgM), δ (for IgD), γ3 (for IgG3), γ1 (for IgG1), γ2b (for IgG2b), γ2a (for IgG2a), ε (for IgE), and α (for IgA). There are S regions located at the 5'-end of each of these exons in the genome.

Class switching occurs by a mechanism called CSR binding. CSR is a biological mechanism that allows the class of antibody produced by an activated B cell to change during a process known as isotype or class switching. During CSR, portions of the antibody heavy chain locus are removed from the chromosome, and the gene segments surrounding the deleted portion are rejoined to retain a functional antibody gene that produces antibody of a different isotype. DSB is the key initiating step of CSR". In physiological conditions, DSBs are introduced at the Ig genes by the activity of B cell specific enzymes such as RAG1/2 and AID3-5. Double-stranded breaks are generated in DNA at conserved nucleotide motifs, called switch (S) regions, which are upstream from gene segments that encode the constant regions of antibody heavy chains; these occur adjacent to all heavy chain constant region genes with the exception of the δ-chain. DNA is nicked and broken at two selected S-regions by the activity of a series of enzymes, including activation-induced (cytidine) deaminase (AID), uracil DNA glycosylase and apyrimidic/apurinic (AP)-endonucleases. The intervening DNA between the S-regions is subsequently deleted from the chromosome, removing unwanted μ or δ heavy chain constant region exons and allowing substitution of a γ,α or ε constant region gene segment. The free ends of the DNA are rejoined by a process called non-homologous end joining (NHEJ) to link the variable domain exon to the desired downstream constant domain exon of the antibody heavy chain. In the absence of non-homologous end joining, free ends of DNA may be rejoined by an alternative pathway biased toward microhomology joins. With the exception of the μ and δ genes, only one antibody heavy chain class is expressed by a B cell at any point in time.

During CSR, AID generates DSBs in the Ig locus by targeting repetitive sequences in the switch (S) regions that precede each IgH chain coding sequence[3-5]. Paired DSBs in the switch regions are then joined by the classical and alternative NHEJ pathways to generate a switch of the IgH[6]. This long range joining is thought to be part of a general mechanism of DNA repair where two DSBs are joined in cis over long chromosome distances[7]. Indeed, efficient CSR can be obtained in absence of AID or S regions after the introduction of DSBs by site-specific I-SceI endonuclease[8].

The bacterial Type II Clustered Regularly Interspaced Short Palindromic Repeat (CRISPR)/Cas (CRISPR Associated) systems have great potentials for RNA-guided genome editing, including multiplexing genome engineering, gene targeting by homologous recombination, regulation of transcription, chromosomal translocation formation, high-throughput functional genomic screens and even RNA editing[1, 2, 9, 10]. It has been demonstrated that when two DSBs are simultaneously introduced in a cell in vitro or in vivo by CRISPR/Cas9 activity, a variety of gene rearrangements are generated, including large deletions (up to 12 Mb), inversions and chromosomal translocations[11-14].

The inventors used a CRISPR/Cas9 system to bring about an RNA-guided genome editing and thereby bring about CSR in the IgH locus. The CRISPR/Cas9 system was used to edit both the mouse and human IgH chain genes in vivo so as to produce various Ig subclass antibodies by design. By delivering a Cas9 enzyme and at least two gRNAs using viral vector vehicles such as retrovirus or lentivirus into IgM+ mouse B cells and hybridomas, the inventors were able to induce CSR of the IgH chain to the desired subclass. Similarly, the inventors induced CSR in all human B cell lines tested with high efficiency to targeted IgH subclass. In addition, the inventors engineered mouse hybridomas to secrete the Fab' fragment instead of the whole Ig using this new approach. The inventors showed that the Ig genes in mouse and human cells can be edited to obtain any desired IgH switching. This CRISPR/Cas9 system based CSR in the B cells and hybridomas occurs independent of B cell activation by cytokines or by interaction with the cell-surface CD-40 receptor on the B cell or with the assistance of T helper cells.

The present disclosure provide compositions, methods' and kits for making antibodies having desired IgH subclass (e.g., IgA1, IgA2, IgG1, IgG2, IgG3, IgG4, IgM, IgE, and IgD) by using the CRISPR/Cas genome editing system to induce and simulate the naturally occurring CSR in vivo with specifically designed gRNA having specific gRNA guide sequences. The gRNA sequences target the excision site of the respective μ, δ,γ, α, or ε region gene segment in the IgH locus, these gene segment codes for the constant region of an IgH chain. Specifically, targeting the switch region (S region) of the respective respective μ, δ,γ, α, or ε region gene segment with in the IgH locus. The guide RNA sequences, in combination with the CRISPR/Cas genome editing system brings about the targeted excision of the respective μ, δ,γ, α, or ε constant region gene segment in the IgH locus.

In an aspect, a guide RNA (gRNA) is designed and used in combination with a Cas9 nuclease or nickase to specifically introduce a cut in a targeted/target gene DNA or targeted sequence in the IgH locus. Here, it is the selected S regions. In one embodiment, the target or targeted sequence is located at the S region of the IgH locus. This cut, allows one to specifically modify the targeted gene by, e.g., by homologous recombination. When two distinct gRNAs are used to specifically introduce two distinct cuts in the targeted/target gene DNA or targeted sequence, and the broken ends are allowed to homologously recombine, thereby permitting specific deletions are introduced in the targeted/target gene DNA or targeted sequence. In this way, the targeted/target gene DNA or targeted sequence is modified.

To induced the class switch of an IgM-positive cell to a desired subtype in the IgH genes, a two-gRNAs system is needed: the first gRNA is designed in either one of the regions that flank the Switch μ (either at the 5'-end or at the 3'end of Sμ; see Tables 4 and 5 for genomic coordinates and seed sequences; also see FIG. 1A); the second gRNA is designed in either one of the regions that flank the desired Switch (either at the 5'-end or at the 3'end of Sγ, Sε or Sα depending on whether one desires a class switch to IgG, IgE, or IgA respectively).

For example, to induce a CSR of an IgM-positive cell to an IgA, the first gRNA is designed for targeting either one of the regions that flank the S μ region (5'-end or 3'-end) and the second gRNA is designed for targeting either one of the regions that flank the S α region (5'-end or 3'-end). To induce a CSR of an IgM-positive cell to an IgE, the first gRNA is designed for targeting either one of the regions that flank the S μ region (5'-end or 3'-end) and the second gRNA is designed for targeting either one of the regions that flank the S ε region (5'-end or 3'-end). To induce a CSR of an IgM-positive cell to an IgG, the first gRNA is designed for targeting either one of the regions that flank the S μ region (5'-end or 3'-end) and the second gRNA is designed for targeting either one of the regions that flank the Sγ region (5'-end or 3'-end). If the IgG is IgG1, then the second gRNA is designed for targeting either one of the regions that flank the Sγ1 region (5'-end or 3'-end).). If the IgG is IgG2b, then the second gRNA is designed for targeting either one of the regions that flank the Sγ2b region (5'-end or 3'-end).

For a switch from any Ig subclasses to another one, a pair gRNAs will be selected accordingly: for example for a switch from a IgG subclass to IgA, the first gRNA will be designed in either the 5'-end or at the 3'end of the corresponding Sγ subclass; whereas the second gRNA in either the 5'-end or at the 3'end of Sa. (see FIG. 1A for the selection of the S region).

For the generation of Fab or Fab' F(ab')$_2$ fragments, the inventors indicated in this disclosure the tested gRNA as well as the genomic coordinates of the Ig gene where additional gRNA would be designed to obtain F(ab)' fragments from mouse B cells or mouse hybridoma.

The compositions, methods, and kits described herein provide the possibility of diversifying the antibody production from already established hybridomas. For example, when there is an antibody that already has been tested to show good specificity and titer. However, this good antibody is an IgG1, and it would be better to have an IgG2 or IgA having the same antigenic specificity, i.e. having the same variable region and recognize the same antigenic epitope. The corresponding hybridoma that produced the good antibody of the IgG1 subclass can then be induced in vitro to switch classes, and an IgG2 antibody can be obtained in one week from this hybridoma that previously produced IgG1 antibodies. As another exemplary, there is a good antibody already available, and just the Fab or Fab' or F(ab')$_2$ fragment of this good antibody would be more useful than the whole Ig for research or diagnostic purposes This is because, for some antibodies, the antibodies work better as Fab or Fab' or F(ab')$_2$ fragment than whole Ig. The compositions and methods described herein can transform a hybridoma that produces a whole Ig into a hybridoma producing only the Fab or Fab' or F(ab')$_2$ within one week, and the F'ab produced recognizes the same antigen as the whole Ig.

Accordingly, in one embodiment, provided herein is a composition for directing CSR of an IgH chain locus in a mammalian cell to a desired IgH subclass, the composition comprising a vector comprising a nucleic acid encoding a Cas9 nuclease or nickase and nucleic acids encoding at least two gRNAs.

In one embodiment, provided herein is a composition comprising a vector comprising a nucleic acid encoding a Cas9 nuclease or nickase and nucleic acids encoding at least two gRNAs for use in directing CSR of an IgH chain locus in a mammalian cell to a desired IgH subclass.

In some embodiments, the composition comprises one or more vectors. Each vector comprises a nucleic acid encoding the Cas9 or gRNA or both the Cas9 and the gRNA.

For example, the vector is a polycistronic vector, or a dicistronic vector, or a monocistric vector.

In another embodiment, provided herein is a composition comprising a first vector comprising a nucleic acid encoding a Cas9 nuclease or nickase, and a second vector comprising nucleic acids encoding at least two gRNAs, for use in directing CSR of an IgH chain locus in a mammalian cell to a desired IgH subclass, wherein the at least two gRNAs are distinct.

In yet another embodiment, provided herein is a composition comprising a first vector comprising a nucleic acid encoding a Cas9 nuclease or nickase, a second vector comprising a nucleic acids encoding a first gRNA, and a third vector comprising a nucleic acids encoding a second gRNA, for use in directing CSR of an IgH chain locus in a mammalian cell to a desired IgH subclass, wherein the first and second gRNAs are distinct.

In one embodiment, provided herein is a composition comprising a vector comprising a nucleic acid encoding a Cas9 nuclease or nickase and nucleic acids encoding a gRNA for use in a rapid method of production of monoclonal antibody of a desired IgH subclass or producing a monoclonal Fab or Fab' or F(ab')$_2$ fragment.

In another embodiment, provided herein is a composition comprising a first vector comprising a nucleic acid encoding a Cas9 nuclease or nickase, and a second vector comprising nucleic acids encoding a gRNAfor use in a rapid method of production of a monoclonal antibody having a desired IgH subclass or producing a monoclonal Fab or Fab' or F(ab')$_2$ fragment.

In one embodiment, provided herein is a composition comprising at least three coding nucleic acids, one nucleic acid encoding a Cas9 nuclease or nickase, a second nucleic acid encoding a first gRNA, and a third nucleic acid encoding a second gRNA, wherein the first and second gRNAs are distinct. This composition is useful for directing CSR of an IgH chain locus in a mammalian cell to a desired IgH subclass.

In one embodiment, provided herein is a composition comprising at least two coding nucleic acids, one nucleic acid encoding a Cas9 nuclease or nickase, and a second nucleic acid encoding a gRNA. This composition is useful for rapid production of a monoclonal antibody having a desired IgH subclass from a hybridoma clonal cell or for the production of a monoclonal Fab or Fab' or F(ab')$_2$ fragment from a hybridoma clonal cell.

In another embodiment, provided herein is a composition for directing CSR of an IgH chain locus in a mammalian cell to a desired IgH subclass, the composition comprising a nucleic acid encoding a Cas9 nuclease or nickase and nucleic acids encoding at least two gRNAs.

In one embodiment, provided herein is a composition comprising a nucleic acid encoding a Cas9 nuclease or nickase and nucleic acids encoding at least two gRNAs for use in directing CSR of an IgH chain locus in a mammalian cell to a desired IgH subclass.

In one embodiment, provided herein is a vector comprising a nucleic acid encoding a Cas9 nuclease or nickase and nucleic acids encoding at least two gRNAs, wherein the at least two gRNAs are distinct, and they are designed to target a S region in an IgH chain locus in a mammalian cell, with each gRNA targeting a different S region in the IgH locus. In some embodiments, the vector is a viral vector.

In one embodiment, provided herein is a composition comprising a nucleic acid encoding a Cas9 nuclease or nickase and nucleic acids encoding a gRNA for use in a rapid method of production of monoclonal antibody of a desired IgH subclass or producing a monoclonal Fab or Fab' or F(ab')$_2$ fragment.

In one embodiment, provided herein is a vector comprising a nucleic acid encoding a Cas9 nuclease or nickase and nucleic acids encoding a gRNA, wherein the gRNA targets the papain or pepsin cleavage site of the Fc region on the antibody.

In one embodiment, provided herein is a method for directing CSR of the IgH chain locus in a mammalian cell to a desired IgH subclass comprising contacting the mammalian cell with a composition of described herein.

In one embodiment, provided herein is a method for directing CSRof the IgH chain locus in a mammalian cell to a desired IgH subclass comprising contacting the mammalian cell with a vector comprising a nucleic acid encoding a Cas9 nuclease or nickase and nucleic acids encoding at least two gRNAs, or contacting with a composition comprising a vector described herein or contacting with a composition comprising the nucleic acids described.

In one embodiment, provided herein is a kit for directing CSR of an IgH chain locus in a mammalian cell to a desired IgH subclass, the kit comprising a vector comprising a nucleic acid encoding a Cas9 nuclease or nickase and nucleic acids encoding at least two gRNAs, at least two gRNAs are non-identical, ie., they are distinct, and they are designed to target a S region in an IgH chain locus in a mammalian cell, with each gRNA targeting a different S region in the IgH locus.

In one embodiment, provided herein is a kit for directing CSR of an IgH chain locus in a mammalian cell to a desired IgH subclass, the kit comprising a first vector comprising a nucleic acid encoding a Cas9 nuclease or nickase, and a second vector comprising nucleic acids encoding at least two gRNAs, wherein the first and second gRNAs are distinct and are designed to target a S region in an IgH chain locus in a mammalian cell, with each gRNA targeting a different S region in the IgH locus.

In one embodiment, provided herein is a kit for directing CSR of an IgH chain locus in a mammalian cell to a desired IgH subclass, the kit comprising a first vector comprising a nucleic acid encoding a Cas9 nuclease or nickase, a second vector comprising a nucleic acids encoding a first gRNA, and a third vector comprising a nucleic acids encoding a second gRNA, wherein the first and second gRNAs are distinct and are designed to target a S region in an IgH chain locus in a mammalian cell, with each gRNA targeting a different S region in the IgH locus.

In one embodiment, provided herein is a kit for directing CSR of an IgH chain locus in a mammalian cell to a desired IgH subclass, the kit comprising a vector comprising a nucleic acid encoding a Cas9 nuclease or nickase and nucleic acids encoding at least two gRNAs, at least two gRNAs are non-identical, ie., they are distinct, and they are designed to target a S region in an IgH chain locus in a mammalian cell, with each gRNA targeting a different S region in the IgH locus, and each gRNA comprise sequences selected from the sequences disclosed in Table 1, 4 and 5.

In one embodiment, provided herein is a kit for directing CSR of an IgH chain locus in a mammalian cell to a desired IgH subclass, the kit comprising a nucleic acid encoding a Cas9 nuclease or nickase and nucleic acids encoding at least two gRNAs, at least two gRNAs are distinct, non-identical, and they are designed to target a S region in an IgH chain locus in a mammalian cell, with each gRNA targeting a different S region in the IgH locus.

In one embodiment, provided herein is a kit for directing CSR of an IgH chain locus in a mammalian cell to a desired IgH subclass, the kit comprising at least three coding nucleic acids, one nucleic acid encoding a Cas9 nuclease or nickase, a second nucleic acid encoding a first gRNA, and a third nucleic acid encoding a second gRNA, wherein the first and second gRNAs are distinct.

In one embodiment, provided herein is a kit for directing CSR of an IgH chain locus in a mammalian cell to a desired IgH subclass, the kit comprising a nucleic acid encoding a Cas9 nuclease or nickase and nucleic acids encoding at least two gRNAs, at least two gRNAs are non-identical, ie., they are distinct, and they are designed to target a S region in an IgH chain locus in a mammalian cell, with each gRNA targeting a different S region in the IgH locus, and each gRNA comprise sequences selected from the sequences disclosed in Table 1, 4 and 5.

In one embodiment, provided herein is a kit for the use in rapid method of production of monoclonal antibody of a desired IgH subclass or producing a monoclonal Fab or Fab' or F(ab')$_2$ fragment, the kit comprising a nucleic acid encoding a Cas9 nuclease or nickase and nucleic acids encoding a gRNA, wherein the gRNA targets the papain or pepsin cleavage site of the Fc region on the antibody.

In one embodiment, provided herein is a kit for the use in rapid method of production of monoclonal antibody of a desired IgH subclass or producing a monoclonal Fab or Fab' or F(ab')$_2$ fragment, the kit comprising a nucleic acid encoding a Cas9 nuclease or nickase and a nucleic acid encoding a gRNA comprise sequences selected from the sequences disclosed in Table 1.

In one embodiment, provided herein is a kit for the use in rapid method of production of monoclonal antibody of a desired IgH subclass or producing a monoclonal Fab or Fab' or F(ab')$_2$ fragment, the kit comprising a vector comprising a nucleic acid encoding a Cas9 nuclease or nickase and a nucleic acid encoding a gRNA, wherein the gRNA targets the papain or pepsin cleavage site of the Fc region on the antibody.

In one embodiment, provided herein is a kit for the use in rapid method of production of monoclonal antibody of a desired IgH subclass or producing a monoclonal Fab or Fab' or F(ab')$_2$ fragment, the kit comprising a vector comprising a nucleic acid encoding a Cas9 nuclease or nickase and a nucleic acid encoding a gRNA comprise sequences selected from the sequences disclosed in Table 1.

In one embodiment, provided herein is a kit for the use in rapid method of production of monoclonal antibody of a desired IgH subclass or producing a monoclonal Fab or Fab' or F(ab')$_2$ fragment, the kit comprising a first vector comprising a nucleic acid encoding a Cas9 nuclease or nickase, and a second vector comprising nucleic acids encoding a gRNA, wherein the gRNA targets the papain or pepsin cleavage site of the Fc region on the antibody.

In one embodiment, provided is a composition for directing CSR of an IgH chain locus in a mammalian cell to a desired IgH subclass, the composition comprising a vector comprising a nucleic acid encoding a Cas9 nuclease or nickase and nucleic acids encoding at least two guide gRNAs, wherein the first gRNA is designed in either one of the regions that flank the Sμ region, either at the 5'-end or at the 3'end of Sμ region, and the second gRNA is designed in either one of the regions that flank a second desired S region (either at the 5'-end or at the 3'end of Sγ, Sε or Sα). The second desired S region is not the same with the Sμ region.

In one embodiment, provided is a composition for directing CSR of an IgH chain locus in a mammalian cell to a desired IgH subclass, the composition comprising a nucleic acid encoding a Cas9 nuclease or nickase and nucleic acids encoding at least two gRNAs, wherein the first gRNA is designed to target in either one of the regions that flank the Sμ region, either at the 5'-end or at the 3'end of Sμ, and the second gRNA is designed in either one of the regions that flank a second desired S region (either at the 5'-end or at the 3'end of Sγ, Sε or Sα).

In one embodiment, provided is a composition for directing CSR of an IgH chain locus in a mammalian cell from a IgG subclass to IgA, the composition comprising a vector comprising a nucleic acid encoding a Cas9 nuclease or nickase and nucleic acids encoding at least two gRNAs, wherein the first gRNA is designed to target in either the 5'-end or at the 3'end of the corresponding Sγ subclass; whereas the second gRNA is designed to target in either the 5'-end or at the 3'end of Sa. The at least two gRNAs are non-identical, ie., they are distinct.

In one embodiment, provided is a composition for directing CSR of an IgH chain locus in a mammalian cell from a IgG subclass to IgA, the composition comprising a nucleic acid encoding a Cas9 nuclease or nickase and nucleic acids encoding at least two guide RNAs (gRNAs), wherein the first gRNA is designed to target in either the 5'-end or at the 3'end of the corresponding Sγ subclass; whereas the second gRNA in either the 5'-end or at the 3'end of Sα.

In one embodiment, provided is a composition for directing CSR of an IgH chain locus in a mammalian cell from a IgG subclass to IgE, the composition comprising a vector comprising a nucleic acid encoding a Cas9 nuclease or nickase and nucleic acids encoding at least two guide RNAs (gRNAs), wherein the first gRNA is designed to target in either the 5'-end or at the 3'end of the corresponding Sγ subclass; whereas the second gRNA is designed to target in either the 5'-end or at the 3'end of Sε.

In one embodiment, provided is a composition for directing CSR of an IgH chain locus in a mammalian cell from a IgG subclass to IgE, the composition comprising a nucleic acid encoding a Cas9 nuclease or nickase and nucleic acids encoding at least two gRNAs, wherein the first gRNA is designed to target in either the 5'-end or at the 3'end of the corresponding Sγ subclass; whereas the second gRNA is designed to target in either the 5'-end or at the 3'end of Sε.

In one embodiment, provided herein is a rapid method of producing monoclonal antibody of a desired IgH subclass or producing a monoclonal Fab or Fab' or F(ab')₂ fragment, the method comprising providing a hybridoma clonal cell and contacting a hybridoma clonal cell with (i) a vector comprising a nucleic acid encoding a Cas9 nuclease or nickase and a nucleic acidsencoding a gRNA, or (ii) a composition described herein. For example, a composition comprising a vector comprising a nucleic acid encoding a Cas9 nuclease or nickase and a nucleic acid encoding a gRNA or a composition comprising a nucleic acid encoding a Cas9 nuclease or nickase and a nucleic acid encoding a gRNA. In one embodiment, the gRNA is designed to target the Fc region (constant region) of the antibody. In one embodiment, the gRNA is designed to target the papain or pepsin cleavage site in the Fc region of the antibody. In one embodiment, the hybridoma clonal cell produces antibodies that have already been tested to show good specificity and titer.

In one embodiment, provided herein is a rapid method of producing monoclonal antibody of a desired IgH subclass or producing a monoclonal Fab or Fab' or F(ab')₂ fragment, the method comprising providing a hybridoma clonal cell; and contacting a hybridoma clonal cell with a nucleic acid encoding a Cas9 nuclease or nickase and nucleic acids encoding a gRNA. In one embodiment, the gRNA is designed to target the Fc region (constant region) of the antibody. In one embodiment, the gRNA is designed to target the papain or pepsin cleavage site in the Fc region of the antibody. In one embodiment, the hybridoma clonal cell produces antibodies that have already been tested to show good specificity and titer.

In one embodiment, provided herein is a mammalian cell comprising a vector or vectors comprising an exogenous nucleic acid encoding a Cas9 nuclease or nickase and exogenous nucleic acids encoding at least two gRNAs, wherein the at least two gRNAs are distinct.

In one embodiment, provided herein is a mammalian cell comprising an exogenous nucleic acid encoding a Cas9 nuclease or nickase and exogenous nucleic acids encoding at least two gRNAs, wherein the at least two gRNAs are distinct.

In one embodiment, provided herein is a composition comprising a population of mammalian cells comprising a vector or vectors comprising an exogenous nucleic acid encoding a Cas9 nuclease or nickase and exogenous nucleic acids encoding at least two gRNAs, wherein the at least two gRNAs are distinct.

In one embodiment, provided herein is a composition comprising a population of mammalian cells comprising an exogenous nucleic acid encoding a Cas9 nuclease or nickase and exogenous nucleic acids encoding at least two gRNAs, wherein the at least two gRNAs are distinct.

In one embodiment, provided herein is a mammalian hybridoma clonal cell comprising a vector or vectors comprising an exogenous nucleic acid encoding a Cas9 nuclease or nickase and an exogenous nucleic acid encoding a gRNA, wherein the gRNA targets the papain or pepsin cleavage site of the Fc region on the antibody.

In one embodiment, provided herein is a mammalian hybridoma clonal cell comprising an exogenous nucleic acid encoding a Cas9 nuclease or nickase and an exogenous nucleic acid encoding a gRNA, wherein the gRNA targets the papain or pepsin cleavage site of the Fc region on the antibody.

In one embodiment, provided herein is a composition comprising a population of mammalian hybridoma clonal cells comprising a vector or vectors comprising an exogenous nucleic acid encoding a Cas9 nuclease or nickase and an exogenous nucleic acid encoding a gRNA, wherein the gRNA targets the papain or pepsin cleavage site of the Fc region on the antibody.

In one embodiment, provided herein is a composition comprising a population of mammalian hybridoma clonal cells comprising comprising an exogenous nucleic acid encoding a Cas9 nuclease or nickase and a nucleic acid encoding a gRNA, wherein the gRNA targets the papain or pepsin cleavage site of the Fc region on the antibody.

In bacteria, the CRISPR/Cas9 genome editing is carried out with a Type II CRISPR system. When utilized for genome editing, this system includes Cas9, CRISPR RNA (crRNA), trans-activating crRNA (tracrRNA) along with an optional section of DNA repair template that is utilized in either non-homologous end joining (NHEJ) or homology directed repair (HDR).

Cas9 (CRISPR associated protein 9) is an RNA-guided DNA endonuclease enzyme associated with the CRISPR (Clustered Regularly Interspaced Short Palindromic Repeats) adaptive immunity system in *Streptococcus pyogenes*, among other bacteria. *S. pyogenes* utilizes Cas9 to memorize and later interrogate and cleave foreign DNA, such as invading bacteriophage DNA or plasmid DNA. Cas9 performs this interrogation by unwinding foreign DNA and checking whether it is complementary to the 20 basepair spacer region of the guide RNA. If the DNA substrate is complementary to the guide RNA, Cas9 cleaves the invading DNA. In this sense, the CRISPR/Cas9 mechanism has a number of parallels with the RNA interference (RNAi) mechanism in eukaryotes.

In order to cut DNA at a specific site, Cas9 proteins require the presence of a gRNA and a protospacer adjacent motif (PAM), which immediately follows the gRNA target sequence in the targeted polynucleotide gene sequence. The PAM is located at the 3' end of the gRNA target sequence but is not part of the gRNA. Different Cas proteins require a different PAM. Accordingly, selection of a specific polynucleotide gRNA target sequence (e.g., on the APP nucleic acid sequence) by a gRNA is generally based on the recombinant Cas protein used. The PAM for the S. pyogenes Cas9 CRISPR system is 5 -NRG-3', where R is either A or G, and characterizes the specificity of this system in human cells. The PAM of S. aureus is NNGRR. The S. pyogenes Type II system naturally prefers to use an "NGG" sequence, where "N" can be any nucleotide, but also accepts other PAM sequences, such as "NAG" in engineered systems. Similarly, the Cas9 derived from Neisseria meningitidis (NmCas9) normally has a native PAM of NNNNGATT, but has activity across a variety of PAMs, including a highly degenerate NNNNGNNN PAM.

In one embodiment of any composition or method or kit described, the PAM for a Cas9 protein used in accordance with the present disclosure is a NGG trinucleotide-sequence.

To bring about genome editing using the CRISPR/Cas system, only two components are necessary to be present with the genomic DNA destined for editing: a homing device and an endonuclease. The synthetic, man-made, non-naturally occurring guide RNA (gRNA) constitutes the homing device for the endonuclease component of the CRISPR/Cas system. The endonuclease in the CRISPR/Cas system is a Cas endonuclease. The Cas endonuclease can cleave a single strand (a nicknase) or two strands of a dsDNA (nuclease). The gRNA and the Cas endonuclease together form a protein-RNA complex. The gRNA is the homing device of the a protein-RNA complex because the gRNA brings the Cas endonuclease to a specific location (a targeted location) on a double-stranded DNA (ds DNA, ie. part of the genomic DNA) for cleaving the DNA at that specific location via the endonuclease catalytic activity while the endonuclease is in the protein-RNA complex, a ribonucleoprotein complex. Therefore, the gRNA is used for "targeting" the endonuclease component of the CRISPR/Cas system to a specified site on a dsRNA genome destined for cleavage. The gRNA "homes" in on the specific location (the targeted sequence) on the dsDNA (the genomic DNA) where cleavage is intended by having a targeting sequence that is complementary to the sequence found on the specific location (the targeted sequence). The specified location (the targeted sequence) on a dsDNA genome where cleavage by the endonuclease is intended and desired is the targeted sequence. The complementary sequence on the gRNA, usually the guide sequence or the seed sequence, the sequence being complementary to the targeted location on the dsDNA genome is the targeting sequence. Therefore, the target specificity of Cas9 stems from the guide RNA:DNA complementarity and engineering Cas9 to specifically cleave at targeted new DNA is straightforward and well known in the art. See Cong, L.; Ran, F. A.; Cox, D.; Lin, S.; Barretto, R.; Habib, N.; Hsu, P. D.; Wu, X.; Jiang, W.; Marraffini, L. A.; Zhang, F. (3 Jan. 2013). "Multiplex Genome Engineering Using CRISPR/Cas Systems". Science 339 (6121): 819-823; U.S. Pat. No. 8,697,359; International PCT Patent Publication Nos: WO 2015/168800, the contents of each are incorporated by reference in its entirety.

For the CRISPR/Cas system's specificity, two factors are needed, the CRISPR targeting sequence, which is on the gRNA as described herein and the PAM. The PAM sequence on the host genome is recognized by the protein structure of Cas9. PAM is a short sequence and is not very specific (e.g. the SpCas9 PAM sequence is 5'-NGG-3' and in the human genome, such PAM sequence occurs roughly every 8 to 12 base pairs). Ran FA, Hsu PD, Wright J, Agarwala V, Scott DA, Zhang F (2013). "Genome engineering using the CRISPR-Cas9 system". Nature Protocols 8 (11): 2281-30.

In bacteria, the native Cas endonuclease such as Cas9 requires a guide RNA (gRNA) composed of two disparate RNAs that associate to make the guide—the CRISPR RNA (crRNA), and the trans-activating RNA (tracrRNA). The tracrRNA is for binding the Cas endonuclease (ie. Cas9 recognition) and for the recognition of the PAM sequence. The crRNA is for bringing the Cas endonuclease to a targeted location/sequence on dsDNA, the targeted location/sequence is the site where cleavage by the Cas endonuclease is intended. In the CRISPR/Cas system that is known in the art, Cas9 targeting has been simplified through the engineering of a chimeric single guide RNA. See U.S. Pat. No. 8,697,359; International PCT Patent Publication Nos: WO 2015/168800, the contents of each are incorporated by reference in its entirety.

The targeted or target sequence for the gRNAs using the type II CRISPR system of S. pyogenes described in this disclosure have the formula having N12-2ONGG, where NGG represent the PAM site from S. pyogenes, and N12-20 represents the 12-20 nucleotides directly 5' to the PAM site. Additional PAM site sequences from other species of bacteria include NGGNG, NNNNGATT, NNAGAA, NNAGAAW, and NAAAAC, where N is any nucleotide (standard or modified) and W is a nucleotide with weak interactions, such as A or T/U. See, e.g., US 20140273233, WO 2013176772, Cong et al., (2012), Science 339 (6121): 819-823, Jinek et al., (2012), Science 337 (6096): 816-821, Mali et al, (2013), Science 339 (6121): 823-826, Gasiunas et al., (2012), Proc Natl Acad Sci USA. 109 (39): E2579-E2586, Cho et al., (2013) Nature Biotechnology 31, 230-232, Hou et al., Proc Natl Acad Sci USA. 2013 Sep. 24; 110(39):15644-9, Mojica et al., Microbiology. 2009 March; 155(Pt 3):733-40, and at the ADDGENE organization website under the section on CRISPR.

As used herein, the expression "gRNA" refers to a guide RNA which is a fusion between the gRNA guide sequence (crRNA) and the Cas9 recognition sequence (tracrRNA). It provides both targeting specificity and scaffolding/binding ability for Cas9 nuclease or nickase. gRNAs of the present disclosure do not exist in nature, i.e., is a non-naturally-occuring nucleic acid.

The gRNAs of the present disclosure generally comprises (or consists of) a "gRNA guide sequence" and a Cas (e.g., Cas9) recognition sequence (tracrRNA), which is necessary for Cas (e.g., Cas9) binding to the targeted IgH locus.

As used herein, the expression "gRNA guide sequence" refers to the nucleotide sequence that is complementary to the nucleotide sequence that immediately precedes the PAM (i.e., in 5' of the PAM) in the genomic DNA. It corresponds to the protospacer or the target polynucleotide gene sequence. It is what gets put into a gRNA expression plasmid; it does not include the PAM sequence. It is the sequence that confers target specificity. It requires a Cas9 recognition sequence (tracrRNA) to bind to Cas9. The gRNA guide sequence is between 16-25 nucleotides, preferably between 18-22 nucleotides and even more preferably 19 nucleotides or 20 nucleotides long. The gRNA guide sequence recognizes and binds to the targeted gene of interest, which is the selected sequence that immediately precedes the PAM. It hybridizes with (i.e., is complementary to) the opposite strand of a target gene sequence, which comprises the protospacer and the PAM (i.e., it hybridizes with the DNA strand opposite to the PAM).

The gRNA guide sequence comprises a targeting sequence that is complementary to the targeted/target sequence having the formula N12-20NGG but minus the NGG (PAM).

A Cas recognition sequence (e.g., Cas9 recognition sequence) refers to the portion of the gRNA that links the gRNA guide sequence (crRNA) to the Cas nuclease. It acts as a guide for binding a endonuclease or nickase and brings the endonuclease or nickase to the target genomic DNA for the enzyme to effectuate DSBs. A gRNA with a bound endonuclease or nickase will cleave the target genomic nucleic acid when the gRNA guide sequence complementarily binds to the target sequence. In an embodiment, Cas recognition sequence is a Cas9 recognition sequence.

Various Cas9 recognition sequences (tracrRNA) are known in the art, for example, in Cong, L.; Ran, F. A.; Cox, D.; Lin, S.; Barretto, R.; Habib, N.; Hsu, P. D.; Wu, X.; Jiang, W.; Marraffini, L. A.; Zhang, F. (3 Jan. 2013). "Multiplex Genome Engineering Using CRISPR/Cas Systems". Science 339 (6121): 819-823; U.S. Pat. No. 8,697,359; International PCT Patent Publication Nos: WO 2015/168800, the contents of each are incorporated by reference in its entirety.

The gRNA comprises a "gRNA guide sequence" (crRNA) or "gRNA targeted sequence" which corresponds to the target sequence on the target polynucleotide gene sequence (here, it is the S regions of the endogenous the IgH locus, for example, in the Sµ, Sγ3, Sγ1, Sγ2b, Sγ2a, Sc or Sa regions of the IgH locus) that is followed by a PAM sequence. See Table 1, 4 and 5. The gRNA comprises a "G" at the 5' end of the polynucleotide sequence. The presence of a "G" in 5' is preferred when the gRNA is expressed under the control of the U6 promoter. The CRISPR/Cas9 system of the present disclosure can use crRNA of varying lengths. The crRNA may comprise at least a 10 nts, at least 11 nts, at least a 12 nts, at least a 13 nts, at least a 14 nts, at least a 15 nts, at least a 16 nts, at least a 17 nts, at least a 18 nts, at least a 19 nts, at least a 20 nts, at least a 21 nts, at least a 22 nts, at least a 23 nts, at least a 24 nts, at least a 25 nts, at least a 30 nts, or at least a 35 nts of the targeted S regions of the IgH locus which is followed by a PAM sequence. The crRNA can be least 17 nucleotides (17, 18, 19, 20, 21, 22, 23), preferably between 17 and 30 nts long, more preferably between 18-22 nucleotides long. In an embodiment, crRNA is between 10-40, 10-30, 12-30, 15-30, 18-30, or 10-22 nucleotides long. The PAM sequence can be "NGG", where "N" can be any nucleotide. A gRNA's crRNA can target any region of a target gene (e.g., APP) which is immediately upstream (contiguous, adjoining, in 5') to a PAM (e.g., NGG) sequence. In an embodiment, the gRNA's crRNA can target any region which is followed by a PAM identified on Tables 1, 4 and 5.

In various embodiments of any composition, method, or kit described, the guide sequence can comprise from about 10 nucleotides to more than about 25 nucleotides. For example, the region of base pairing between the guide sequence and the corresponding target site sequence can be about 10, 11, 12, 13, 14, 15, 16, 17, 18, 19, 20, 22, 23, 24, 25, or more than 25 nucleotides in length. In an exemplary embodiment, the guide sequence is about 17-20 nucleotides in length, such as 20 nucleotides.

In one embodiment of any composition, method, or kit described, the gRNA described herein comprises a crRNA comprising a seed region of at least 10 consecutive nucleotides of a targeted sequence in a IgH gene polynucleotide sequence present in the cell and a Cas9 recognition sequence, wherein the targeting sequence of the gRNA is contiguous to a PAM in the IgH gene polynucleotide sequence and wherein the PAM is recognized by a ribonucleoprotein complex comprising a Cas9 nuclease or nickase.

In one embodiment of any composition, method, or kit described, the crRNA is complementary to the targeted sequence in an IgH gene locus polynucleotide sequence.

In one embodiment of any composition, method, or kit described, the seed region in the crRNA is complementary to the targeted sequence in an IgH gene locus polynucleotide sequence, i.e., the various S regions, or Fc region.

In one embodiment of any composition, method, or kit described, the location on the IgH gene polynucleotide sequence that is targeted is the IgH locus.

The 'seed sequence' or "seed region" is the sequence closest to the PAM. The seed sequence is most important for targeting and specificity. The PAM is most important for for Cas9 recognition and the cleavage of the nucleic acid backbone. The gRNA's crRNA (also refered to as gRNA guide sequence) with a 20 nt homology to the targeted sequence can tolerate several mismatches. It is therefore of paramount importance to select target sites which are unique and do not have closely homologous sequences elsewhere in the genome.

In one embodiment of any composition, method, or kit described, the guide sequence of gRNA (i.e. crRNA) comprises a seed region of at least 10 consecutive nucleotides of a target sequence preceding a PAM in an IgH locus sequence present in the mammalian cell.

In another embodiment of any composition, method, or kit described, the guide sequence of gRNA (i.e. crRNA) comprises a seed region perfectly complementary to a targeted sequence in the endogenous the IgH locus of the cell.

In another embodiment of any composition, method, or kit described, the guide sequence of gRNA (i.e. crRNA) comprises a seed region sequence selected from the sequences disclosed in Table 1,4 and 5.

More specifically, in one embodiment, the guide sequences of gRNAs described herein comprise seed regions that are perfectly complementary to targeted sequences in the S regions of the endogenous the IgH locus of the cell.

Although a perfect match between the gRNA guide sequence and the DNA sequence on the targeted S regions of the endogenous the IgH locus of the cell is preferred, a mismatch between a gRNA guide sequence and targeted sequence of the S region is also permitted as along as it still allows hybridization of the gRNA with the complementary strand of the gRNA target polynucleotide sequence on the targeted gene. In some embodiments, the seed sequence of between 8-12 consecutive nucleotides in the gRNA, which perfectly matches a corresponding portion of the targeted gRNA sequence is preferred for proper recognition of the target sequence. The remainder of the guide sequence may comprise one or more mismatches. In other embodiments, the seed sequence of between 16-25 consecutive nucleotides in the gRNA, which perfectly matches a corresponding portion of the gRNA targeted sequence. In general, gRNA activity is inversely correlated with the number of mismatches. Preferably, the gRNA of the present invention comprises 7 mismatches, 6 mismatches, 5 mismatches, 4 mismatches, 3 mismatches, more preferably 2 mismatches, or less, and even more preferably no mismatch, with the corresponding gRNA target gene sequence (less the PAM). Preferably, the gRNA nucleic acid sequence is at least 90%, 91%, 92%, 93%, 94%, 95%, 96%, 97%, 98% and 99% identical to the gRNA target polynucleotide sequence in the gene of interest (e.g., IgH locus). Of course, the smaller the number of nucleotides in the gRNA guide sequence the smaller the number of mismatches tolerated. The binding affinity is thought to depend on the sum of matching gRNA-DNA combinations.

In one embodiment of any composition, method, or kit described, the gRNA guide sequence of the present disclosure consists of at least 16 or 17 contiguous nucleotides of the targeted sequence in the S regions of the endogenous the IgH locus of the cell.

In one embodiment of any composition, method, or kit described, the gRNA further comprises a a cis-blocking sequence, which is complementary and capable of hybridization to at least a portion of the above-described guide sequence. The blocking sequence can be 5-20 nucleotides long, e.g., 5, 6, 7, 8, 9, 10, 11, 12, 13, 14, 15, 16, 17, 18, 19, or 20 nucleotides in length. In the absence of the target of the guide sequence, the cis-blocking sequence hybridizes to the guide sequence and forms a duplex stem. The formation of the stem makes fewer nucleotides on the guide sequence available to both target and non-target sequences, but unzipping of the stem is more thermodynamically favorable for hybridization of the target sequence to the guide sequence, and hybridization of the guide sequence to non-target sequences is thus reduced.

To that end, computational analysis of the thermodynamic secondary structural properties of the guide sequence and/or the entire guide RNA as a whole can be used to create a cis-blocking sequence. For example, GC content and/or length of the blocking sequence can be used to achieve the desired level of binding affinity. Utilizing standard and/or modified nucleotides, the cis-blocking sequence can be designed to weakly base pair with part of the guide sequence of the guide RNA, thereby sequestering this region from binding to off-target DNA sequences that only partially match the guide sequence. Such weak base-pairing in the cis-blocked stem will be out-competed and melted by a fully cognate DNA target sequence when the cis-blocked guide RNA-Cas9 complex recognizes the on-target sequence. Thus, Cas9-guided binding and/or cleavage of a cognate DNA target occurs with improved specificity when a well-designed cis-blocking sequence is included. The blocking sequence may be 3' or 5' with respect to the guide sequence if they are in the same RNA molecule. If the guide RNA consists of two or more RNA molecules, they can be in separate RNA molecules. Methods of designing the cis-block element for a gRNA is known in the art, as described in US 2016/0040189, the contents of which are incorporated herein by reference in its entirety.

In an embodiment of any composition, method, or kit described, the target nucleic acid sequences selected for the above-mentioned gRNA are located in the S regions of the endogenous the IgH locus, for example, in the Sμ, Sγ3, Sγ1, Sγ2b, Sγ2a, Sε or Sα regions of the IgH locus.

In an embodiment of any composition, method, or kit described, the gRNA described here is an engineered single strand RNA with a guide sequence located at the 5'-end and the guide sequence is complementary to a target nucleic acid sequence on the IgH chain locus in the genome.

In an embodiment of any composition, method, or kit described, the target nucleic acid sequence on the IgH chain locus in the genome for the gRNA guide sequence is a S region in an IgH chain locus in a mammalian cell.

In an embodiment of any composition, method, or kit described, the target nucleic acid sequence on the IgH chain locus in the genome for the gRNA guide sequence is the papain or pepsin cleavage site of the Fc region on the antibody in a mammalian cell.

In an embodiment of any composition, method, or kit described, the target nucleic acid sequence selected for the above-mentioned gRNA is located at the 5'-end of a S region of the endogenous the IgH locus, for example, in the Sμ, Sγ3, Sγ1, Sγ2b, Sγ2a, Sε or Sα regions of the IgH locus.

In an embodiment of any composition, method, or kit described, the target nucleic acid sequence selected for the above-mentioned gRNA is located at the 3'-end of a S region of the endogenous the IgH locus, for example, in the Sμ, Sγ3, Sγ1, Sγ2b, Sγ2a, Sε or Sα regions of the IgH locus.

In an embodiment of any composition, method, or kit described, the target nucleic acid sequence selected for the above-mentioned gRNA is located in S regions described in Tables 4 and 5 of the mouse and human genome.

In an embodiment of any composition, method, or kit described, the targeted nucleic acid sequence selected for the above-mentioned gRNA is located anywhere within the targeted S region. In other embodiments of any composition, method, or kit described, the targeted nucleic acid sequence for the above-mentioned gRNA is located at either the 5'-end of the 3'-end of the targeted S region. The S regions are on average about ~200-300 base pair long and the estimated number of occurrence of a particulary type of PAM sequence in a nucleotide sequence of ~200-300 base pair long is approximately 4-5. Accordingly, in an S region, there can be several gRNA target sequences. See Table 5.

In one embodiment of any composition, method, or kit described, the PAM motif that is contiguous with the gRNA guide sequence is a three nucleotide motif, -NGG-, wherein N is any nucleotide, (A, T, G, or C; adenine=A, cytosine=C, guanine=G, thymine=T) and G is guanine.

In one embodiment of any composition, method, or kit described, the PAM comprises a NGG trinucleotide-sequence or an NNGRR nucleotide sequence.

In general, gRNAs guide sequences for genome editing is determined using publicly available softwares for identifying and design effective candidate gRNA guide sequences, e.g. CRISPR gRNA program at the Board Institute of the Massachusetts Institute of Technology. Many online tools are available to aid in designing effective gRNA guide sequences for genome editing using the CRISPR/Cas 9 system. A skilled artisan simply insert the targeted DNA sequence of the selected S region into the software program (see Table 4 for genome location of the S regions that can be targeted and used in the program to generate effective gRNA guide sequences). The program then provides a list of candidate gRNA guide sequences. In one embodiment, gRNA guide sequences with a score of 20 & above according to the CRISPR gRNA program are selected. The candidate gRNA guide sequences are easily tested according to the methods described in the EXAMPLE section and is well within the skills of one in the art. Table 5 shows a list of gRNA seed sequences that have a score of 20 & above according to the CRISPR gRNA program, and are located at the 5' and 3' end of the different S regions.

In one embodiment of any composition, method, or kit described, the target sequence for the gRNA guide sequence is within a switch (S) region which is upstream from a gene segment/nucleic acid sequence that encode a constant region of an antibody heavy chain, i.e., the Fc region.

In one embodiment of any composition or method described, the method comprises two gRNAs, a first gRNA which guide sequence targeting a first S region of the IgH locus and a second gRNA which guide sequence targeting a second S region on the IgH, wherein the first S region and the second S region targeted by the two respective gRNAs are different. For example, the first S region targeted is Sμ and the second S region targeted is Sa, or the the first S region targeted is Sμ and the second S region targeted is Sε.

In one embodiment of any composition, method, or kit described, the target sequence for the gRNA guide sequence flanks an S region.

In one embodiment of any composition or method or kit described, the target sequence for the gRNA guide sequence flanks a gene segment/nucleic acid sequence that encode a constant region of an Ig heavy chain. In other words, the exon that is the constant region gene segment in the IgH gene. Here, DSBs created by the Cas9 allows the excision of the constant region gene segment of the antibody, leaving behing the coding sequence for the variable region intact. This results in producing the Fab fragment.

In one embodiment of any composition, method, or kit described, the exon constant region gene segment in the IgH gene is selected from the group consisting of μ, δ,γ, α, or ε.

In one embodiment of any composition, method, or kit described, the exon constant region gene segment in the IgH gene is selected from the group consisting of μ (for IgM), δ (for IgD), γ3 (for IgG3), γ1 (for IgG1), α1 (for IgA1), γ2 (for IgG2), γ4 (for IgG4), ε (for IgE), and α2 (for IgA2).

In one embodiment of any composition, method, or kit described, the guide sequence of the gRNA comprises sequences selected from Table 1, 4 and 5.

In one embodiment of any composition, method, or kit described, the guide sequence of the gRNA is selected from Table 1, 4 and 5.

In one embodiment of any composition, method, or kit described, the guide sequence of the gRNA is complementary to those described in Table 1, 4 and 5.

In one embodiment of any kit described, the kit further provides an instruction table similar to that of Table 4 for teaching the selection of gRNA for the desired class switching.

The gRNAs and endonuclease can be introduced to the cells where genome editing is to be carried out by a number of methods known in the art. For example, electroporation of DNA, RNA or ribonucleocomplexes is the most common and cheaper system. For more efficient delivery of the gRNAs and endonuclease, delivery systems such as those based on lentivirus (LVs), adenovirus (AdV) and adeno-associated virus (AAV) are used. Plasmids and vectors for the one-stop-expression of both the gRNAs and the Cas 9 protein in a single vector are commercially. For example, ORIGENE vectors that have the lenti-viral backbone.

Various site-specific endonucleases are used for the compositions and methods described herein. These are often called nucleases and nickases. Site-specific endonucleases are known in art. For example, see U.S. Pat. No. 8,697,359; International PCT Patent Publication Nos: WO 2015/168800, the contents of each are incorporated by reference in its entirety. For example, dCas9-FoKI nucleases are designed recombinant dimeric nucleases (RFNs) that can recognize extended sequences and edit endogenous genes with high efficiency in human cells. These nucleases comprise a dimerization-dependent wild type Fold nuclease domain fused to a catalytically inactive Cas9 (dCas9) protein. Dimers of the fusion proteins mediate sequence specific DNA cleavage when bound to target sites composed of two half-sites (each bound to a dCas9 (i.e., a Cas9 nuclease devoid of nuclease activity) monomer domain) with a spacer sequence between them. The dCas9-FoKI dimeric nucleases require dimerization for efficient genome editing activity and thus, use two gRNAs for introducing a cut into DNA.

The recombinant Cas protein that can be used in accordance with the present invention is i) derived from a naturally occurring Cas; and ii) has a nuclease (or nickase) activity to introduce a DSB (or two SSBs in the case of a nickase) in cellular DNA when in the presence of appropriate gRNA(s). Thus, as used herein, the term "Cas9 nuclease" refers to a recombinant protein which is derived from a naturally occurring Cas9 which has nuclease activity and which function with the gRNAs of the present invention to introduce DSBs in the targeted DNA. In an embodiment, the Cas9 nuclease is a dCas9 protein (i.e., a mutated Cas9 protein devoid of nuclease activity) fused with a dimerization-dependent Fold nuclease domain. In another embodiment, the Cas protein is a Cas9 protein having a nickase activity.

As used herein, the term "Cas9 nickase" refers to a recombinant protein which is derived from a naturally occurring Cas9 and which has one of the two nuclease domains inactivated such that it introduces single stranded breaks (SSB) into the DNA. It can be either the RuvC or HNH domain. In a further embodiment, the Cas protein is a Cas9 nuclease. In accordance with the present invention, the Cas9 protein can be derived from any naturally occurring source.

For example, Cas9 proteins are natural effector proteins produced by numerous species of bacteria including *Streptococcus pyogene, Streptococcus thermophiles, Staphylococcus aureus*, and *Neisseria meningitides*. Accordingly, in an embodiment, the Cas protein useful for the compositions, methods, or kits disclosed is a Cas9 nuclease/nickase derived from *S. pyogene, S. thermophiles, S. aureus* or *N meningitides*. In an embodiment, the Cas9 recombinant protein useful for the compositions, methods, or kits disclosed is a human-codon optimized Cas9 derived from *S. pyogenes* (hSpCas9). In an embodiment, the Cas9 recombinant protein useful for the compositions, methods, or kits disclosed is a human-codon optimized Cas9 derived from *S. aureus* (hSaCas9).

The Cas9 cuts 3-4 base-pair (bp) upstream of the PAM sequence. There can be some off-target DSBs using wildtype Cas9. The degree of off-target effects depends on a number of factors, including: how closely homologous the off-target sites are compared to the on-target site, the specific site sequence, and the concentration of Cas9 and guide RNA (gRNA). These considerations only matter if the PAM sequence is immediately adjacent to the nearly-homologous target sites. The mere presence of additional PAM sequences should not be sufficient to generate off-target DSBs; there needs to be extensive homology of the protospacer followed by PAM.

The Cas or other nuclease/nickase recombinant protein useful for the compositions, methods, or kits disclosed preferably comprises at least one nuclear localization signal (NLS) to target the protein into the cell nucleus. Accordingly, as used herein the expression "nuclear localization signal" or "NLS" refers to an amino acid sequence, which 'tags' a protein for import into the cell nucleus by nuclear transport. Typically, this signal consists of one or more short sequences of positively charged lysines or arginines exposed on the protein surface. Different nuclear localized proteins may share the same NLS. An NLS has the opposite function of a nuclear export signal, which targets proteins out of the nucleus. Classical NLSs can be further classified as either monopartite or bipartite. NLS are known in the art, for example, in U.S. Pat. No. 6,759,231 and in U.S. Patent Application No: US20130023643, the contents are incorporated by reference in their entirety.

In one embodiment of any composition, method, or kit described, the Cas9 nuclease or nickase is a hSpCas9 nuclease, a hSaCas9 nuclease, a hSpCas9 nickase, a hSaCas9 nickase or a dCas9-FoId nuclease, wherein the "h" therein indicates human codon optimized.

Genetic constructs encoding a Cas 9 protein (nuclease or nickase) in accordance with the present disclosure can be made using either conventional gene synthesis or modular assembly. A humanized Cas9 construct is publicly available for example at the repository Addgene (for example Addgene plasmids pX330™, pX335™ (nickase), pX458™, pX459™, pX460™, pX461™, pX462™, pX165™ pX260™, pX334™ (nickase)).

In one embodiment of any composition, method, or kits described, the desired IgH subclass is selected from the group consisting of IgA1, IgA2, IgM, IgE, IgD, IgG1, IgG2, and IgG3 and IgG4.

In one embodiment of any composition, method, or kits described, the vector described herein is a viral vector. For example, a lentivirus, a retrovirus, an adenovirus, or an adeno-associated virus. For example, ORIGENE vectors that have the lenti-viral backbone.

In one embodiment of any composition, method, or kits described, the mammalian cell is a B lymphocyte or a hybridoma cell.

In one embodiment of any composition, method, or kits described, the B lymphocyte is a naïe or activated B lymphocyte.

In one embodiment of any composition, method, or kits described, the mammalian cell is a human, mouse, rat, donkey, monkey, pig, horse, hamster, or guinea pig cell.

In one embodiment of any composition, method, or kits described, the B lymphocyte is derived from a mouse, a rat, a human, a donkey, a monkey, a pig, a horse, a hamster, or a guinea pig.

In one embodiment of any composition, method, or kits described, the vector described expresses the Cas9 nuclease or nickase and the at least gRNA in vivo in the mammalian cell.

In one embodiment of any composition, method, or kits described, the gRNA guide sequences targeting the DNA proximal to the papain or pepsin cleavage site of the IgG1 coding sequence.

In one embodiment of any composition, method, or kits described, the gRNA guide sequences targeting the DNA proximal to the papain or pepsin cleavage site of the heavy chain of the immunoglobulin.

In one embodiment of any composition, method, or kits described, the gRNA guide sequences are GATGCAACAAGTGGCCATGT (SEQ ID NO: 1) and TGTGCTCTTCCTATGCAAAC (SEQ ID NO: 2).

As used herein, the term "immunoglobulin" or "antibody" refers to glycoprotein molecules produced by plasma cells and white blood cells. They act as a critical part of the immune response by specifically recognizing and binding to particular antigens, such as bacteria or viruses and aiding in their destruction. Immunoglobulin is abbreviated as "Ig" and is used interchangeably with antibody. Each Ig molecule consists of four polypeptide chains: two heavy chains (H chains) and two light chains (L chains). There are five antigenically different kinds of H chains, and this difference is the basis for the classification of immunoglobulins. Antibody isotypes are categorized according to differences in their amino acid sequence in the constant region (Fc) of the antibody H chains. The five major classes (as known as isotypes) of Ig in placental mammals based on the Fc regions of the H chains in the molecule: are IgA, IgD, IgE, IgG, and IgM. Each class varies in its chemical structure and in its number of antigen-binding sites and adheres to and reacts only with the specific antigen for which it was produced. Igs are categorized into two main forms: soluble antibodies that are secreted, and surface bound B-cell receptors contains a hydrophobic transmembrane region.

As used herein, the term "immunoglobulin heavy chain locus" or "immunoglobulin heavy chain segment" or "IgH locus" refers to the genomic germline organization of the DNA encoding all the major classes of the Ig heavy chain. The locus includes V (variable), D (diversity), J (joining), and C (constant) DNA segments for the Ig heavy chain polypeptide. During B cell development, a recombination event at the DNA level joins a single D segment with a J segment; this partially rearranged D-J gene is then joined to a V segment. The rearranged V-D-J is then transcribed with the IGHM constant region; this transcript encodes a mu heavy chain. Later in development B cells generate V-D-J-Cmu-Cdelta pre-messenger RNA, which is alternatively spliced to encode either a mu or a delta heavy chain. Mature B cells in the lymph nodes undergo switch recombination, so that the V-D-J gene is brought in proximity to one of the IGHG, IGHA, or IGHE genes and each cell expresses either the gamma, alpha, or epsilon heavy chain. Recombination of many different V segments with several J segments provides a wide range of antigen recognition.

As used herein, the term "IgH chain segment" or "IgH chain gene" when used in the context of inducing CSR of the IgH locus to produce to the IgH chain of the desired subclass, the terms refers to C (constant) DNA segments for the Ig heavy chain polypeptide isotypes, that is, the C DNA for the IgA, IgD, IgE, IgG, and IgM isotypes.

As used herein, the term "upstream" of a gene segment refers to the 5'-end of the gene segment, wherein the gene segment is a DNA.

As used herein, the term "Fab" fragments of an antibody refers to the antigen-binding fragment of an immunoglobulin molecule, containing the variable regions of both light and heavy chains of the Ig molecule.

As used herein, the term "Fc portion" or "Fc binding" or "Fc fragment" of an antibody refers to the constant region of the antibody. It is the crystallizable fragment of an immunoglobulin molecule composed of the constant regions of the heavy chains and is responsible for binding to antibody receptors (Fc receptor) on cells and the C1q component of complement.

As used herein, the term "monoclonal antibody" refers to an antibody produced by a clone or genetically homogeneous population of fused hybrid cells, a hybridoma. All monoclonal antibodies produced from the same clone are identical and have the same antigenic specificity, i.e., have the same Ig isotype, same Fab fragments, and variable regions of both light and heavy chains of the Ig molecule.

As used herein, the term "hybridoma" refers to a hybrid or fusion cell that is produced in the laboratory by fusing an antibody-producing lymphocyte (which does not readily divide) with a non-antibody-producing cancer cell (which divides rapidly). The hybridoma proliferates and produces a continuous supply of a specific monoclonal antibody.

As used herein, the term "lymphocyte" refers to any of the mononuclear non-phagocytic leukocytes found in the blood, lymph, and lymphoid tissues; they comprise the body's immunologically competent cells and their precursors. They are divided on the basis of ontogeny and function into two main classes, B and T lymphocytes, responsible for humoral and cellular immunity, respectively. Most are small lymphocytes 7-10 μm in diameter with a round or slightly indented heterochromatic nucleus that almost fills the entire cell and a thin rim of basophilic cytoplasm that contains few granules. When activated by contact with antigen binding to their cell-surface receptors, small lymphocytes becomes activated and begin macromolecular synthesis, the cytoplasm enlarges until the cells are 10-30 μm in diameter, and the nucleus becomes less completely heterochromatic; they are then referred to as large lymphocytes or lymphoblasts. These cells then proliferate and differentiate into B and T memory cells and into the various effector cell types, B cells into plasma cells, which produces and secretes soluble antibodies, and T cells into helper, cytotoxic, and suppressor cells.

As used herein, the term "B lymphocyte" refers to a type of white blood cell of the lymphocyte subtype that circulates in the blood and lymph, are non thymus-dependent, it is responsible for the production of immunoglobulins, and produces antibodies when it encounters specific antigens. B lymphocytes are also called B cells. They function in the humoral immunity component of the adaptive immune system by secreting antibodies. Additionally, B cells present antigen (they are also classified as professional antigen-presenting cells (APCs)) and secrete cytokines. B lymphocyte can be characterized immunophenotypically by CD19 surface markers. Other B cell markers include CD9, CD10, CD20, CD24, Fc receptor, B1, BA-1, and B4 Ia. In mammals, B cells start out from hematopoietic stem cells in the bone marrow, migrates to the spleen to mature and upon maturation, then move on to the secondary lymphoid organs, such as the spleen and lymph nodes. They are the precursor of the plasma cells and express surface immunoglobulins but does not release them. Prior to encounters specific antigens, they are termed as "naïve" B lymphocytes. Once exposed to an antigen, the naïve B cell is now "activated" and either becomes a memory B cell or a plasma cell that produces and secretes antibodies specific to the antigen that was originally bound, i.e., the antigen that activated the "naïve" B cell. Plasma cells do not last long in the circulation, this is in contrast to memory cells that last for very long periods of time. Memory cells do not secrete antibody until re-activated by their specific antigen again.

As used herein, the term "protospacer-adjacent motif" (PAM) sequence refers to a 2-6 base pair DNA sequence immediately following the DNA sequence targeted by the Cas9 nuclease or nickase in the CRISPR bacterial adaptive immune system. The Clustered Regularly Interspaced Short Palindromic Repeats (CRISPR) and CRISPR Associated (Cas) system was first discovered in bacteria and functions as a defense against foreign DNA, either viral or plasmid. PAM is a component of the invading virus or plasmid, but is not a component of the bacterial CRISPR locus. Cas9 will not successfully bind to or cleave the target DNA sequence if it is not followed by the PAM sequence. PAM is an essential targeting component (not found in bacterial genome), which distinguishes bacterial self from non-self DNA, thereby preventing the CRISPR locus from being targeted and destroyed by nuclease.

As used herein, the term "protospacer" when used in the context of PAM refers to short sequences (-20 bp) of known foreign DNA separated by a short palindromic repeat and kept like a record against future encounters. For a bacterium, the foreign DNA inserted is usually an invading viral or plasmid DNA.

As used herein, the term "comprising" or "comprises" is used in reference to methods, and respective component(s) thereof, that are essential to the invention, yet open to the inclusion of unspecified elements, whether essential or not. The use of "comprising" indicates inclusion rather than limitation.

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "homologous" to another sequence if the two sequences are substantially identical and the functional activity of the sequences is conserved (as used herein, the term "homologous" does not infer evolutionary relatedness, but rather refers to substantial sequence identity). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. For the sake of brevity, the units (e.g., 66, 67 . . . 81, 82, . . . 91, 92% . . . ) have not systematically been recited but are considered, nevertheless, within the scope of the present invention.

As used herein, the term "coding" or "encoding" in the context of a nucleic acid encoding a Cas 9 nuclease or nickase, or gudie RNA means the nucleic acid contains instruction or information therein to specify the genetic code for a endonuclease. The instruction or information in a coding nucleic acid can be transcribe and translated to the encoded protein.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, at least 95%, at least 96%, at least 98% or at least 99%. Optimal alignment of sequences for comparisons of identity may be conducted using a variety of algorithms, such as the local homology algorithm of Smith and Waterman, 1981, Adv. Appl. Math 2: 482, the homology alignment algorithm of Needleman and Wunsch, 1970, J. Mol. Biol. 48:443, the search for similarity method of Pearson and Lipman (62), and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al. (63) 1990 (using the published default settings). Software for performing BLAST analysis may be available through the website of the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M NaHP04, 7% sodium dodecyl sulfate (SDS), 1 mM EDTA at 65° C., and washing in 0.2×SSC/0.1 SDS at 42° C. Alternatively, hybridization to filter-bound sequences under stringent conditions may, for example, be performed in 0.5 M NaHP04, 7% SDS, 1 mM EDTA at 65° C., and washing in 0.1×SSC/0.1 SDS at 68° C. Hybridization conditions may be modified in accordance with known methods depending on the sequence of interest. Generally, stringent conditions are selected to be about 5° C. lower than the thermal melting point for the specific sequence at a defined ionic strength and pH.

As used herein, "identity" means the percentage of identical nucleotide at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ea., Oxford University Press, New York, 1988; Biocomputing: Informatics and –14 Genome Projects, Smith, D. W., ea., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988)). Methods to determine identity are designed to give the largest match between the sequences tested. Moreover, methods to determine identity are codified in publicly available computer programs such as BLASTP.

The terms "identical" or percent "identity", in the context of two or more nucleic acids, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This term also refers to, or can be applied to, the compliment of a test sequence. The term also includes sequences that have deletions and/or additions, as well as those that have substitutions. As described below, the preferred algorithms can account for gaps and the like. In one embodiment, identity exists over a region that is at least about 25 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

As used herein, the term "complementary base pair" or "complementary" refers to A:T and G:C in DNA and A:U in RNA. Most DNA consists of sequences of nucleotide only four nitrogenous bases: base or base adenine (A), thymine (T), guanine (G), and cytosine (C). Together these bases form the genetic alphabet, and long ordered sequences of them contain, in coded form, much of the information present in genes. Most RNA also consists of sequences of only four bases. However, in RNA, thymine is replaced by uridine (U).

The term "nucleic acid" refers to deoxyribonucleotides or ribonucleotides and polymers thereof ("polynucleotides") in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid molecule/polynucleotide also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). Nucleotides are indicated by their bases by the following standard abbreviations: adenine (A), cytosine (C), thymine (T), and guanine (G).

As used herein, the term "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA, ribosomal DNA and cDNA. Other suitable nucleic acid molecules are RNA, including mRNA, rRNA and tRNA. The nucleic acid molecule can be naturally occurring, as in genomic DNA, or it may be synthetic, ie., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

As used herein, the term "vector" as used herein, refers to a nucleic acid construct designed for delivery to a host cell or transfer between different host cells. As used herein, a vector can be viral or non-viral. In one embodiment, the term "vector" refers broadly to any plasmid, phagemid or virus encoding an exogenous nucleic acid. In another embodiment, the term is also be construed to include non-plasmid, non-phagemid and non-viral compounds which facilitate the transfer of nucleic acid into virions or cells, such as, for example, poly-lysine compounds and the like. The vector may be a viral vector that is suitable as a delivery vehicle for delivery of the nucleic acid, or mutant thereof, to a cell, or the vector may be a non-viral vector that is suitable for the same purpose. Examples of viral and non-viral vectors for delivery of DNA to cells and tissues are well known in the art and are described, for example, in Ma et al. (1997, Proc. Natl. Acad. Sci. U.S.A. 94: 12744-12746). Examples of viral vectors include, but are not limited to, a recombinant Vaccinia virus, a recombinant adenovirus, a recombinant retrovirus, a recombinant adeno-associated virus, a recombinant avian pox virus, and the like (Cranage et al., 1986, EMBO J. 5: 3057-3063; International Patent Application No. WO94/17810, published Aug. 18,1994; International Patent Application No. WO94/23744, published Oct. 27, 1994). Examples of non-viral vectors include, but are not limited to, liposomes, polyamine derivatives of DNA, and the like.

As used herein, the term "viral vector" is used according to its art-recognized meaning. It refers to a nucleic acid vector construct that includes at least one element of viral origin and may be packaged into a viral vector particle. The vector may be utilized for the purpose of transferring DNA, RNA or other nucleic acids into cells either in vitro or in vivo. Numerous forms of viral vectors are known in the art.

As used herein, the term "lentiviral vector" refers to a vector having a nucleic acid vector construct that includes at least one element of lentivirus origin.

As used herein, the term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes, i.e., T-cells.

The term "contacting" or "contact" as used herein in connection with contacting a cell includes subjecting the cell to an appropriate culture media which comprises the indicated composition.

The present invention can be defined in any of the following numbered paragraphs:

[1] A composition for directing class switch recombination (CSR) of an immunoglobulin heavy (IgH) chain in a mammalian cell to a desired IgH subclass, the composition comprising a vector comprising a nucleic acid encoding a Cas9 nuclease or nickase and nucleic acids encoding at least two guide RNAs (gRNA).

[2] The composition of paragraph 1, wherein each of the at least two gRNAs comprises a guide sequence that comprises a seed region of at least 10 consecutive nucleotides of a target sequence in a IgH gene polynucleotide sequence present in the cell or at least 10 consecutive nucleotides complementary to a target sequence in a IgH gene polynucleotide sequence present in the cell, and a Cas9 recognition sequence, wherein the target sequence of the gRNA guide sequence is contiguous to a protospacer adjacent motif (PAM) in the IgH gene polynucleotide sequence and wherein the PAM is recognized by a ribonucleoprotein complex comprising a Cas9 nuclease or nickase.

[3] The composition of paragraph 1 or 2, wherein the Cas9 nuclease or nickase is a hSpCas9 nuclease, a hSaCas9 nuclease, a hSpCas9 nickase, a hSaCas9 nickase or a dCas9-FokI nuclease.

[4] The composition of paragraph 2, or 3, wherein the PAM motif that is contiguous with the gRNA guide sequence is located at the 3'-end of the gRNA.

[5] The composition of paragraph 2, 3, or 4, wherein the PAM motif that is contiguous with the gRNA guide sequence is a three nucleotide motif, -NGG-, wherein N is any nucleotide, (A, T, G, or C; adenine=A, cytosine=C, guanine=G, thymine=T) and G is guanine.

[6] The composition of any one of paragraphs 2-5, wherein the target sequence of the gRNA guide sequence is within a switch (S) region which is upstream from a gene segment/nucleic acid sequence that encode a constant region of an antibody heavy chain.

[7] The composition of any one of paragraphs 2-6, wherein the target sequence of the gRNA guide sequence flanks an S region.

[8] The composition of any one of paragraphs 2-7, wherein the target sequence of the gRNA guide sequence flanks a gene segment/nucleic acid sequence that encode a constant region of an antibody heavy chain (aka an exon constant region gene segment in the IgH gene).

[9] The composition of paragraph 8, wherein the exon constant region gene segment in the IgH gene is selected from the group consisting of μ, δ,γ, α, or ε.

[10] The composition of paragraph 9, wherein the exon constant region gene segment in the IgH gene is selected from the group consisting of μ (for IgM), δ (for IgD), γ3 (for IgG3), γ1 (for IgG1), α1 (for IgA1), γ2 (for IgG2), γ4 (for IgG4), ε (for IgE), and α2 (for IgA2).

[11] The composition of any one of paragraphs 1-10, wherein the gRNA comprises a guide sequence or seed sequence that is selected from Table 1 and Table 4 and Table 5 or the the gRNA comprises a guide sequence or seed sequence that is complementary to a sequence selected from Table 1 and Table 4 and Table 5.

[12] The composition of any one of paragraphs 1-11, wherein the desired IgH subclass is selected from the group consisting of IgA1, IgA2, IgM, IgE, IgD, IgG1, IgG2, and IgG3 and IgG4.

[13] The composition of any one of paragraphs 1-12, wherein the vector is a lentivirus or a retrovirus.

[14] A method for directing class switch recombination (CSR) of the immunoglobulin heavy (IgH) chain locus in a mammalian cell to a desired IgH subclass comprising contacting the mammalian cell with a composition of any one of paragraphs 1-13.

[15] A method for directing class switch recombination (CSR) of the immunoglobulin heavy (IgH) chain in a mammalian cell to a desired IgH subclass comprising contacting the mammalian cell with a vector comprising a nucleic acid encoding a Cas9 nuclease or nickase and nucleic acids encoding at least two guide RNAs (gRNA), or contacting with a composition comprising said vector.

[16] The method of paragraph 15, wherein the guide RNA (gRNA) comprises guide sequences that comprising a seed region of at least 10 consecutive nucleotides of a target sequence in the IgH gene polynucleotide sequence present in the cell and a Cas9 recognition sequence or at least 10 consecutive nucleotides complementary to a target sequence in a IgH gene polynucleotide sequence present in the cell, wherein the target sequence of the gRNA guide sequence is contiguous to a protospacer adjacent motif (PAM) in the IgH gene polynucleotide sequence and wherein said PAM is recognized by a ribonucleoprotein complex comprising a Cas9 nuclease or nickase.

[17] The method of paragraph 15 or 16, wherein the Cas9 nuclease or nickase is a hSpCas9 nuclease, a hSaCas9 nuclease, a hSpCas9 nickase, a hSaCas9 nickase or a dCas9-FokI nuclease.

[18] The method of paragraph 15, 16 or 17, wherein the PAM motif that is contiguous with the gRNA guide sequence is located at the 3'-end of the gRNA.

[19] The method of paragraph 15, 16, 17 or 18, wherein the PAM motif that is contiguous with the gRNA is a three nucleotide motif, -NGG-, wherein N is any nucleotide, (A, T, G, or C; adenine=A, cytosine=C, guanine=G, thymine=T) and G is guanine.

[20] The method of any one of paragraphs 16-19, wherein the target sequence of the gRNA guide sequence is within a switch (S) region which is upstream from a gene segment/nucleic acid sequence that encode a constant region of an antibody heavy chain.

[21] The method of any one of paragraphs 16-20, wherein the target sequence of the gRNA guide sequence flanks an S region.

[22] The method of any one of paragraphs 16-21, wherein the target sequence of the gRNA guide sequence flanks a gene segment/nucleic acid sequence that encode a constant region of an antibody heavy chain (aka an exon constant region gene segment in the IgH gene).

[23] The method of paragraph 22, wherein the exon constant region gene segment in the IgH gene is selected from the group consisting of μ, δ,γ, α, or ε.

[24] The method of paragraph 23, wherein the exon constant region gene segment in the IgH gene is selected from the group consisting of μ (for IgM), δ (for IgD), γ3 (for IgG3), γ1 (for IgG1), α1 (for IgA1), γ2 (for IgG2), γ4 (for IgG4), ε (for IgE), and α2 (for IgA2).

[25] The method of any one of paragraphs 15-24, wherein the gRNA guide sequence is selected a guide sequence from Table 1 and Table 4 and Table 5 or the gRNA guide sequence is complementary to a sequence selected from Table 1 and Table 4 and Table 5.

[26] The method of any one of paragraphs 14-25, wherein the mammalian cell is a B lymphocyte or a hybridoma.

[27] The method of paragraph 26, wherein the B lymphocyte is a naïve or activated B lymphocyte, wherein the B lymphocyte is a mammalian B lymphocyte. For example, the mammals can be human, mouse, guinea pig, rat, or rabbit.

[28] The method of any one of paragraphs 14-27, wherein the desired IgH subclass is selected from the group consisting of IgA1, IgA2, IgM, IgE, IgD, IgG1, IgG2, and IgG3 and IgG4.

[29] The method of any one of paragraphs 15-28, wherein the vector is a lentivirus or a retrovirus.

[30] The method of any one of paragraphs 15-29, wherein the vector expresses the Cas9 nuclease or nickase and the at least gRNA in vivo in the mammalian cell.

[31] A rapid method of producing monoclonal antibody of a desired IgH subclass or producing a monoclonal Fab fragment, the method comprising: (a) providing a hybridoma clonal cell; and (b) contacting a mammalian cell with a vector comprising a nucleic acid encoding a Cas9 nuclease or nickase and nucleic acids encoding a guide RNA (gRNA).

[32] The rapid method of paragraph 31, wherein the gRNA comprises a guide sequence which comprising a seed region of at least 10 consecutive nucleotides of a target sequence in the IgH gene polynucleotide sequence present in the cell and a Cas9 recognition sequence, wherein the target sequence of the gRNA guide sequence is contiguous to a protospacer adjacent motif (PAM) in the IgH gene polynucleotide sequence and wherein said PAM is recognized by a ribonucleoprotein complex comprising a Cas9 nuclease or nickase.

[33] The rapid method of paragraph 31 or 32, wherein the gRNAs targeting the DNA proximal to the papain cleavage site of the IgG1 coding sequence.

[34] The rapid method of paragraph 31, 32 or 33, wherein the gRNAs each comprises the sequence GATGCAACAAGTGGCCATGT (SEQ ID NO: 1) or TGTGCTCTTCCTATGCAAAC (SEQ ID NO: 2).

[35] A composition comprising a vector comprising a nucleic acid encoding a Cas9 nuclease or nickase and nucleic acids encoding at least two guide RNAs (gRNA) for use in directing class switch recombination (CSR) of an immunoglobulin heavy (IgH) chain in a mammalian cell to a desired IgH subclass.

[36] A composition comprising a vector comprising a nucleic acid encoding a Cas9 nuclease or nickase and nucleic acids encoding at least two guide RNAs (gRNA) for use in rapid method of production of monoclonal antibody of a desired IgH subclass or producing a monoclonal Fab fragment.

This invention is further illustrated by the following example which should not be construed as limiting. The contents of all references cited throughout this application, as well as the FIGS. and table are incorporated herein by reference.

Those skilled in the art will recognize, or be able to ascertain using not more than routine experimentation, many equivalents to the specific embodiments of the invention described herein. Such equivalents are intended to be encompassed by the following claims.

EXAMPLE

Materials and Methods

Animals: Animal experiments were performed under protocol approved by the Institutional Animal Care and Use Committee (IACUC) of Boston Children's Hospital (Protocol #13-01-2295). 129S2 mice (Charles River) and AID-deficient mice, which were kindly provided by Frederick Alt (Boston Children's Hospital), were housed and maintained in the specific pathogen-free facility at Boston Children's Hospital.

Plasmid DNA construction: For SpCas9 expression and generation of guide RNA (gRNA), the 20-nt target sequences were selected to precede a 5'-NGG protospacer-adjacent motif (PAM) sequence. To minimize off-target effects, the CRISPR design tool from Feng Zhang laboratory was used. (E.g., the Broad Institute website at the Massachusetts Institute of Technology, under "crispr period mit period edu backslash"). All gRNA and PAM sequences used in this study are listed in Table 1. Oligonucleotides were purchased from Integrated DNA technology (IDT), annealed and cloned into the BsmBI-BsmBI sites downstream from the human U6 promoter in LentiCRISPR v2 plasmid, which was a gift from Feng Zhang (ADDGENE plasmid #52961). Oligonucleotides used in this study for cloning are listed in Table 2.

Figure 8A:
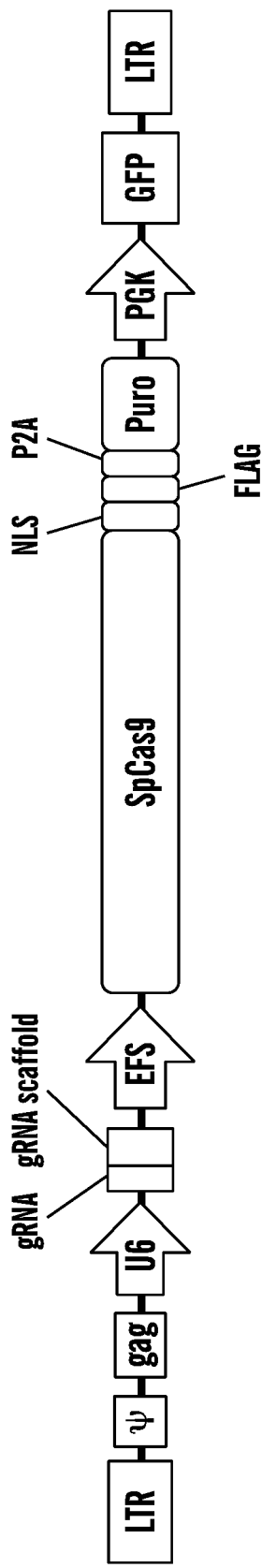
FIGS. 8A-8D. RetroCRISPR vectors and detection of CSR in mouse splenic B cells.
Figure 8B:
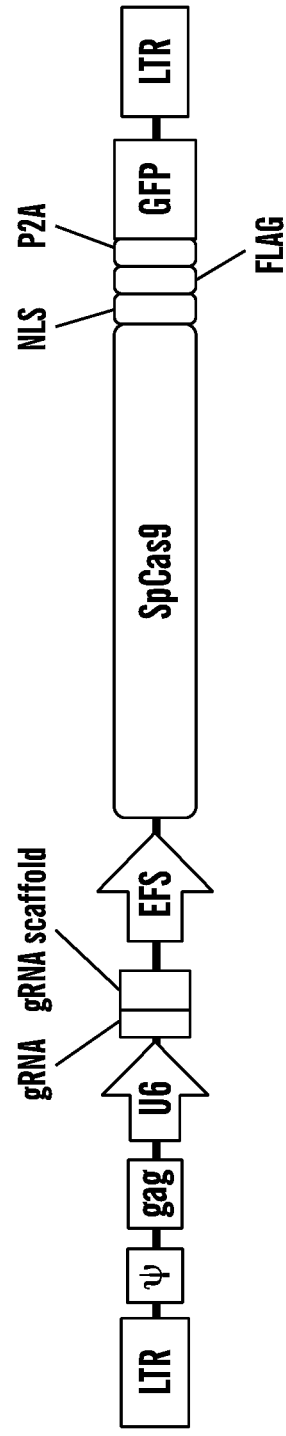

To generate RetroCRISPR v1 plasmid, all gRNAs were first cloned in LentiCRISPR v2 vector. To obtain retroviral backbone, pMSCVgfp::AID plasmid, a gift from Nina Papavasiliou (Addgene plasmid #15925), was digested with XhoI and EcoRI restriction enzymes to remove AID gene, and repaired by Klenow fragment. The constructs harboring the U6 promoter-gRNA-gRNA scaffold-EF1α promoter-SpCas9-NLS-flag-P2A-Puro were obtained from LentiCRISPR v2 vector, and repaired by Klenow fragment. By ligating those two constructs, we generated RetroCRISPR v1 plasmid (FIG. 8A). Since smaller size of plasmid is more efficient to produce retroviral particles, we decided to make a RetroCRISPR v2 plasmid. The construct harboring BamHI-P2A-GFP-ClaI was PCR amplified using pMSCVgfp:AID as a template with forward primer: 5'-TAAG<u>GGATCC</u>GGCGCAACAAACTTCTCTCTG CTGAAACAAGCCGGAGATGTCAAGAGAAT CCTGGACCGGTGAGCAAGGGCGAGGAGCTGTTC-3' (SEQ ID NO: 3) and reverse primer: 5'-TAAG <u>ATCGAT</u>GGCCGCTTTACTTGTACAGCTCGTCCATGC-3' (SEQ ID NO: 4) (The restriction sites, BamHI and ClaI, are underlined). To generate RetroCRISPR v2 plasmid, PCR products were cloned into RetroCRISPR v1 plasmid digested with BamHI and ClaI restriction enzymes (FIG. 8B).

PI3Kδϵ1021K construct cloned in GFP-reporter MIGR1 retroviral vector was a kind gift from Klaus Okkenhaug (The Babraham Institute, Cambridge, UK). As a control, we used GFP-reporter MIGR1 plasmid, which was a gift from Warren Pear (ADDGENE plasmid #27490).

Lenti- and Retro-viral particle productions: HEK293FT cells (Invitrogen), Phoenix-ECO cells, and GP2-293 packaging cell lines were maintained in Dulbecco's modified Eagle's medium (DMEM) supplemented with 10% fetal bovine serum (FBS), 100 units/ml penicillin-streptomycin (P/S), and 2 mM L-Glutamine (L-Glu). Cells were cultured at 37° C. in 5% $CO_2$ atmosphere.

To generate lentiviral particle, $5.5 \times 10^6$ HEK293FT cells were plated per 10 cm dish. The following day, cells were transfected by calcium phosphate transfection method with 7.2 μg of lentiCRISPR plasmid, 3.6 μg of VSVG, 3.6 μg of RSV-REV, and 3.6 μg of PMDLg/pPRE. The media was changed 8 h post-transfection. The viral supernatant was collected 48 h post-transfection, passed through a 0.45 μm filter, pooled and used either fresh or snap frozen.

To generate retroviral particle for mouse B cells, $3.5 \times 10^6$ Phoenix-ECO cells were plated per 10 cm dish. The following day, cells were transfected by calcium phosphate transfection method with 10 μg of retroviral plasmid and 5 μg of pCL-Eco retrovirus packaging plasmid. The media was changed 8 h post-transfection. The viral supernatant was collected 48 h post-transfection, passed through a 0.45 μm filter, pooled and used either fresh or snap frozen.

To generate retroviral particle for human cells, $3.5 \times 10^6$ GP2-293 packaging cells were plated per 10 cm dish. The following day, cells were transfected by Xfect transfection reagent (Clontech) with 10 μg of retroviral plasmid and 5 μg of pVSVG retrovirus envelop plasmid. The media was changed 4 h post-transfection. The viral supernatant was collected 48 h post-transfection, passed through a 0.45 μm filter, pooled and used either fresh or snap frozen.

Cell cultures, transduction, and puromycin selection: Immortalized mouse fibroblast cells were maintained in DMEM supplemented with 10% FBS, 100 units/ml P/S, and 2 mM L-Glu. Cells were cultured at 37° C. in 5% $CO_2$ atmosphere. For transduction, $2 \times 10^4$ cells were plated into six-well plates. The following day, cells were transduced with viral supernatant supplemented with 6 μg/ml polybrene. The viral supernatant was exchanged for fresh medium 6 h later. After 2 days, cells were treated with 6 μg/ml of puromycin to select resistant cells until non-infected cells were completely dead.

Naive B cells were separated from total spleen cell suspensions using α-CD43 magnetic microbeads (Miltenyi). The CD43-negative fraction was cultured with α-CD40 (1 μg/ml; eBioscience) and IL-4 (20 ng/ml; PeproTech) for 4 days. Retrovirus infection was performed 24 h post-activation. Activated-B cells were transduced with viral supernatant supplemented with 6 μg/ml polybrene. The viral supernatant was exchanged for fresh medium containing α-CD40 and IL-4 6 h later.

Hybridomas were generated as previously described15 and cultured in RPMI 1640 medium GlutaMax (Invitrogen) supplemented with 15% FBS and 100 units/ml P/S. Hybridomas were maintained at 37° C. in 5% $CO_2$ atmosphere. For transduction, $2 \times 10^5$ cells were plated into six-well plates and transduced with viral supernatant supplemented with 6 μg/ml polybrene. The viral supernatant was exchanged for fresh medium 6 h later. After 2 days, cells were treated with 3 μg/ml of puromycin to select resistant cells until non-infected cells were completely dead.

All human lymphomas used in this study were cultured and maintained in RPMI 1640 medium supplemented with 10% FBS, 100 units/ml P/S, and 2 mM L-Glu. All cell lines were cultured at 37° C. in 5% $CO_2$ atmosphere. For transduction, $2 \times 10^5$ cells were plated into six-well plates and transduced with viral supernatant supplemented with 6 μg/ml polybrene. The viral supernatant was exchanged for fresh medium 6 h later. After 2 days, cell lines were treated with 0.2 µg/ml of puromycin to select resistant cells until non-infected cells were completely dead. For PI3KδE1021K rescue experiments, JEKO-1 cells were first transduced with lentiviruses to induce deletion between Sµ and Sγ3, cultivated for 5 days and then transduced with GFP-reporter PI3KδE1021K or control MIGR1 retrovirus.

Genomic DNA isolation, PCR, and Sequencing analysis: Mouse fibroblast, hybridomas, and JEKO-1 cells were transduced with lentiviruses, selected with puromycin, and collected after 5 days of transduction. Genomic DNA was extracted using Rapid lysis buffer containing 10 µg/ml Proteinase K by incubating at 56° C. overnight. Primers used for PCR amplifications to detect deletions, inversions, and excision circles from mouse fibroblasts, hybrodomas, or JEKO-1 cells are listed in Table 3. PCR products were gel purified and cloned using pGEM-T easy vector system (Promega). Mutations were identified by Sanger sequencing.

Surveyor assay: The genomic region flanking the CRISPR target sites was PCR amplified (Surveyor primers are listed in Table 3), and products were purified using PCR purification kit (QIAGEN) following the manufacturer's protocol. 400 ng total of the purified PCR products were mixed with 2 µl 10×Taq DNA Polymerase PCR buffer (Life Technologies) and ultrapure water to a final volume of 20 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min. After re-annealing, products were treated with SURVEYOR nuclease and SURVEYOR enhancer S (Transgenomics) following the manufacturer's recommended protocol, and analyzed on 2% high-resolution agarose gel (Sigma Aldrich). Gels were stained with ethidium bromide (Sigma Aldrich) and imaged with a Gel Doc gel imaging system (Bio-rad). Quantification was based on relative band intensities. Indel percentage was determined by the formula, $100 \times (1-(1-(b+c)/(a+b+c))1/2)$, where a is the integrated intensity of the undigested PCR product, and b and c are the integrated intensities of each cleavage products.

Flow cytometry: Mouse B cells and hybridomas were stained with PE-conjugated α-IgG1 antibody (BD Pharmingen) or APC-conjugated α-IgM for 30 min on ice, and analyzed using a FACSVerse flow cytometer (BD Biosciences). IgG1+ cells were gated on GFP. Data were analyzed by FlowJo software.

Human lymphoma cells were co-stained with APC-conjugated α-CD19 and either FITC-conjugated α-IgM or FITC-conjugated α-IgG or FITC-conjugated α-IgA antibodies (MyBioSource) for 30 min on ice to detect IgG or IgA switching, respectively. For simultaneous switching, JEKO-1 cells were transduced with three different lentiviruses indicated in FIG. 14. Cells were co-stained with PE-conjugated α-IgG and FITC-conjugated α-IgA antibodies (MyBioSource) for 30 min on ice. To detect sequential switching, cells were stained with the three following combinations: FITC-conjugated α-IgM and PE-conjugated α-IgG, FITC-conjugated α-IgA and PE-conjugated α-IgG, or PE-conjugated α-IgM and FITC-conjugated α-IgA antibodies (MyBioSource) for 30 min on ice. Cells were analyzed using a FACSVerse flow cytometer (BD biosciences). Data were analyzed by FlowJo software (FlowJo).

Western blot analysis: IgG1—or Fab' fragment-producing hybridomas were cultured in six-well plates ($3 \times 10^6$ cells in 2 ml of HBSS). After 24 hours, supernatants were collected and centrifuged to remove dead cells. For non-reducing condition, supernatants were mixed with loading buffer without reducing reagents. For reducing condition, supernatants were mixed with loading buffer containing β-mercaptoethanol and boiled at 95° C. for 5 min. In both conditions, samples were loaded on 4-15% Mini-PROTEIN TGX gels (BIO-RAD), transferred on nitrocellulose membrane (GE Healthcare), blocked with 5% Skim milk (BIO-RAD), incubated with Rat monoclonal α-mouse kappa light chain (HRP) (clone H139-52.1, Abcam) or Goat polyclonal α-mouse IgG-H&L chain (HRP) (GE Healthcare), and developed with ECL solution (GE Healthcare).

Statistical analysis: Statistical analyses were performed using One-way and Two-way ANOVA with GraphPad Prism 6 software (GraphPad Software). Data are shown as mean+s.e.m.

Results

Figure 1B:
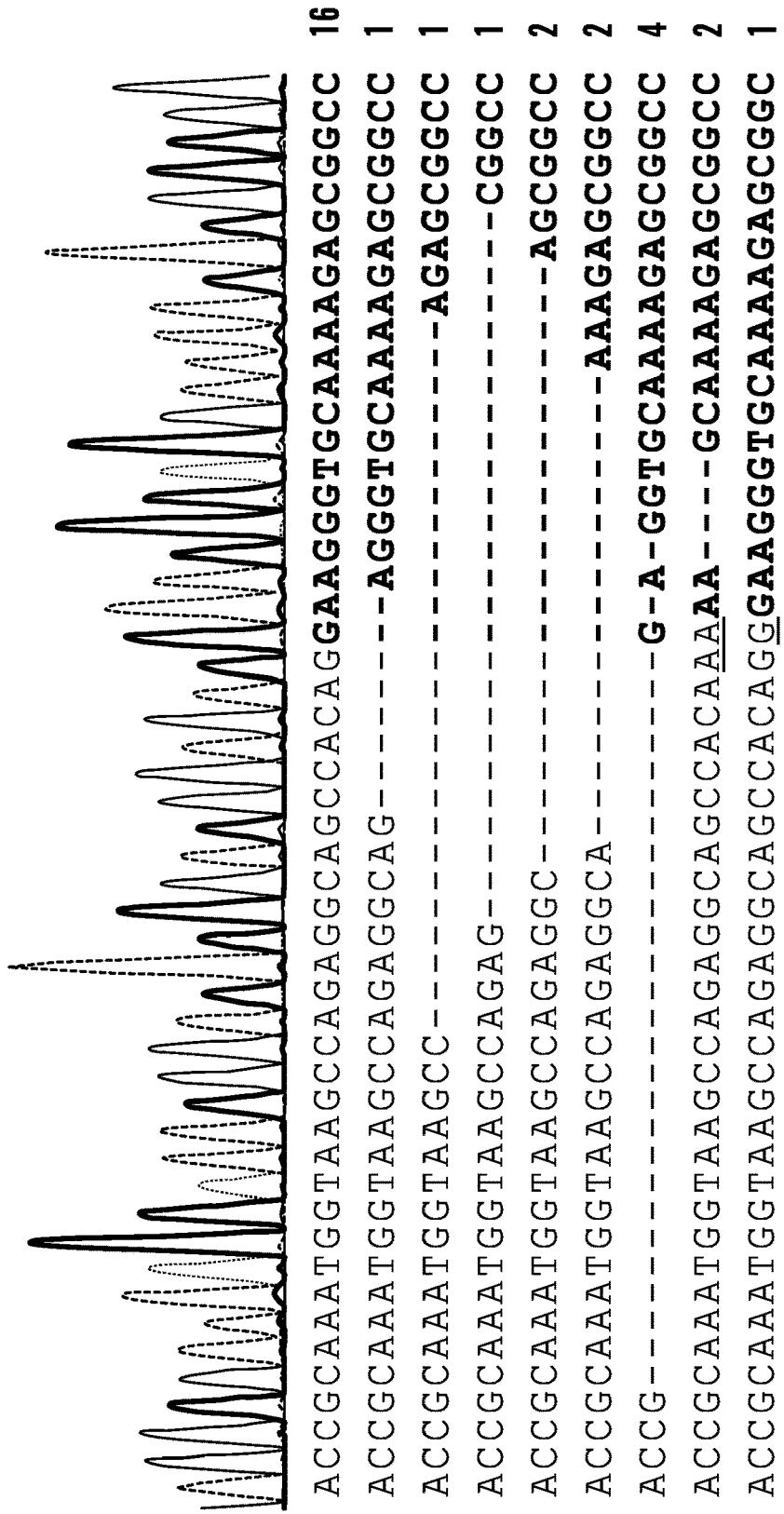
Figure 6A:
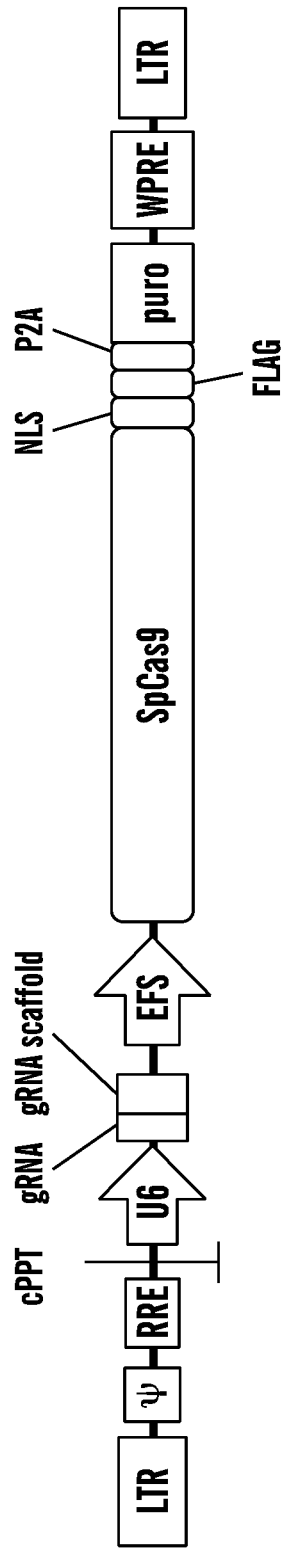
FIGS. 6A-6B. LentiCRISPR v2 vector and surveyor assay
Figure 6B:
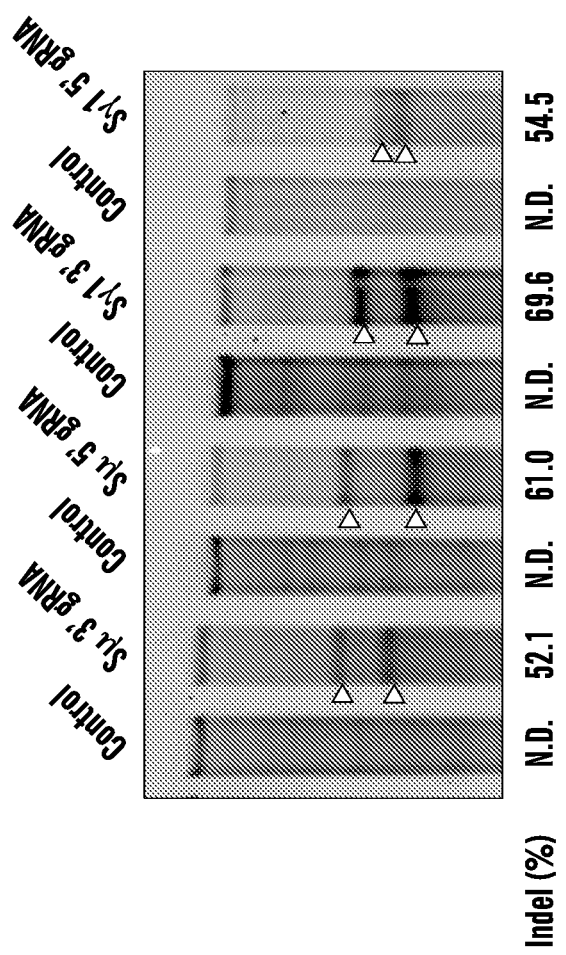
Figure 7A:
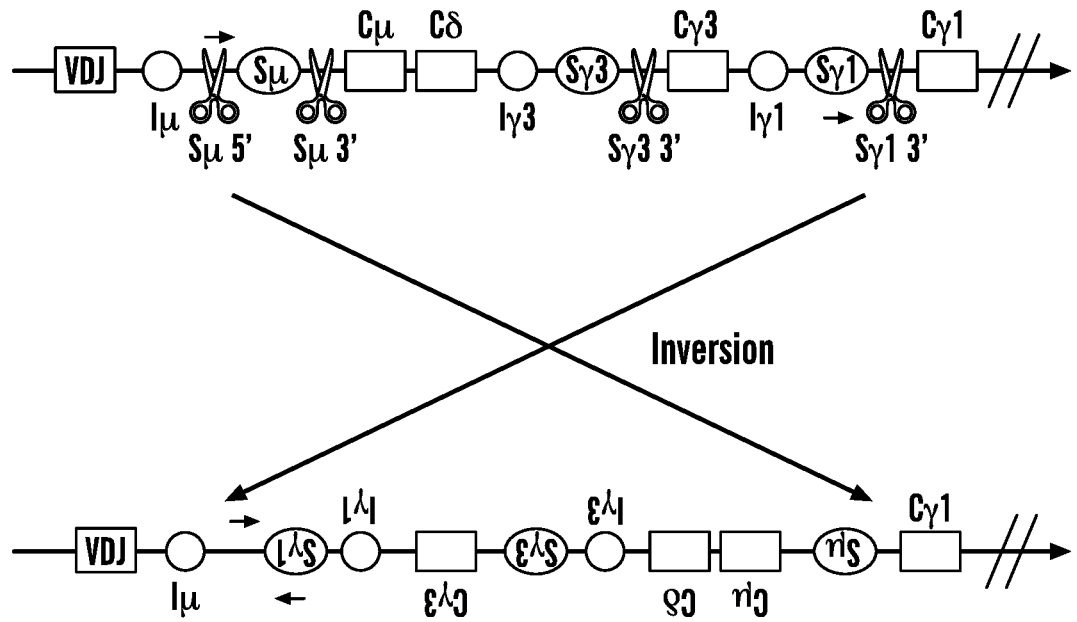
FIGS. 7A-7B. Detection of inversions and excision circles
Figure 7A:
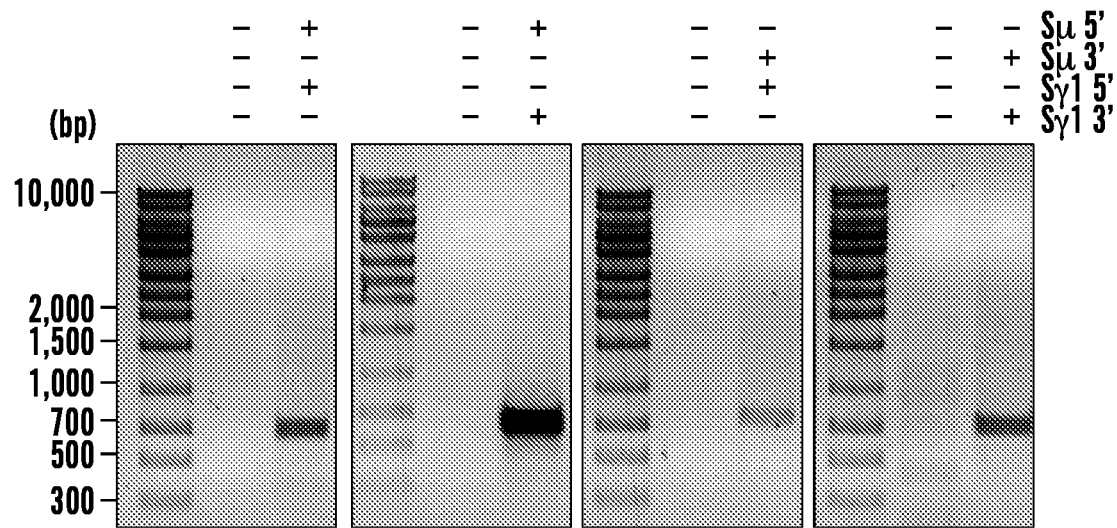
Figure 7B:
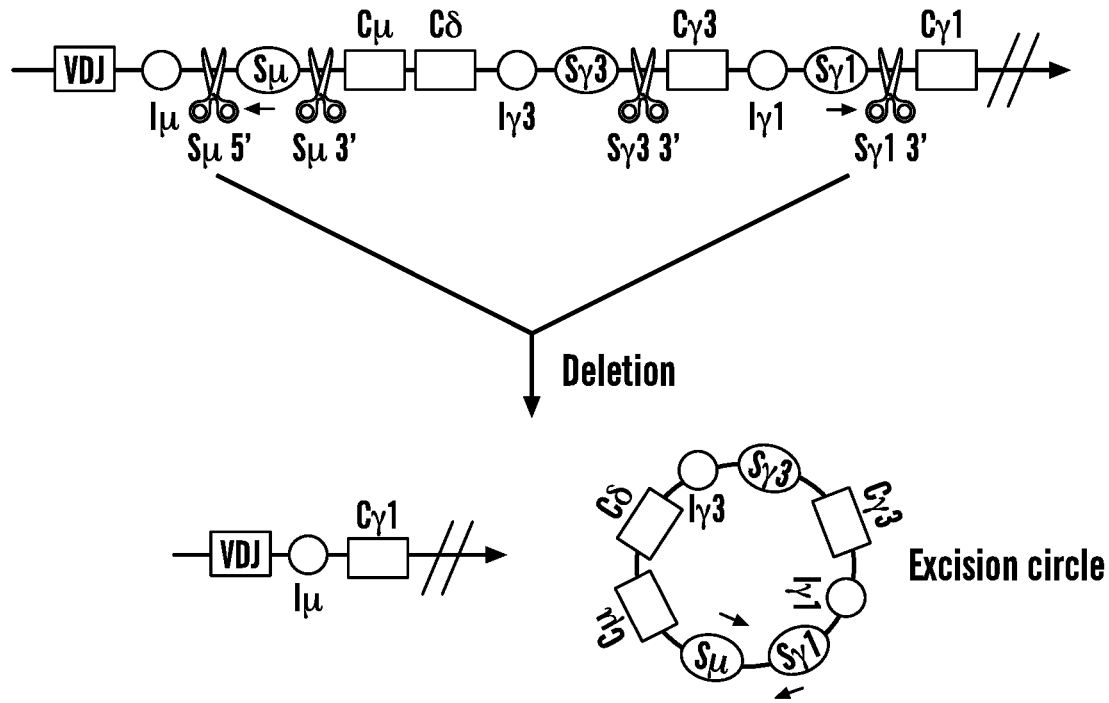
Figure 7B:
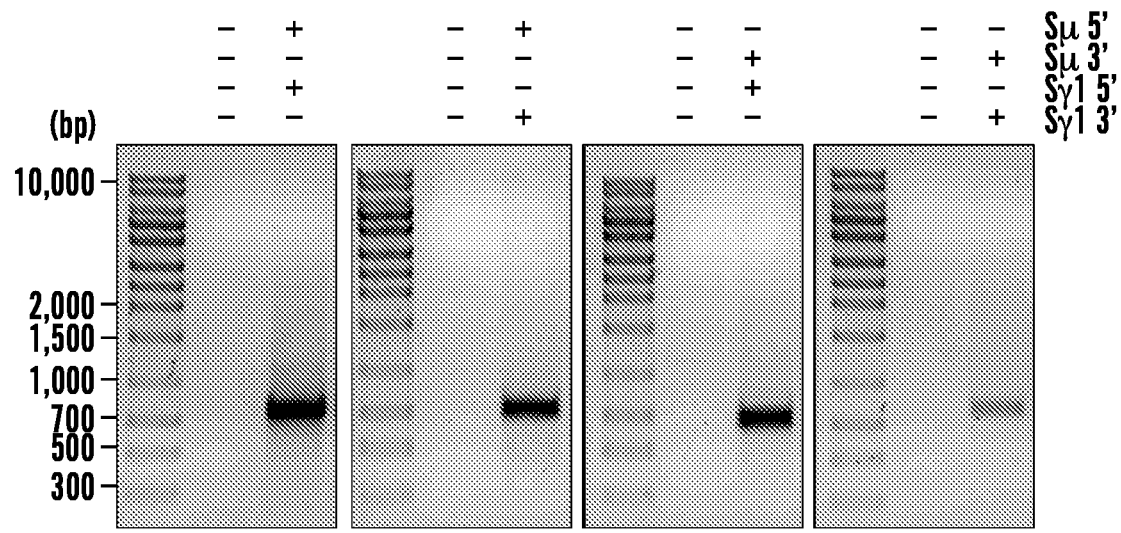

CRISPR/Cas9 mediated class switch recombination (CSR) in mouse B cell. Because CSR is a DNA deletion induced by two DSBs occurring in the S regions preceding the IgH constant sequences, the inventors sought to engineer CSR by CRISPR/Cas9-mediated DNA deletion. The inventors first designed a system to target the mouse IgH locus. Given that S regions are highly repetitive, the inventors generated lentiviral vectors expressing Cas9 and guide-RNA (gRNA) targeting the more specific DNA sequences flanking immediately upstream (Sµ 5' gRNA and Sγ1 5' gRNA) or downstream (Sµ 3' gRNA and Sγ1 3' gRNA) of the S regions that precede the mouse Cµ and Cγ1 IgH constant sequences (FIG. 1A and FIG. 6A). Efficiency of selected gRNA sequences was tested by Surveyor assay (FIG. 6B). By introducing simultaneous DSBs in sites flanking the Sµ and Sγ1 regions, the prediction was to generate deletions of the DNA segment encompassed by the two DSBs as well as excision circles in a process closely mimicking CSR occurring in B cells 5. To test this prediction, the inventors first transduced immortalized mouse fibroblasts. PCRs with specific primers confirmed that the expected deletions were obtained with all four gRNA combinations (FIG. 1A). Sanger sequencing of PCR products demonstrated not only the expected DNA junctions with a predominance of precise junctions between the Cas9 mediated DSBs, but also 5' or 3' deletions and insertions, as previously described 11-14 (FIG. 1B). PCR also detected the expected excision circles as well as inversions of the DNA segment encompassed by the DSBs, as the inventors previously demonstrated in a different model 13 (FIG. 7A-7B).

Figure 1C:
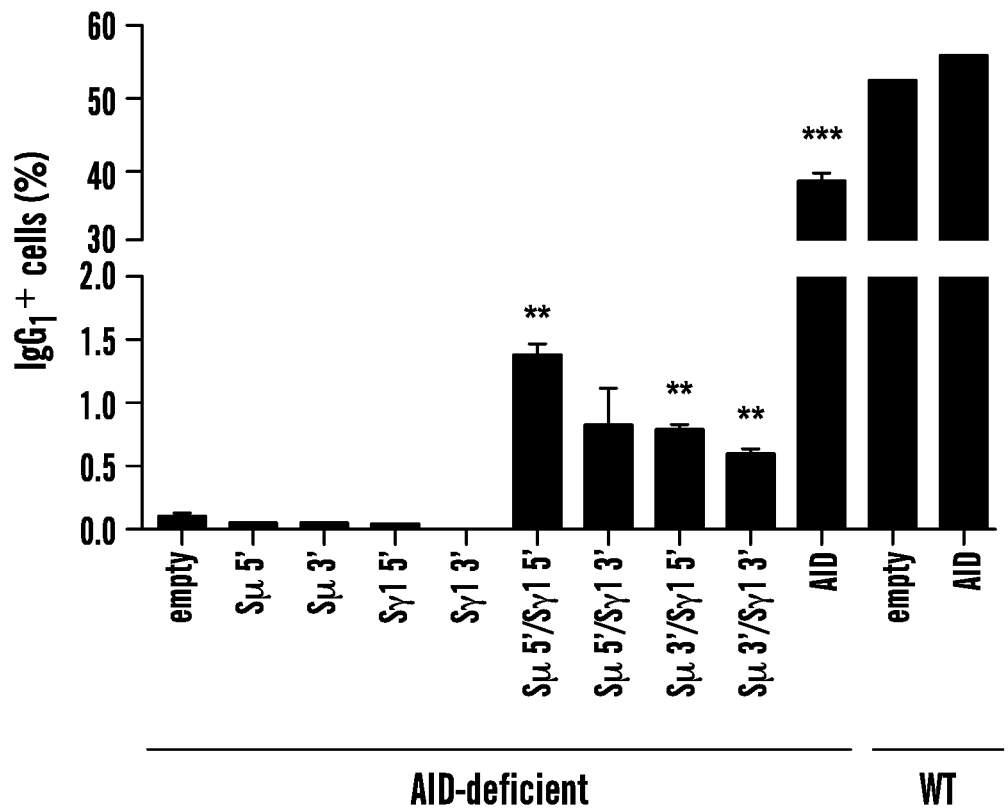
Figure 8C:
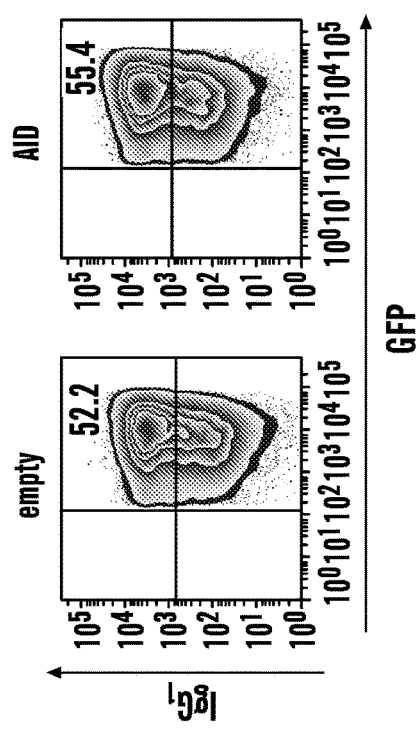
Figure 8D:
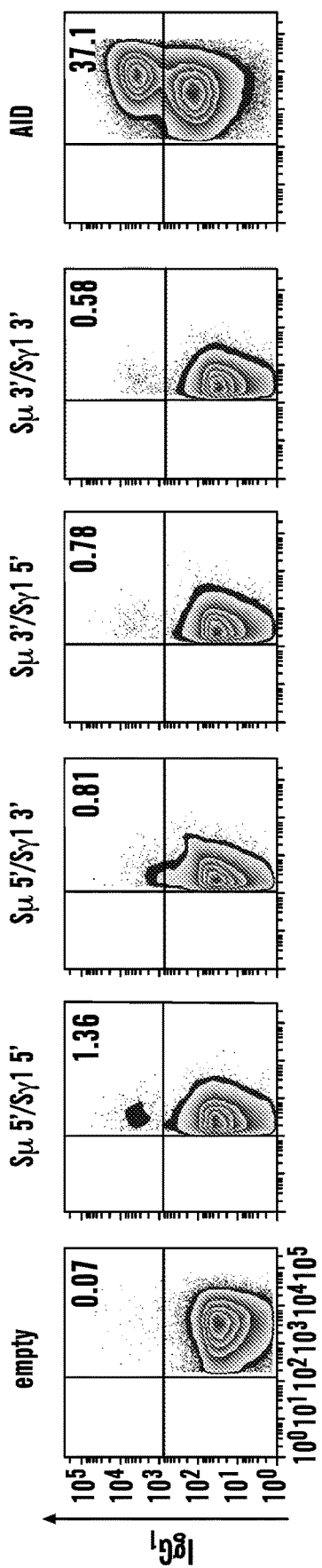

Next the inventors sought to induce CSR in primary mouse B cells. When activated in vitro by anti-CD40 antibody and IL4, mouse B cells typically are induced to high levels of CSR (FIG. 8C)[15], impairing a precise assessment of CSR induced by the CRISPR/Cas9 system. Thus, we decided to exploit AID-deficient B cells in which CSR is practically undetectable [15]. Since retroviruses are more efficient to transduce primary B cells than lentiviruses, the inventors generated a retroviral vector that expressed Cas9 and the same gRNA used in fibroblasts (FIGS. 8A-8B). Remarkably, with all four Cas9-gRNA combinations, the inventors observed a small but distinct population of AID-deficient B cells that switched from IgM to IgG1 (FIG. 1C and FIG. 8D). The overall frequency of 1% CSR was in line with previous reports describing chromosomal translocations induced by CRISPR/Cas9[11]-14.

Figure 1D:
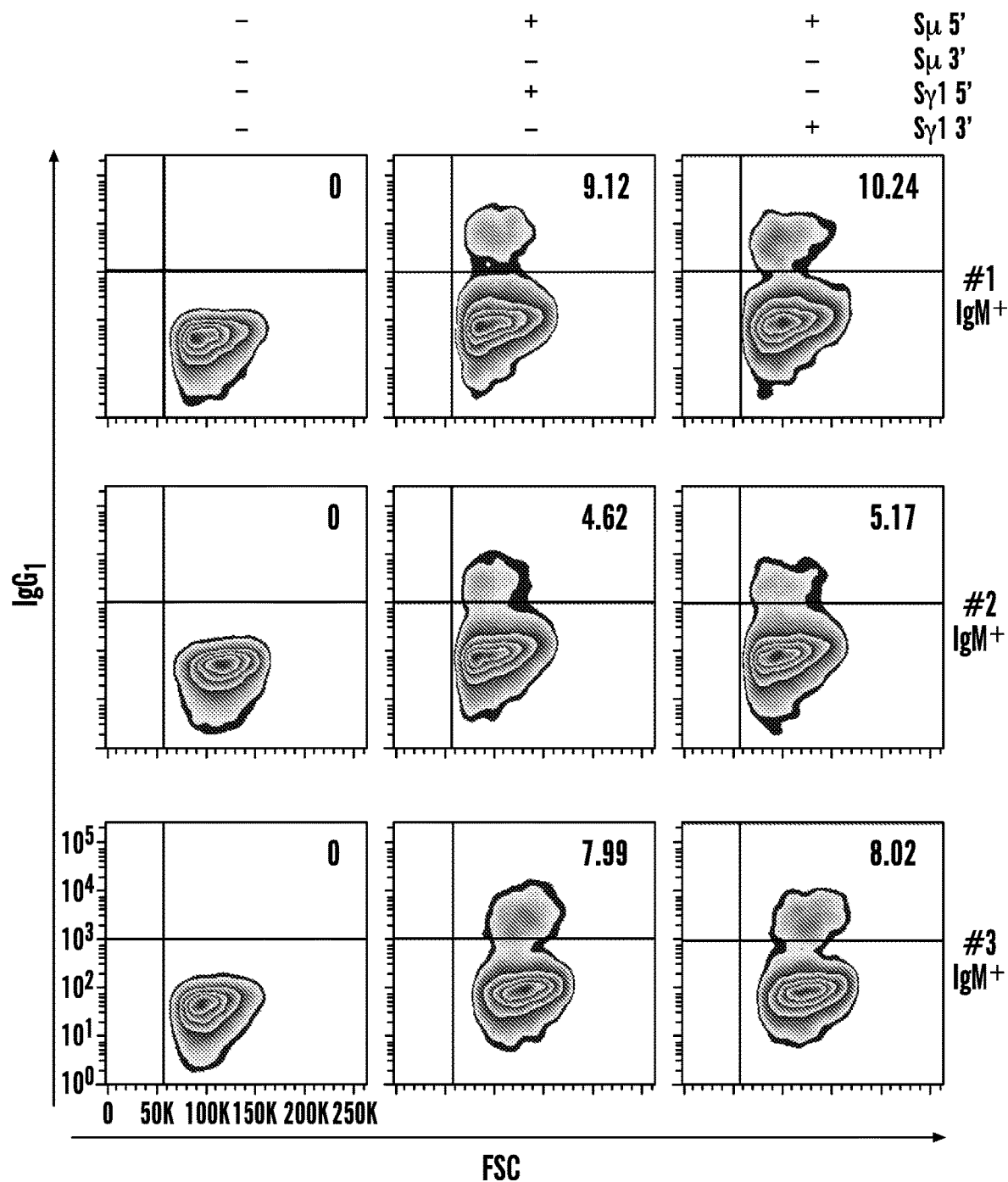
Figure 1D:
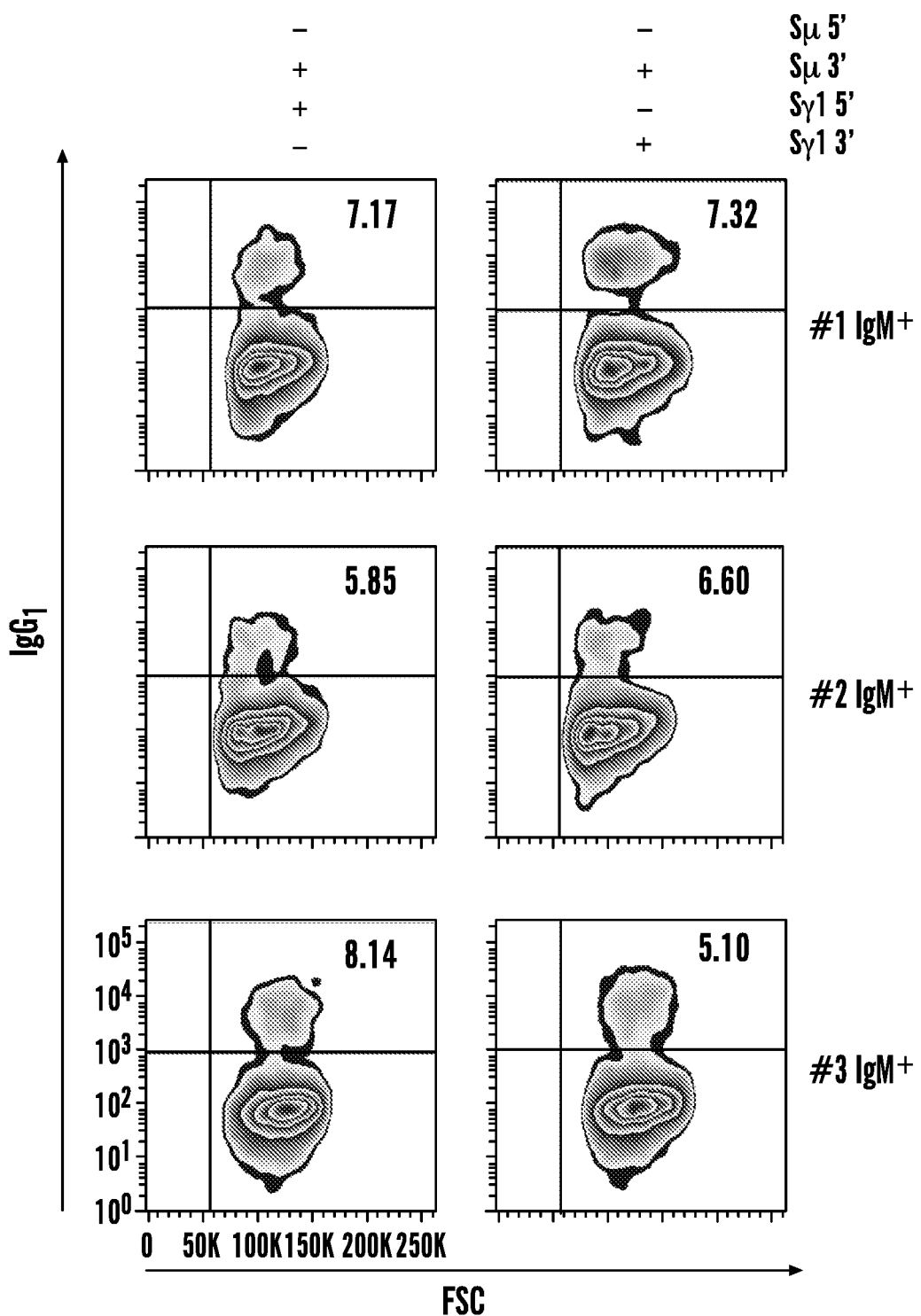
Figure 1E:
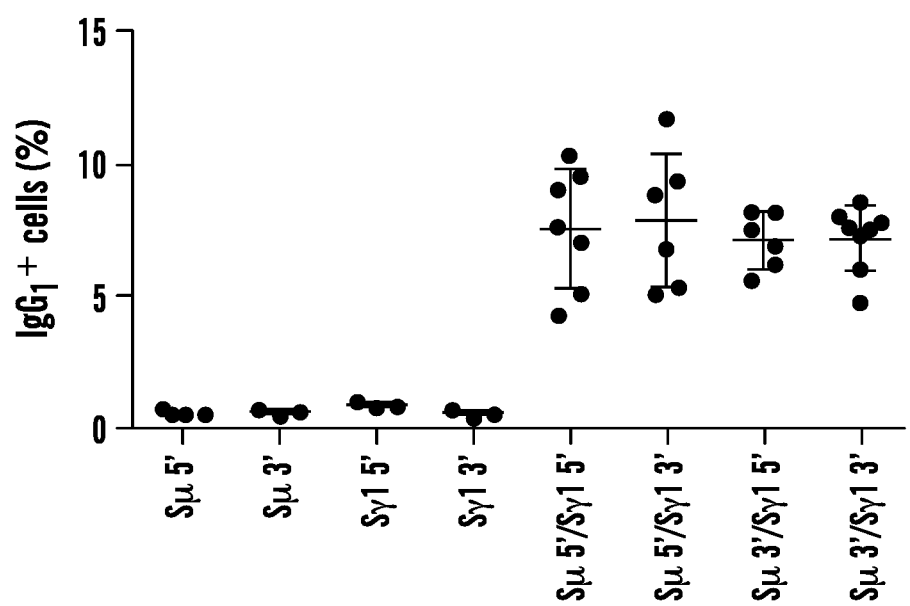
Figure 9:
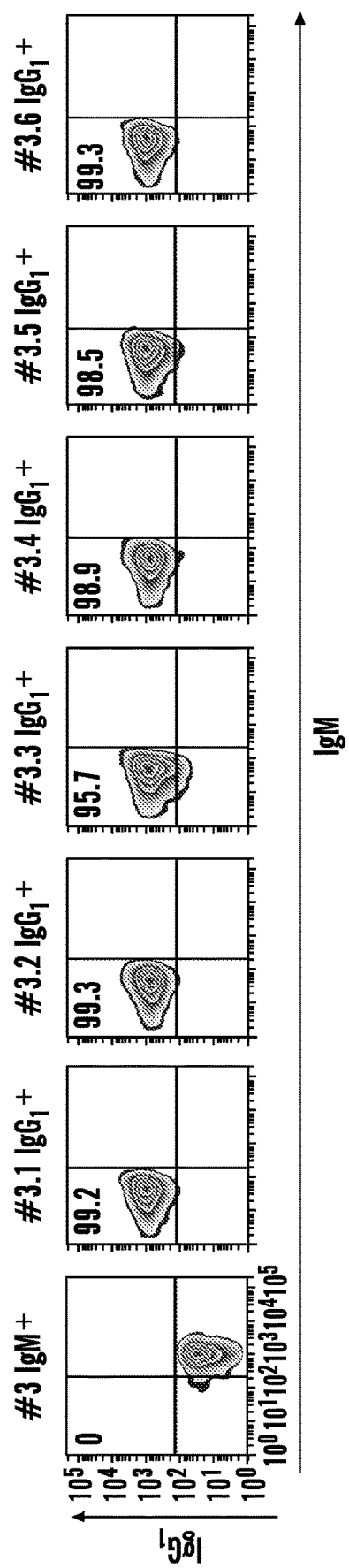
FIG. 9. Examples of CSR in hybridomas. Hybridoma #3 IgM+ from FIG. 1D was transduced with four different combinations of lentiviruses expressing Cas9 nuclease and gRNAs used in FIG. 1A and selected with puromycin (3 µg/ml) for 3 days. Live cells were seeded in 96-well plates to isolate single cell clones, stained with IgG1 and IgM antibodies, and analyzed by flow cytometry. Data were analyzed by FlowJo software. Out of 189 hybridomas, 12 were IgG1-positive pure clones. Representative zebra plots from six different IgG1-positive pure clones are presented. Percentages of events are indicated in the corresponding quadrant.

CRISPR/Cas9 mediated CSR in mouse hybridoma cells. To further validate the efficiency of the CRISPR/Cas9 system to induce CSR in mouse cells, the inventors transduced IgM+ hybridoma cells. Surprisingly, higher levels of CSR than in primary B cells were observed in all hybridomas tested with all gRNA combinations (range 4% to 11%) (FIGS. 1D-1E). Remarkably, similar levels of CSR were observed when the entire Sµ and Sγ regions were conserved (Sμ 3' gRNA with Sγ1 5' gRNA) or deleted (Sμ 5' gRNA with Sγ1 3' gRNA) (FIGS. 1A, 1D-1E). By single cell cloning, the inventors isolated pure IgG1 hybridomas at the expected frequency (12 pure IgG1 clones out of 189 total clones: 6.3%) (FIG. 9). Overall, these results from primary mouse B cells and hybridomas showed that CSR can be achieved at high frequency by CRISPR/Cas9 system, and that hybridoma can be engineered to switch to the desired IgH subclass. Importantly, according to the described strategy, CSR edited hybridoma will retain the same V(D)J coding sequence (FIG. 1A). Thus, this technology could be readily used to generate hybridoma with the same antigen specificity but different IgH subclass. This would represent an important application for antibody production because different IgH subclasses (for example IgG1 vs IgG4) are known to have different affinity for the Fc receptor, potency in complement activation, biological properties in terms of half-life and tissue diffusion, as well different biochemical properties[16].

Figure 2A:
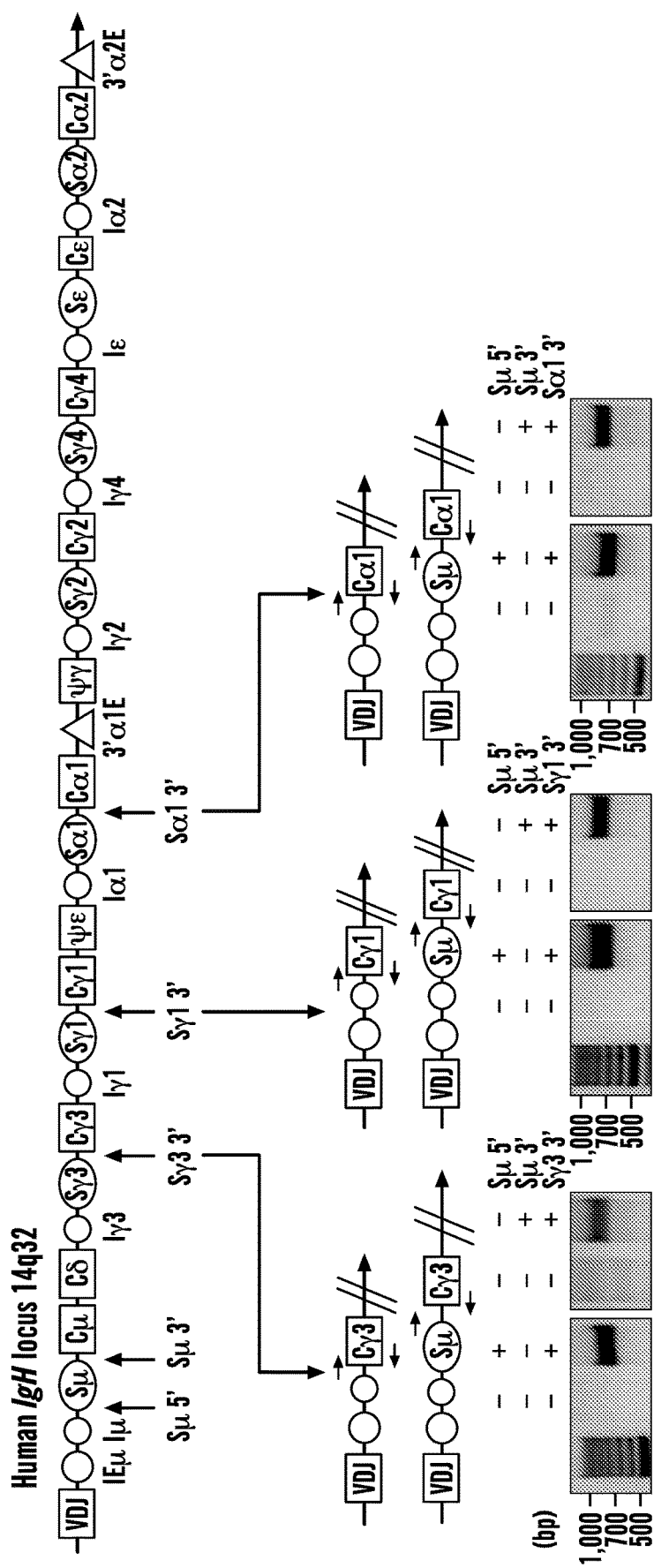
FIG. 2A-2D. Induction of CSR by CRISPR/Cas9 system in human B cell lines
Figure 2B:
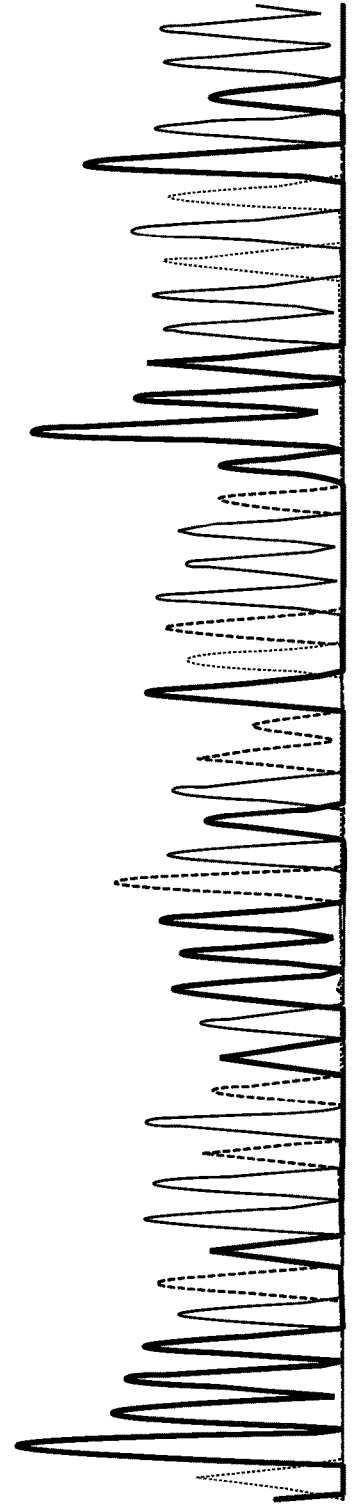
Figure 2C:
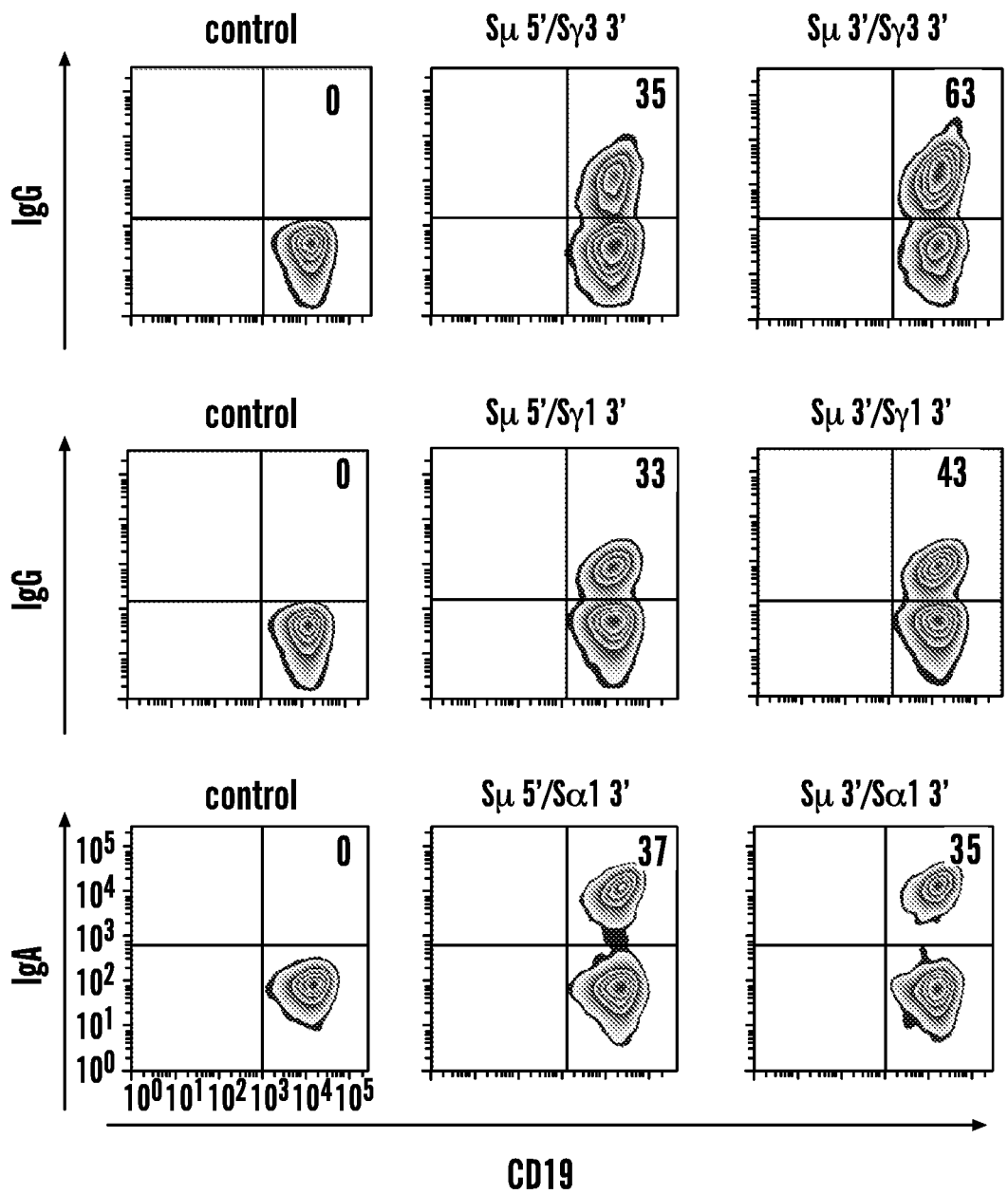
Figure 3:
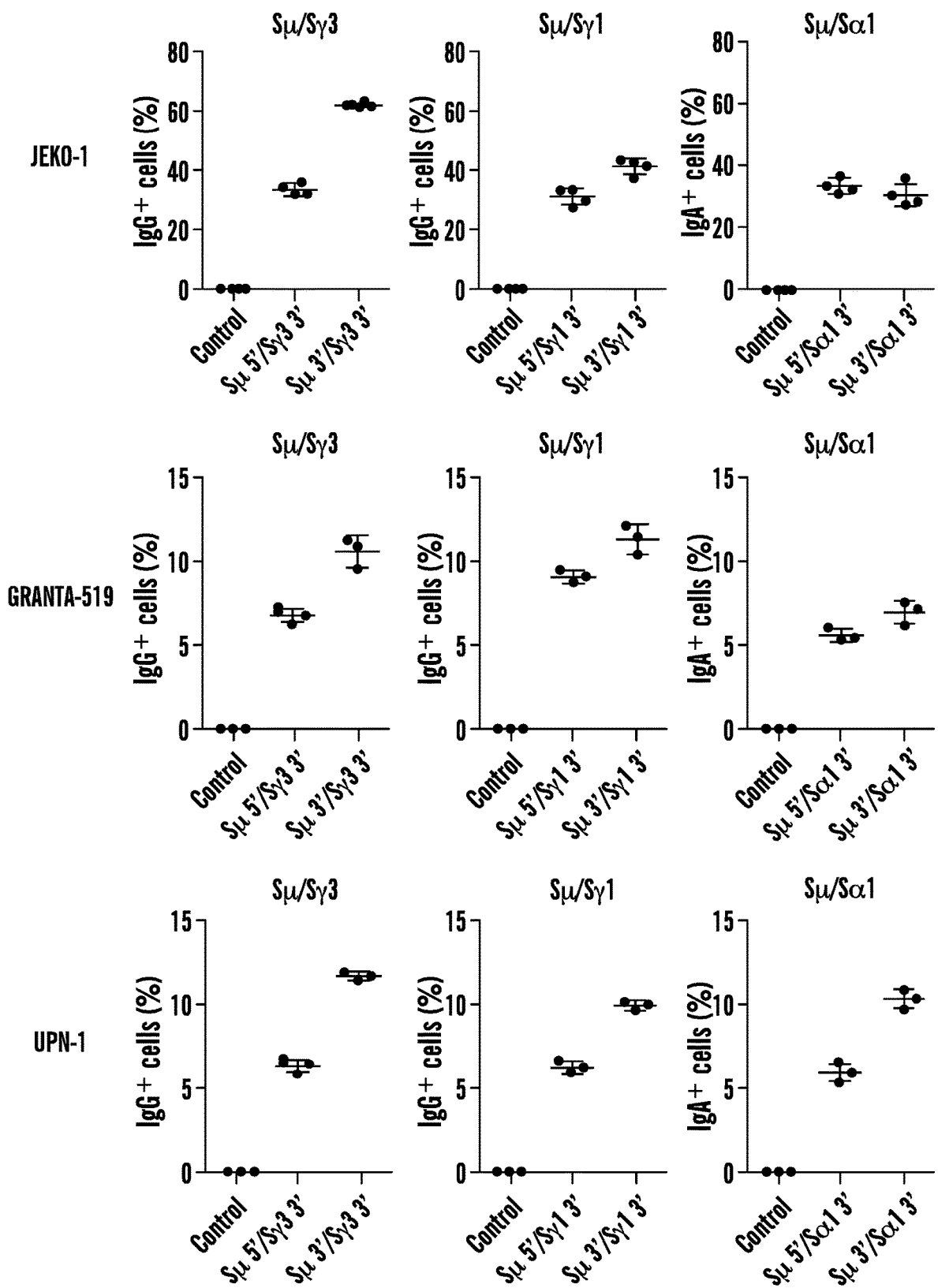
FIG. 3. CSR in a panel of human B cell lymphoma lines. Ten different human B cell lymphoma lines (JEKO-1, GRANTA-519, UPN-1, UPN-2, MAVER-1, MINO, Z138, BL-41, BJAB, and MEC-1) were transduced with lentiviruses expressing Cas9 nuclease and gRNAs targeting Sµ and Sγ3, Sγ1, or Sα1 flanking regions. Two days later, cell lines were selected with puromycin (0.2 µg/ml) for 3 days. Live cells were collected, co-stained with CD19 and IgG or IgA antibodies, and analyzed by flow cytometry. As a control, non-transduced or single lentivirus-transduced cells were used. Data were analyzed by FlowJo software. Mean±SD; n=3.
Figure 3:
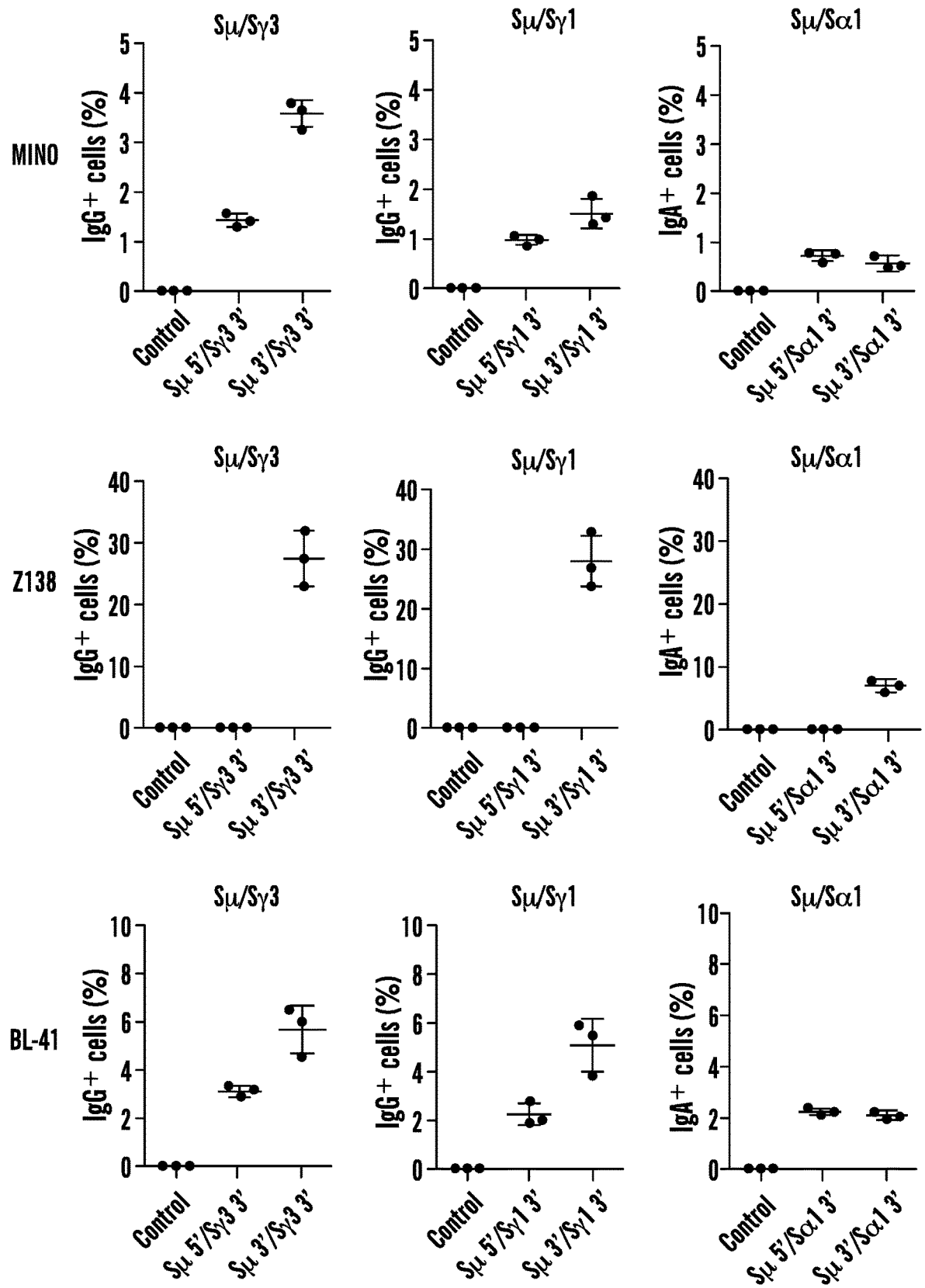
Figure 3:
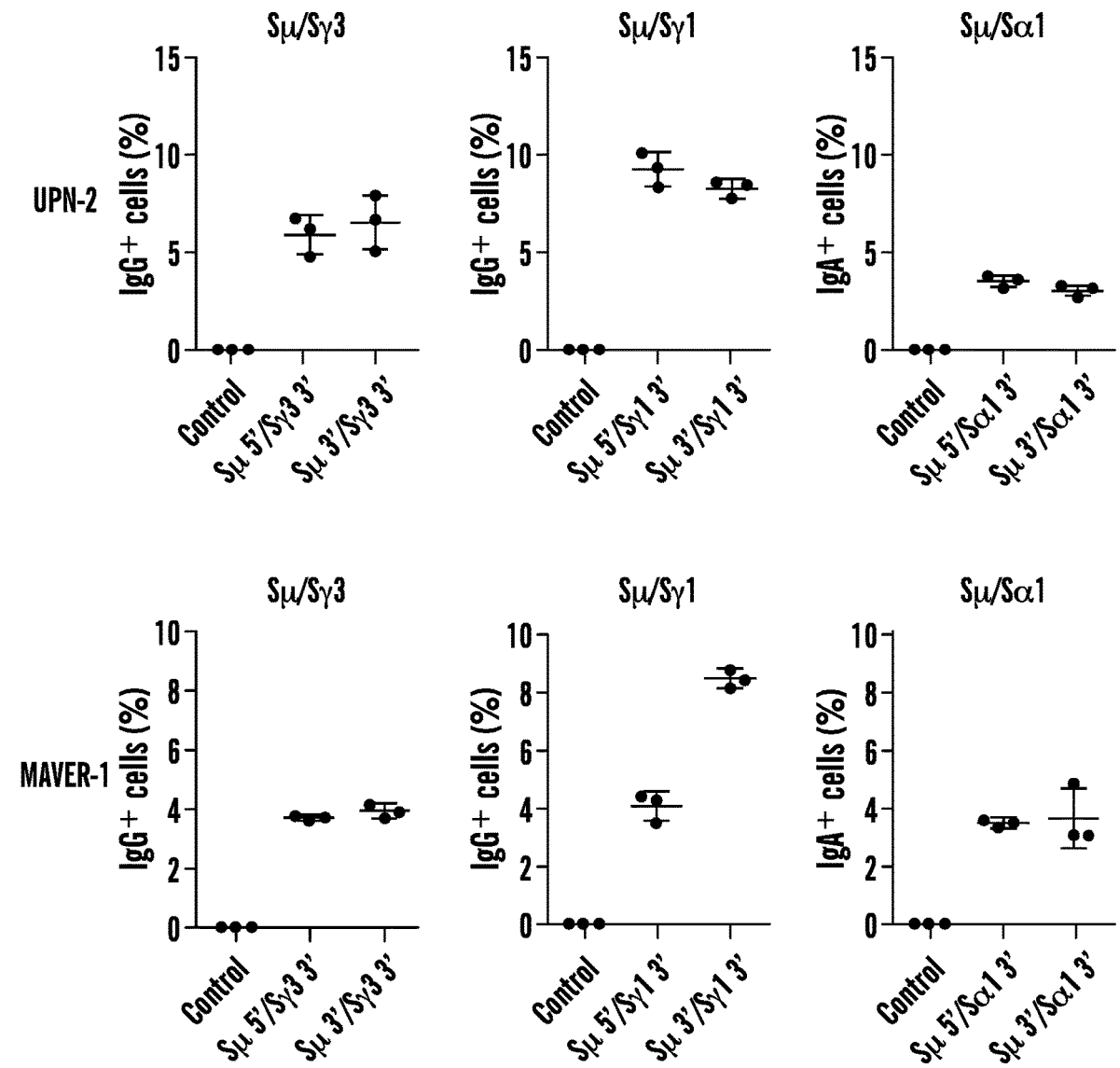
Figure 3:
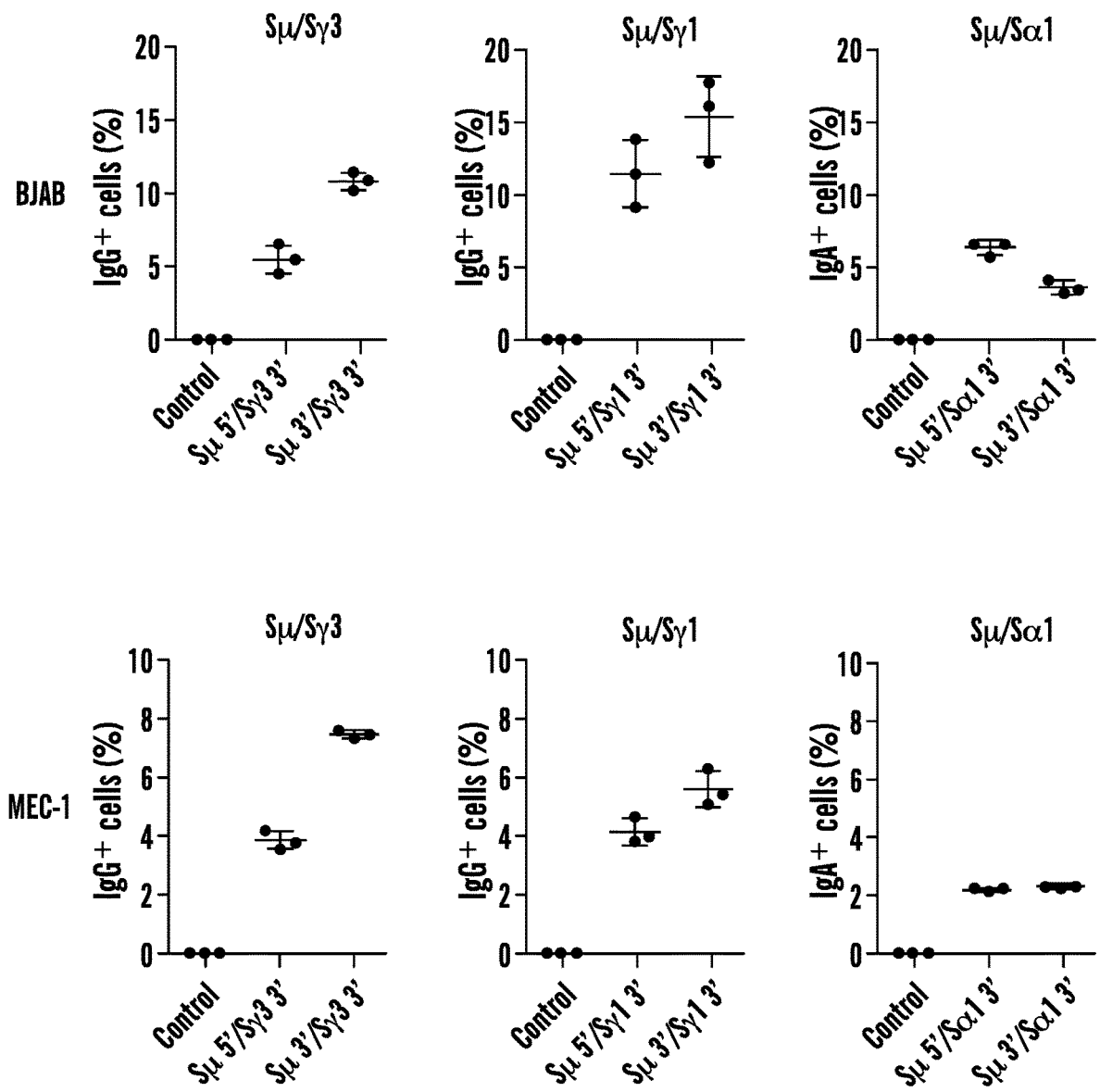
Figure 10:
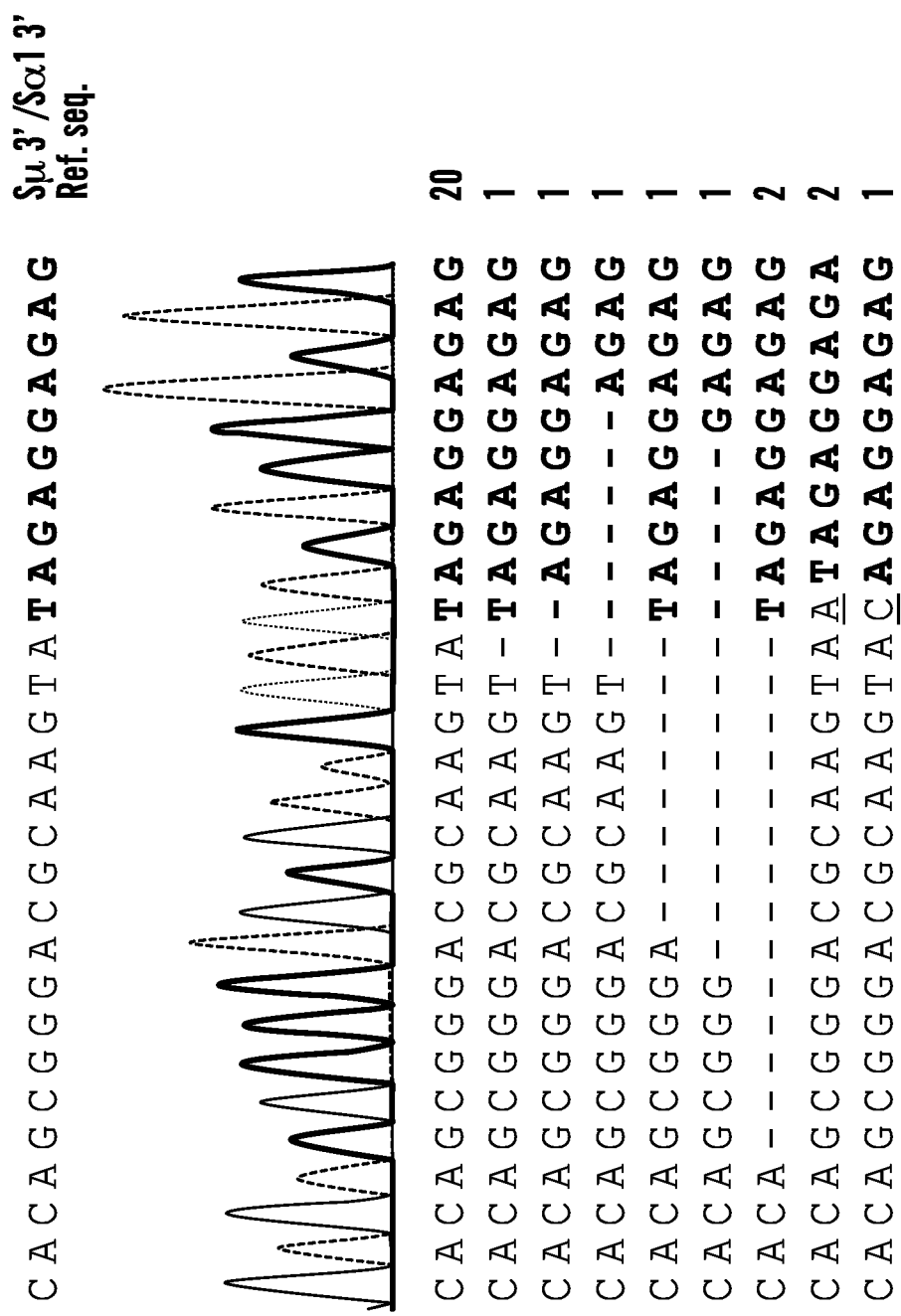
FIG. 10. Examples of Sanger sequencing of the splice junction between Sµ and Sα flanking regions. Representative sequences of junctions identified from 30 clones for Sµ 3' and Sα1 3' genomic region. PCR products were purified and cloned into pGEM-T vector. Ref. Seq. is the sequence of the predicted genomic junction between Sµ 3' and Sal 3' region. Bold sequence represent downstream sequence of the Sα1 3' region. Non-bold regular sequence represent upstream sequence of the Sµ 3' region. Underlined bases are base insertions created during the CSR; Dashes are deleted bases created during the CSR. Figure discloses SEQ ID NOS 419 and 419-427, respectively, in order of appearance.
Figure 11:
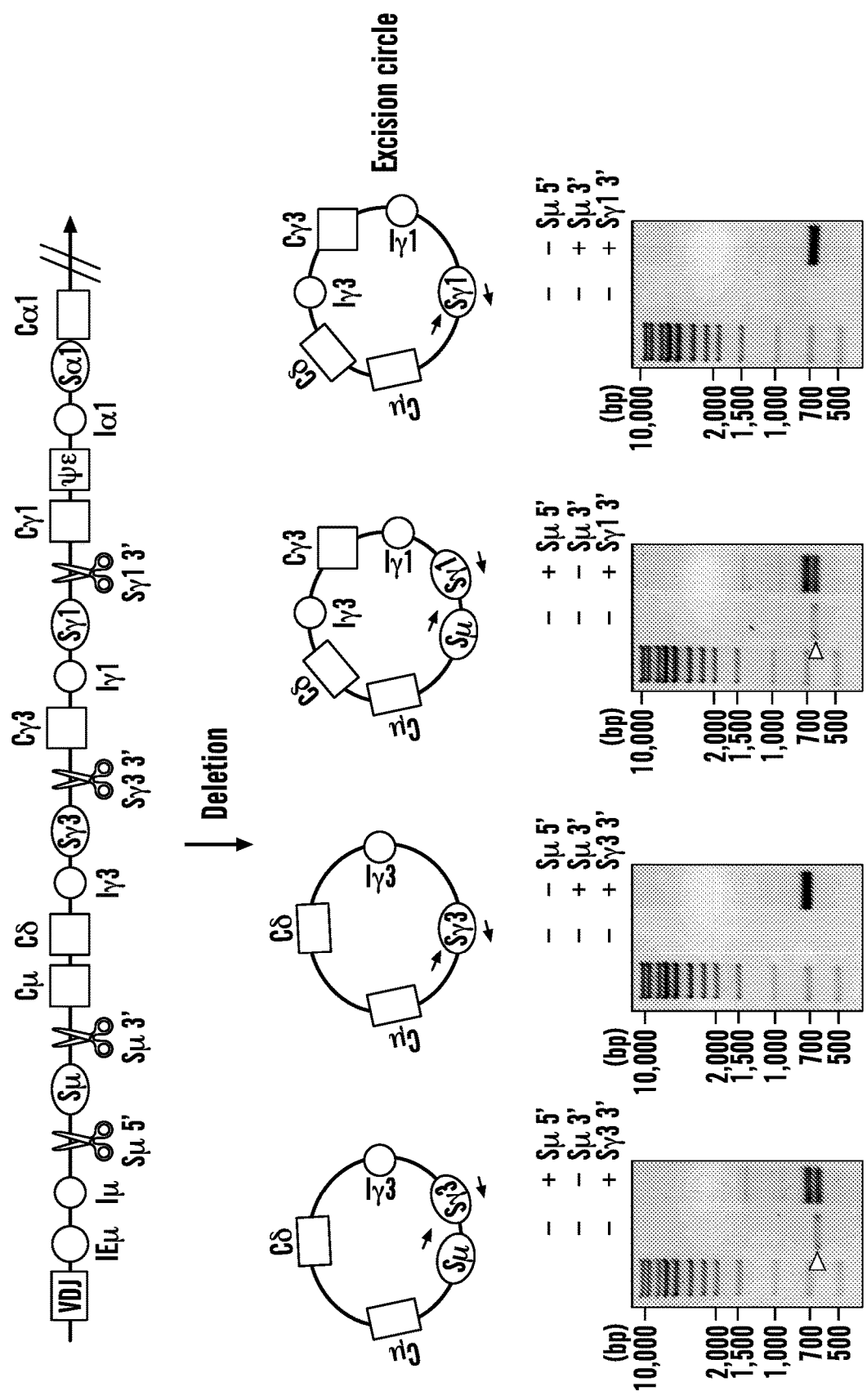
FIG. 11. Detection of excision circles in JEKO-1 cells. Schematic overview of excision circles generated with four different combinations of gRNA targeting Sµ and Sγ3 or Sγ1 flanking regions. Black arrows indicate primers used for PCR. Cutting sites are indicated with scissors. Open white arrowheads in the gels indicate non-specific band.
Figure 12A:
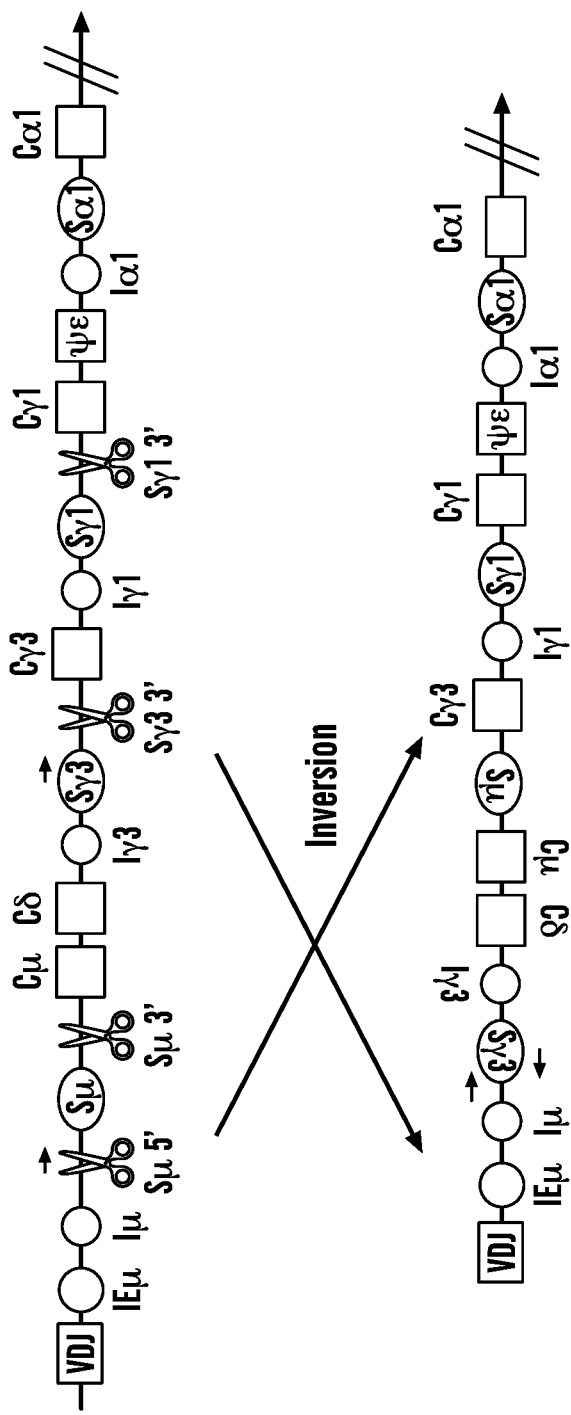
FIGS. 12A-12B. Detection of inversions in JEKO-1 cells.
Figure 12B:
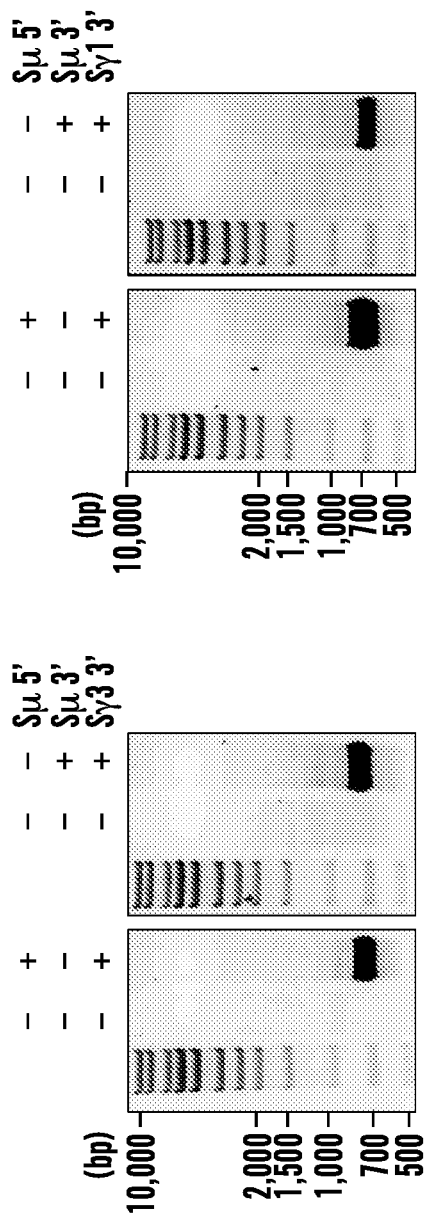
Figure 13:
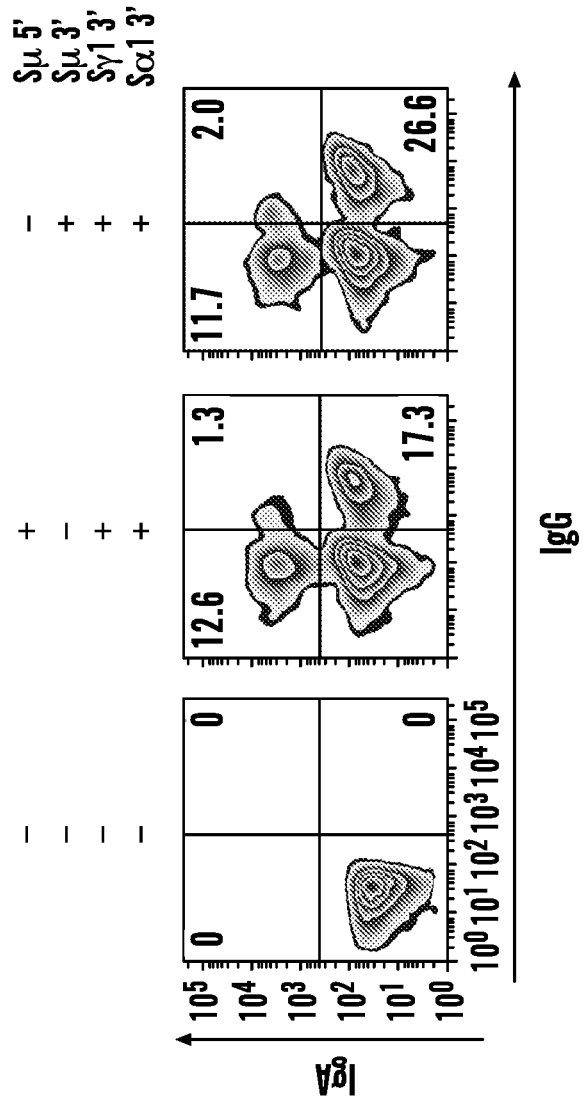
FIG. 13. Simultaneous CSR switching in JEKO-1 cells. To induce simultaneous class switching from IgM to IgG or IgA, IgM-expressing JEKO-1 cells were co-transduced with three lentiviruses expressing Cas9 nuclease and gRNAs targeting Sµ, Sγ1 3', and Sα1 3' flanking regions. Two days later, cells were selected with puromycin (0.2 µg/ml). At day 7, cells were collected, co-stained with antibodies IgM, IgG, or IgA, and analyzed by flow cytometry. Data were analyzed by FlowJo software. Representative zebra plots from one of three independent experiments are presented. Percentages of events are indicated in the corresponding quadrants.

CRISPR/Cas9 mediated CSR in human B cells. To investigate whether engineering of CSR could be efficiently achieved also in human B cells, the inventors designed Cas9-gRNA lentiviral vectors to target the regions flanking the human Sμ (Sμ 5' gRNA and Sμ 3' gRNA), Sγ3 (Sγ3 3' gRNA), Sγ1 (Sγ1 3' gRNA) and Sα1 (Sα1 3' gRNA) regions (FIG. 2a). The inventors selected a panel of IgM+human lymphoma cell lines that included mantle cell lymphoma (JEKO-1, GRANTA-519, UPN-1, UPN-2, MAVER-1, MINO and Z138), Burkitt lymphoma (BL-41 and BJAB) and chronic lymphocytic leukemia (MEC-1). As shown in mouse B cells, deletion junctions were readily identified in all combinations tested and Sanger sequencing confirmed a prevalence of direct junctions over deletions and insertions (FIG. 2B and FIG. 10). Excision circles and inversions were detected as well (FIGS. 11 and 12). Remarkably, high levels of CSR were observed in each cell line tested ranging from 1% (MINO) to 60% (JEKO-1), with an average of 10% (FIG. 2C and FIG. 3). The only lentivirus that did not induce CSR was Sμ 5' gRNA in Z138 cell line. When the inventors sequenced the DNA of Z138 corresponding to the gRNA target region, the inventors found a small deletion encompassing the Sμ 5' gRNA targeted site (data not shown), thus explaining why this gRNA combination failed to induce CSR. When the inventors transduced B lymphoma cells with three gRNAs targeting the flanking regions of Sμ, Sγ1 and Sα, the inventors simultaneously obtained IgG1+ and IgA+ cells from the original IgM+ cells at comparable frequency (FIG. 13).

Figure 2D:
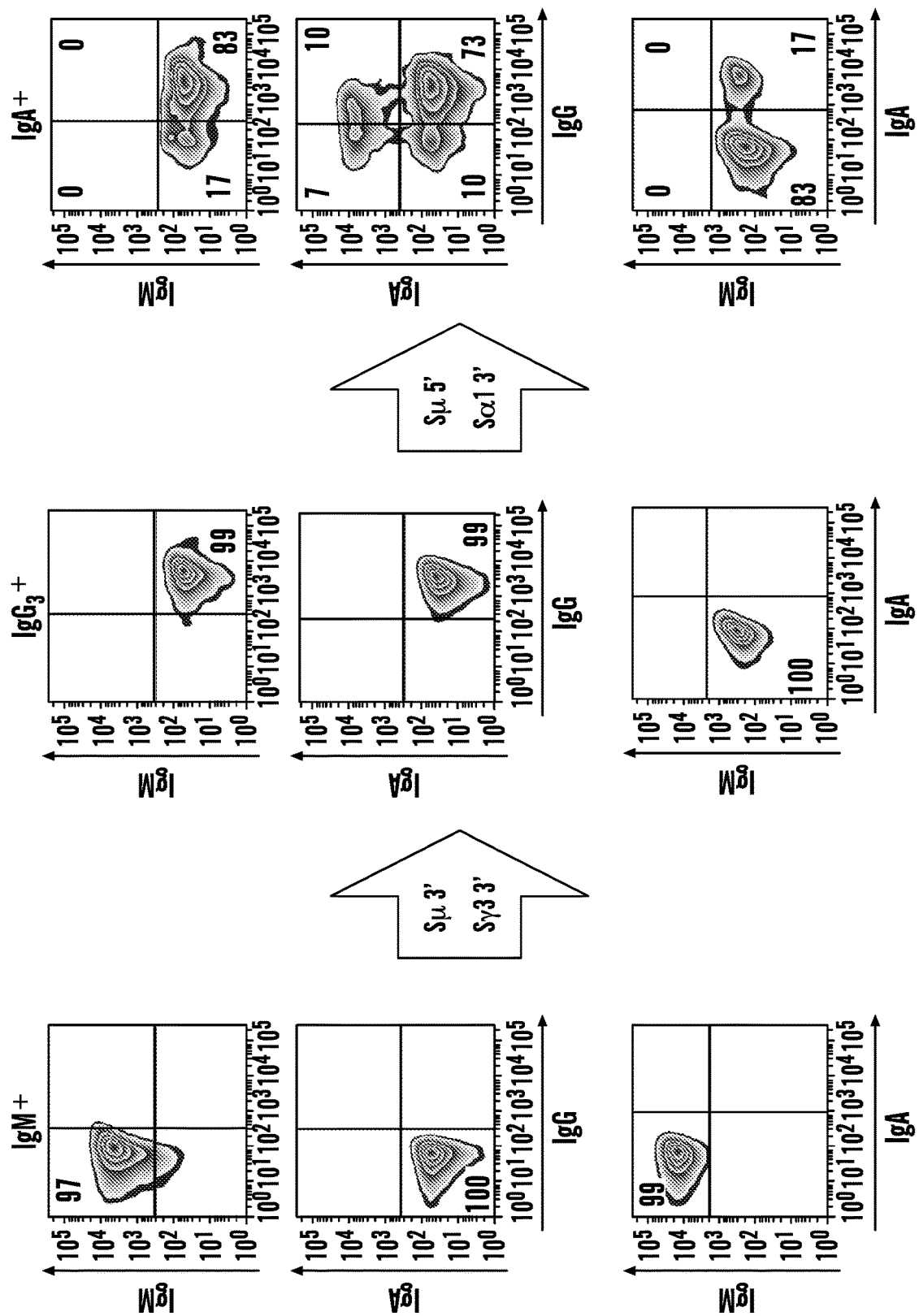
Figure 14:
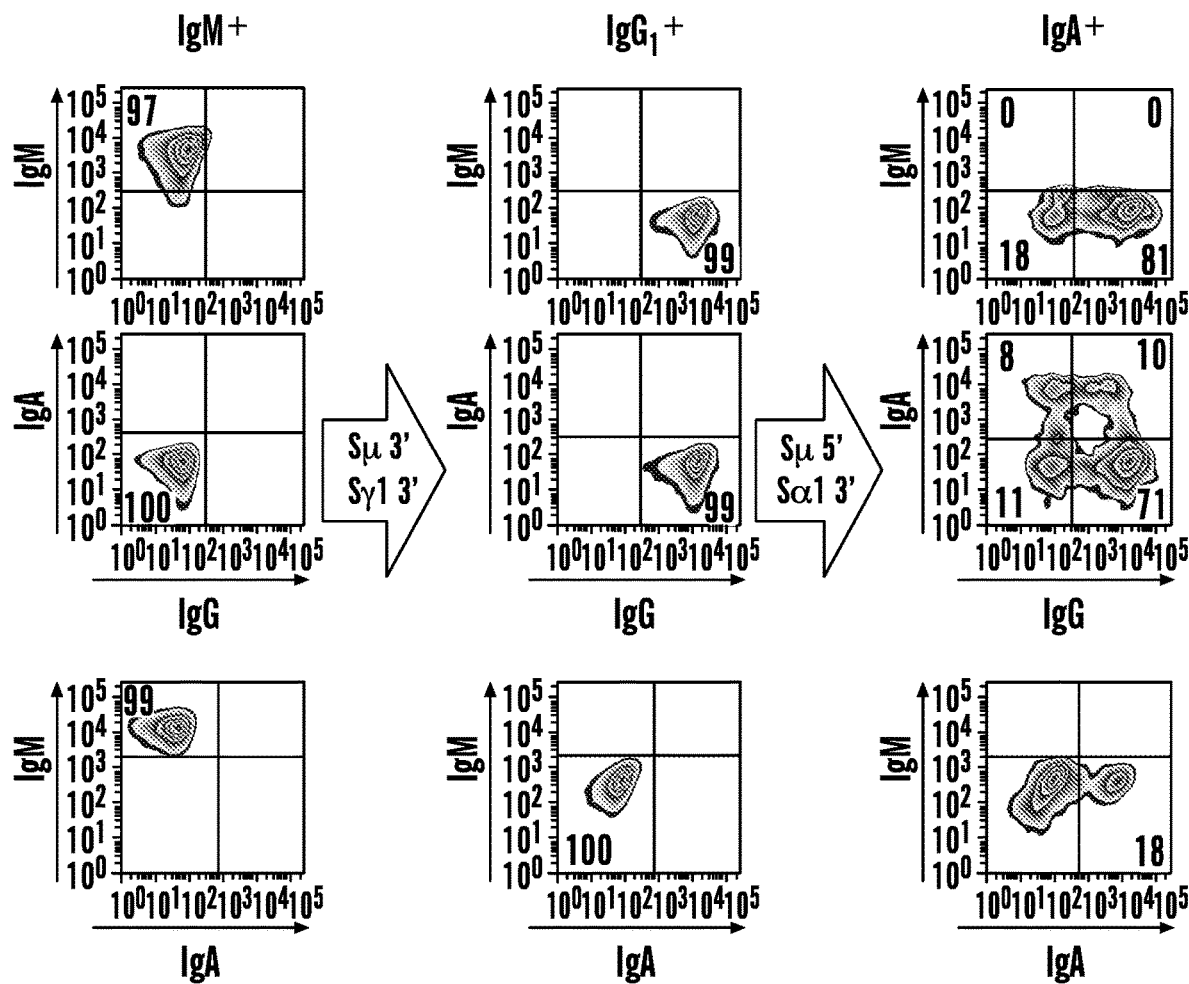
FIG. 14. Sequential CSR in JEKO-1 cells. To induce sequential class switching from IgM to IgG and then to IgA, IgM-expressing JEKO-1 cells were transduced with lentiviruses expressing Cas9 nuclease and gRNAs targeting Sµ 3' and Sγ1 3' flanking regions to generate IgG1-expressing JEKO-1 cells. IgG1-expressing cells were then transduced with lentiviruses expressing Cas9 nuclease and gRNAs targeting Sµ 5' and Sα1 3' flanking regions. Four days later, cells were collected, co-stained with antibodies IgM, IgG, or IgA, and analyzed by flow cytometry. Data were analyzed by FlowJo software. Representative zebra plots from one of three independent experiments are presented. Percentages of events are indicated in the corresponding quadrants.

Next, the inventors investigated whether human B cells could be engineered to undergo consecutive rounds of CSR, i.e. whether B cells induced to switch first from IgM to IgG3 (or IgG1) were then editable to a sequential switch to IgA. Starting from IgM+JEKO-1 cells, the inventors first induced CSR to IgG3 or IgG1 by lentiviral transduction with Sμ 3' gRNA and Sγ3 3' gRNA or Sγ1 3' gRNA and isolated pure IgG3+ or IgG1+ clones (FIG. 2D and FIG. 14). Next, we transduced IgG3+ or IgG1+ clones with Sμ 5' gRNA and Sα1 3' gRNA to generate new DSBs in regions flanking Sμ and Sα. Remarkably, we obtained high levels of CSR to IgA, indicating that human B cells can be engineered to undergo multiple rounds of CSR at the same efficiency rate (FIG. 2D and FIG. 14).

The high efficiency of CSR obtained in human B cell allows for potential studies on the biological role of different IgH subclass in lymphoma biology. Signaling through the B cell receptor (BCR) is required to sustain survival and proliferation of normal B cells[17, 18], and drugs inhibiting the BCR signaling are effective in the treatment of B cell lymphoma[19]. However, it is not clear whether different IgH subclasses that recognize the same antigen can affect lymphoma growth, possibly through a different potency or quality of the BCR signaling. The efficiency and rapidity of our CRISPR/Cas9-based method for CSR opens the possibility to address these questions. As a proof of principle the inventors followed over time B lymphoma cells engineered to switch to different IgH subclasses. First, a small fraction of lymphoma cells transduced with Cas9-gRNA lost the expression of any IgH, likely due to large deletions around the Cas9 cleavage site or to non-coding inversions or translocations. These IgH negative cells were selectively depleted over time, indicating a growth disadvantage of B lymphoma cells that lost the BCR signaling, as expected by previous studies[17, 18] (FIGS. 4A-4D). More surprisingly, different subclasses of IgH had contrasting biological effects on lymphoma growth, as IgG1+ cells had a significant growth disadvantage over IgM+cells, whereas IgG3+ or IgA+ cells were positively selected (FIGS. 4A-4D), thus indicating that different IgH subclasses in B cell lymphoma have different biological properties.

Figure 4A:
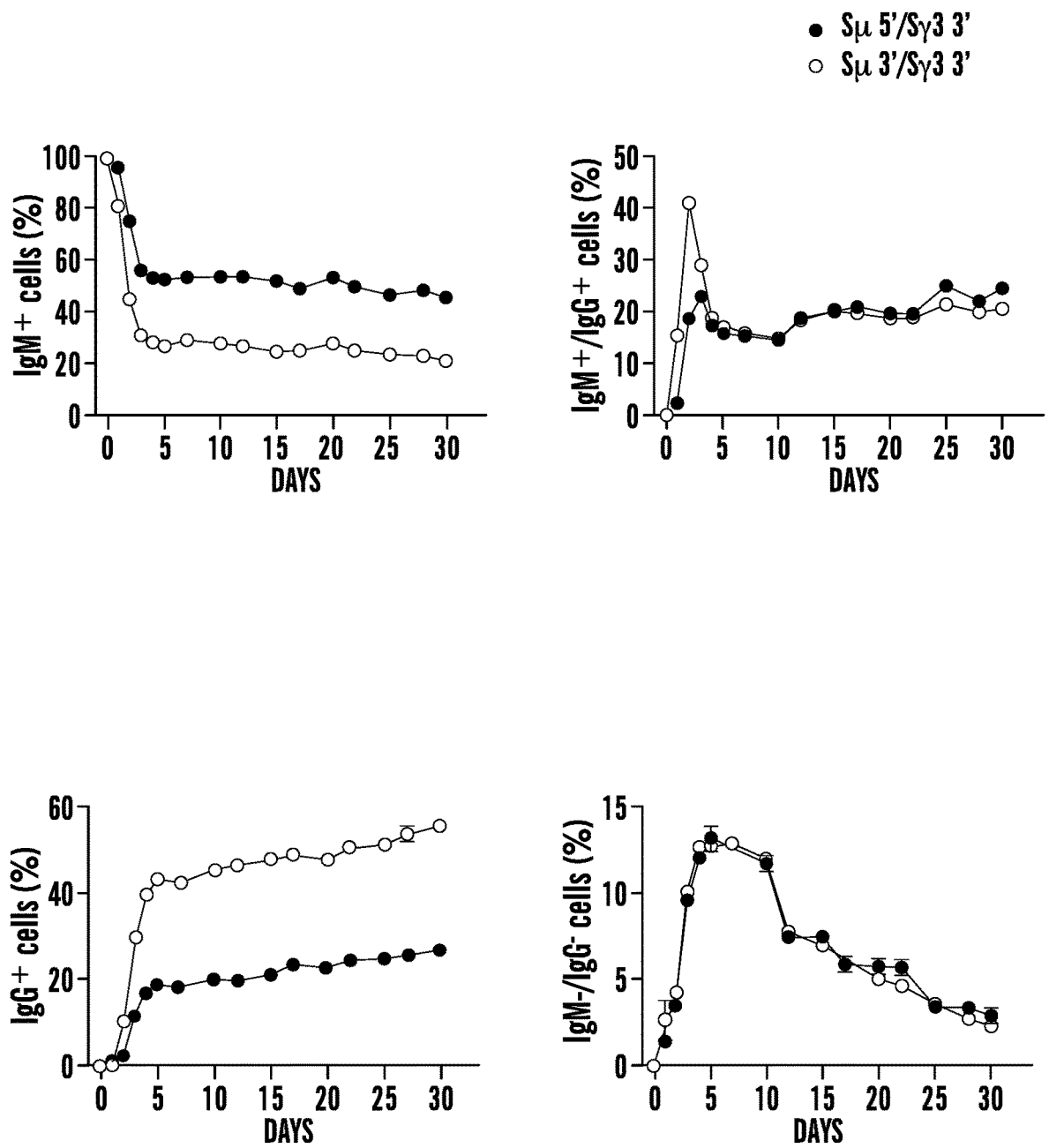
FIGS. 4A-4E. Biological effects of IgH subclass switch in human lymphoma cell growth.
Figure 4B:
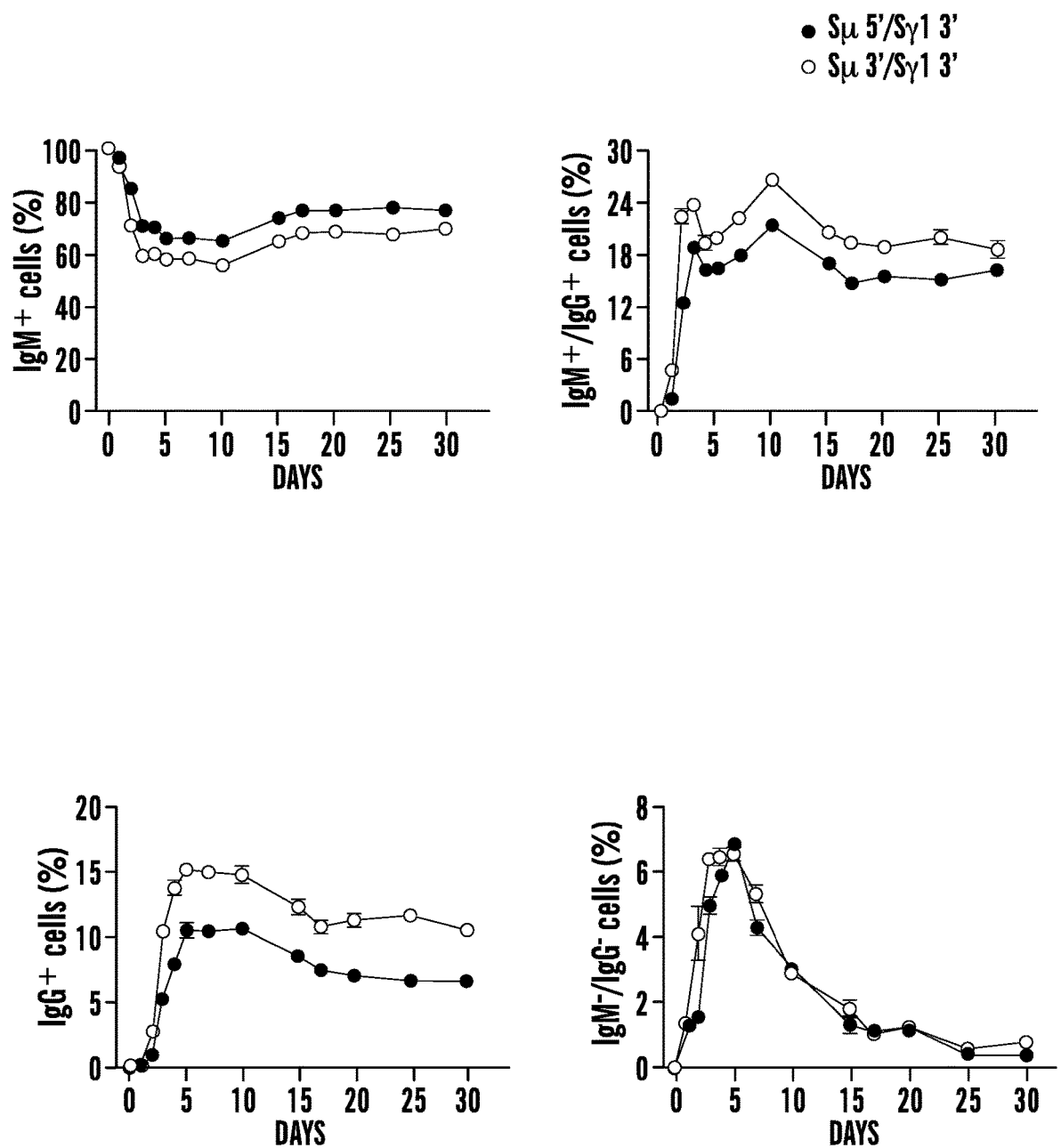
Figure 4C:
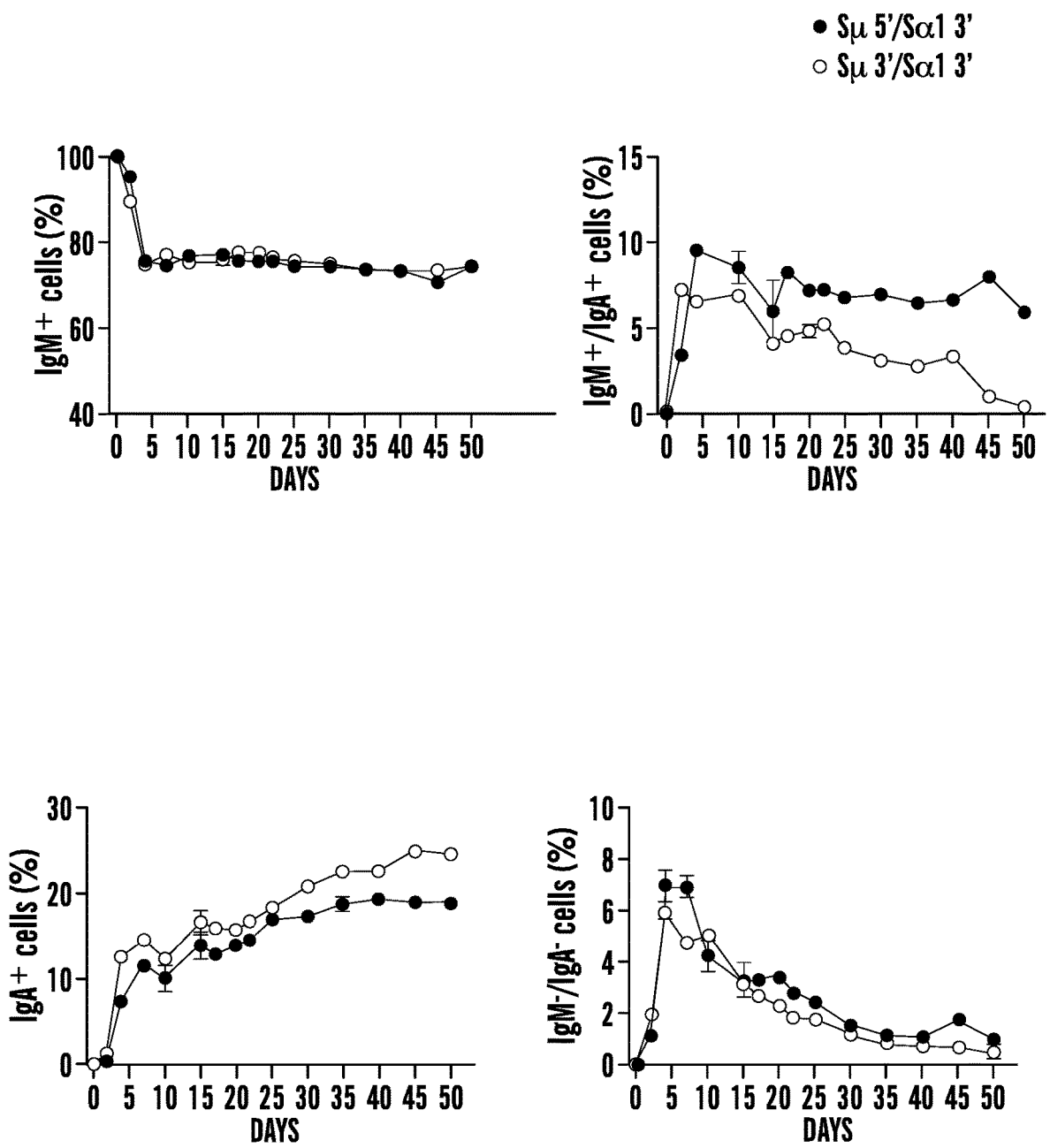
Figure 4D:
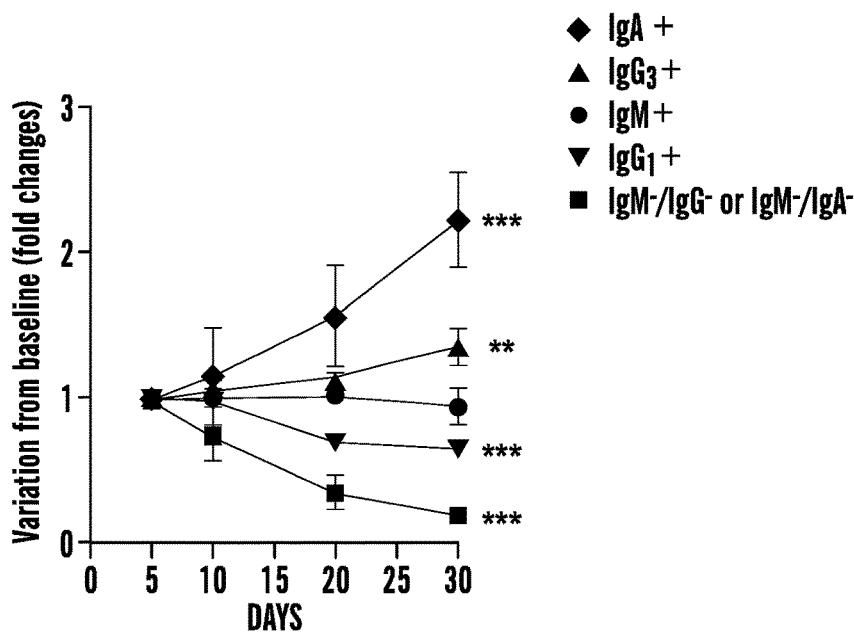
Figure 4E:
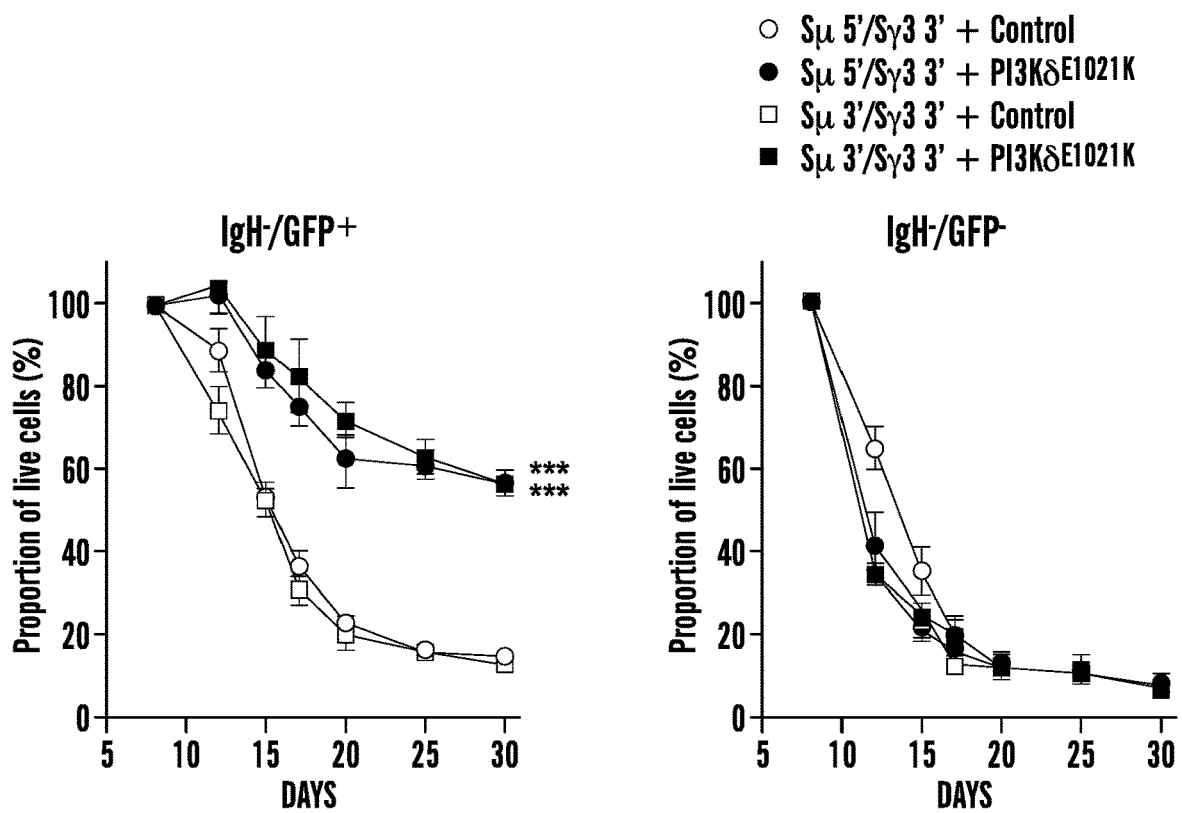

Next, the inventors further investigated whether loss of BCR signaling the lead to growth disadvantage in IgH negative cells could be rescued by compensatory activation of key pathways downstream of the BCR signaling. This is an important biological concept because the BCR signaling is essential for the survival of malignant B cells through the activation of key downstream molecules such as the PI3Kδ pathway[18]. To this end, the inventors took advantage of a newly discovered point mutation (PI3KδE1021K) that constitutively activates PI3Kδ independently of upstream BCR signaling and was recently described in patients with immunodeficiency and impaired CSR20, 21. After induction of IgH loss in the JEKO-1 cell line by transduction with either Sμ 5'/Sγ3 3' or Sμ 3'/Sγ3 3' gRNAs, we subsequently transduced the lymphoma cells with lentivirus expressing GFP as reporter (control vector) or GFP and PI3KδE1021K. IgH-negative lymphoma expressing GFP were progressively depleted with similar kinetics to untransduced cells. In contrast, IgH-negative lymphoma cells expressing PI3KδE1021K were significantly rescued as compared to GFP- or GFP+ control cells (FIG. 4E).

Figure 5A:
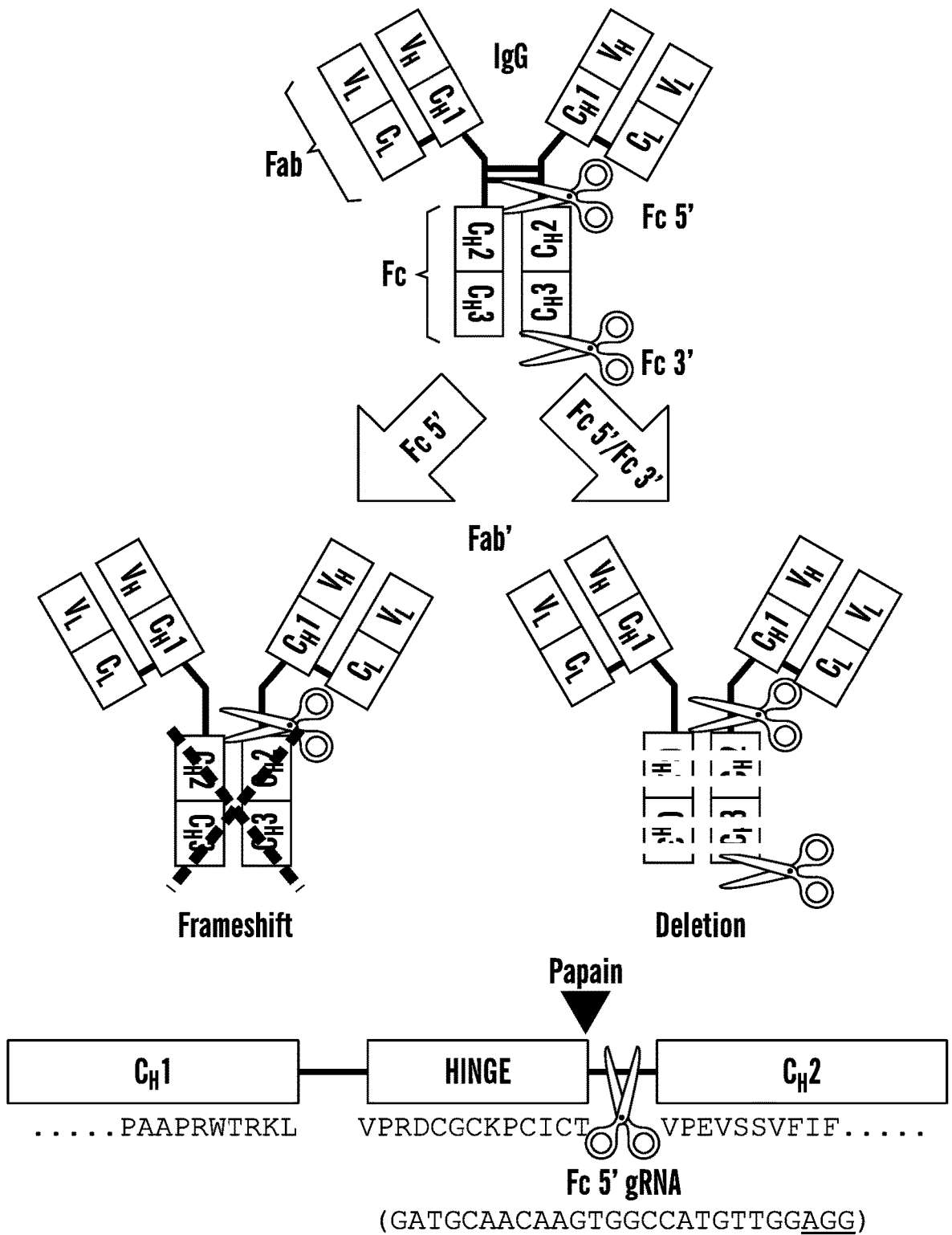
FIGS. 5A-5E. Generation of Fab' fragments by CRISPR/Cas9 system in mouse hybridomas.
Figure 5B:
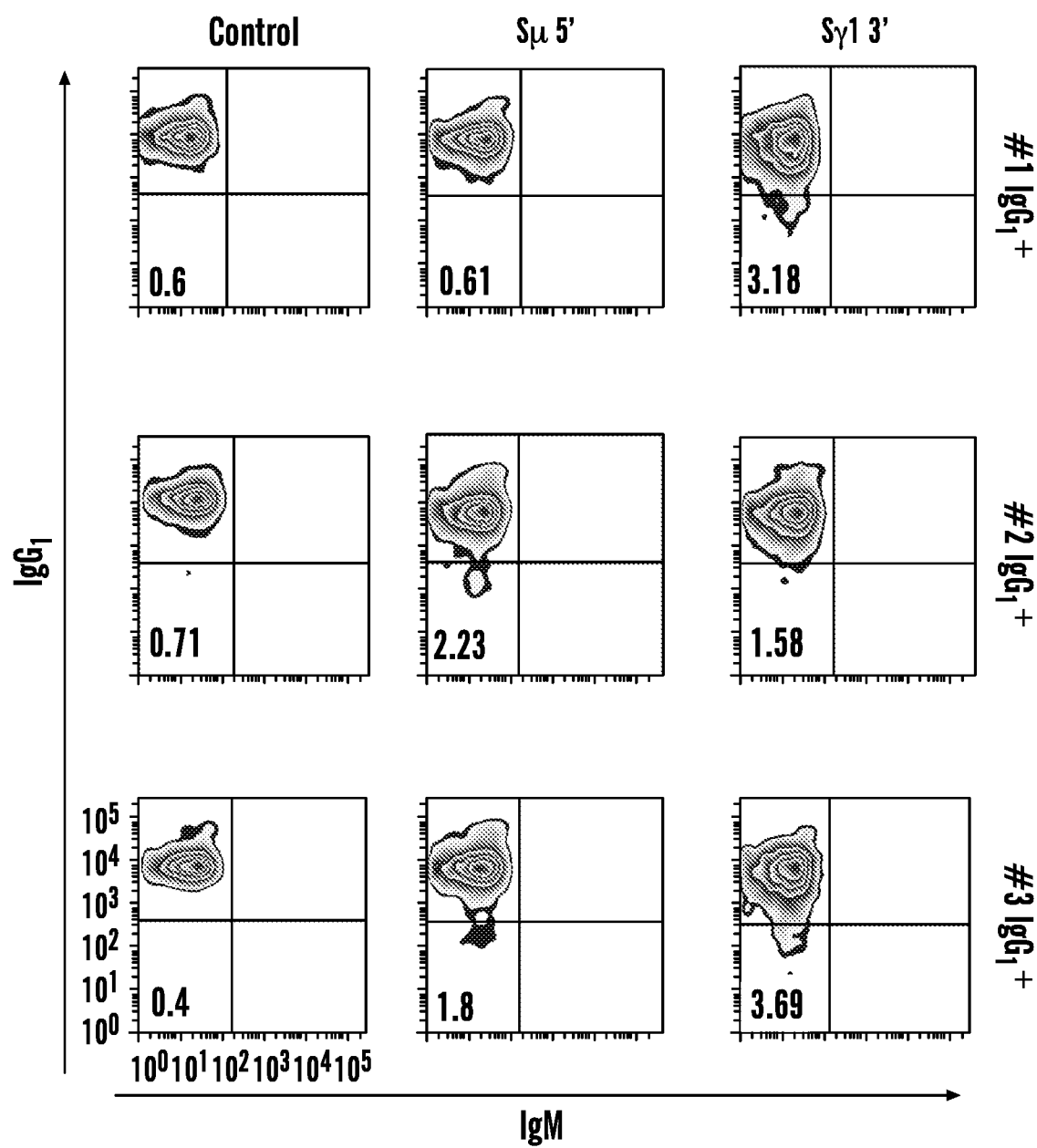
Figure 5B:
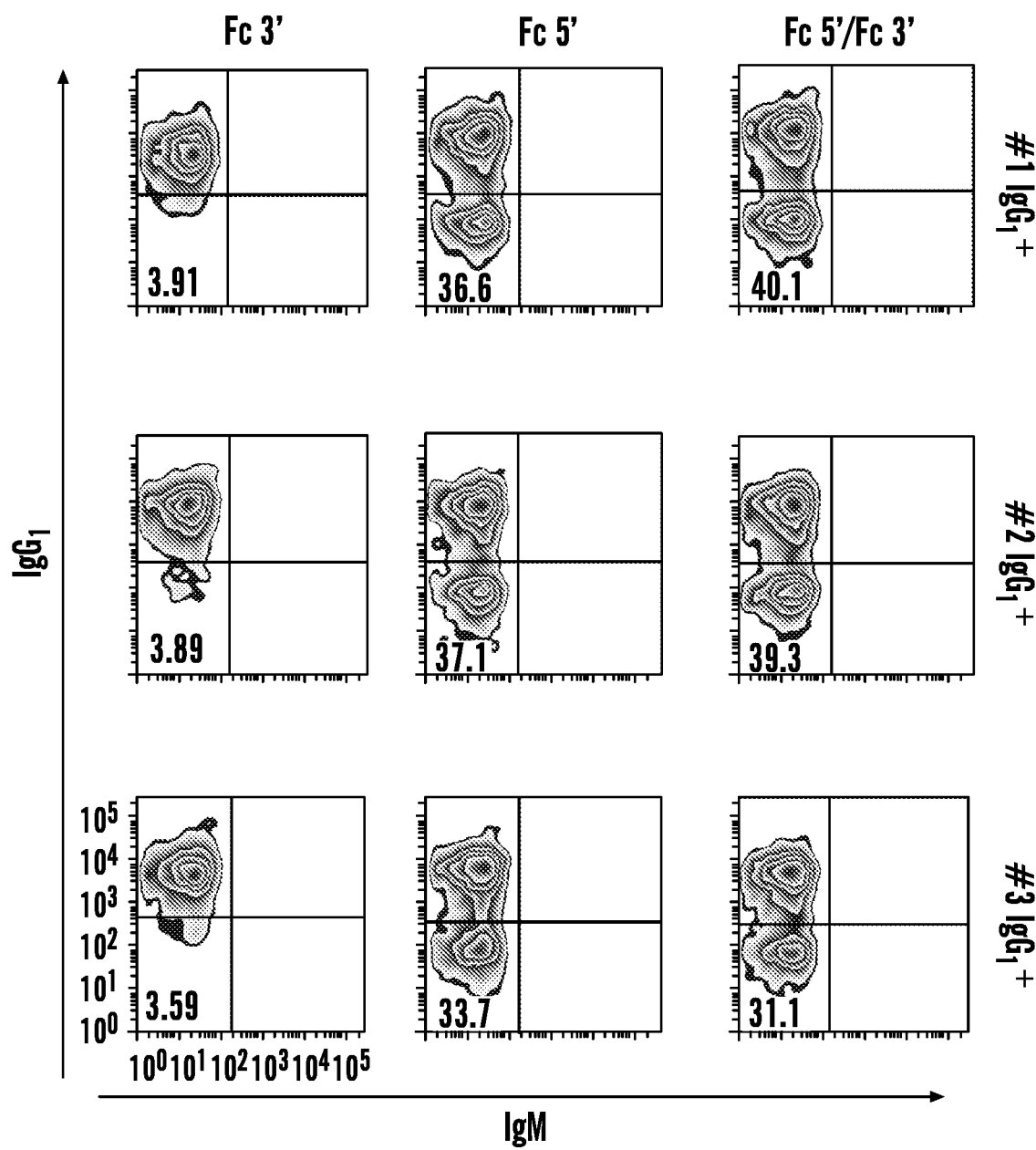
Figure 5C:
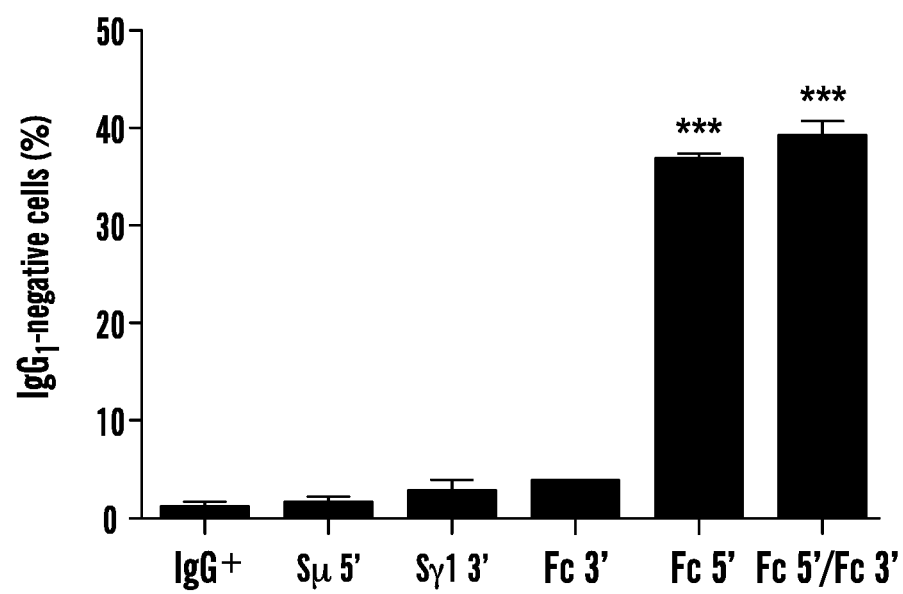
Figure 5E:
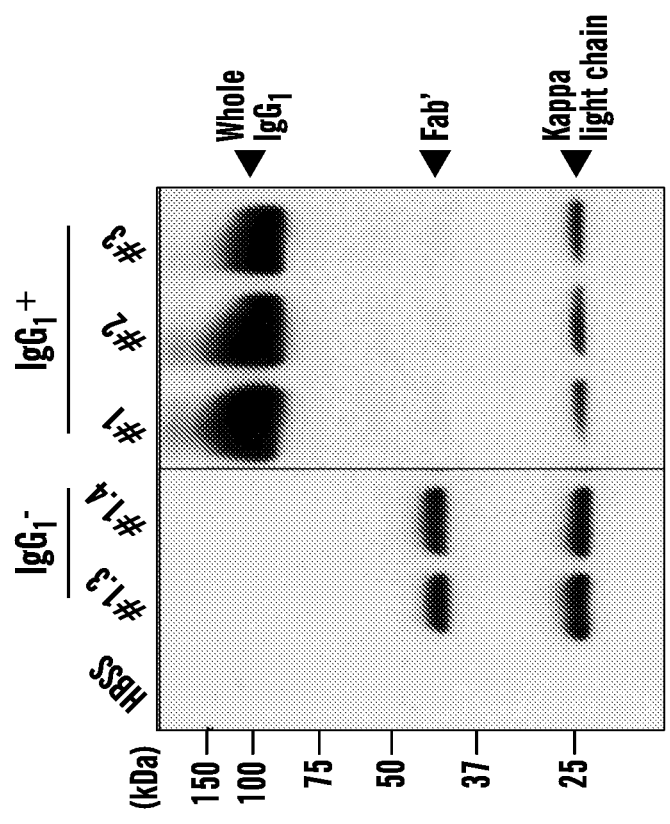
Figure 5D:
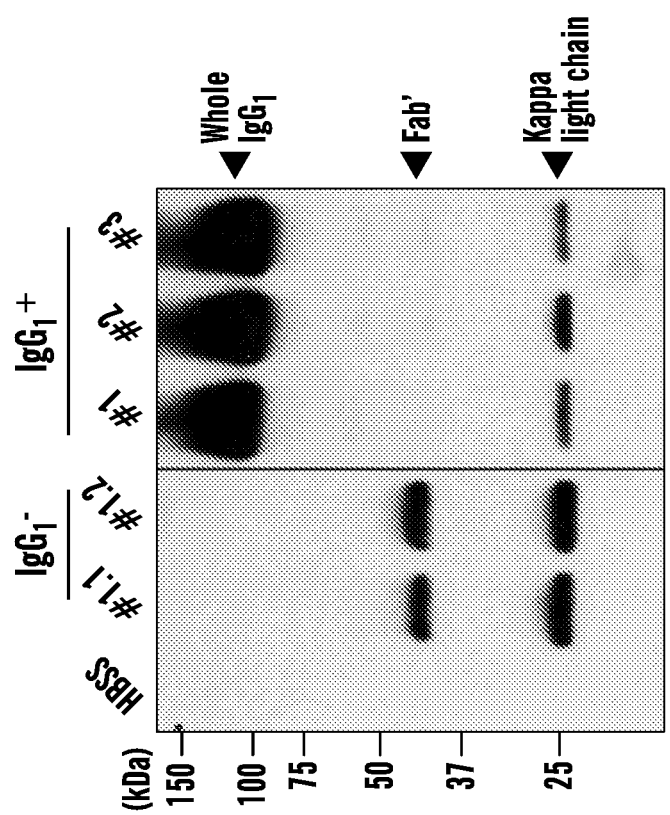
Figure 15A:
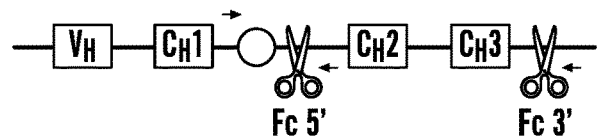
FIGS. 15A-15B. Detection of frameshift versus deletion frequency in Fab' producing hybridomas.
Figure 15B:
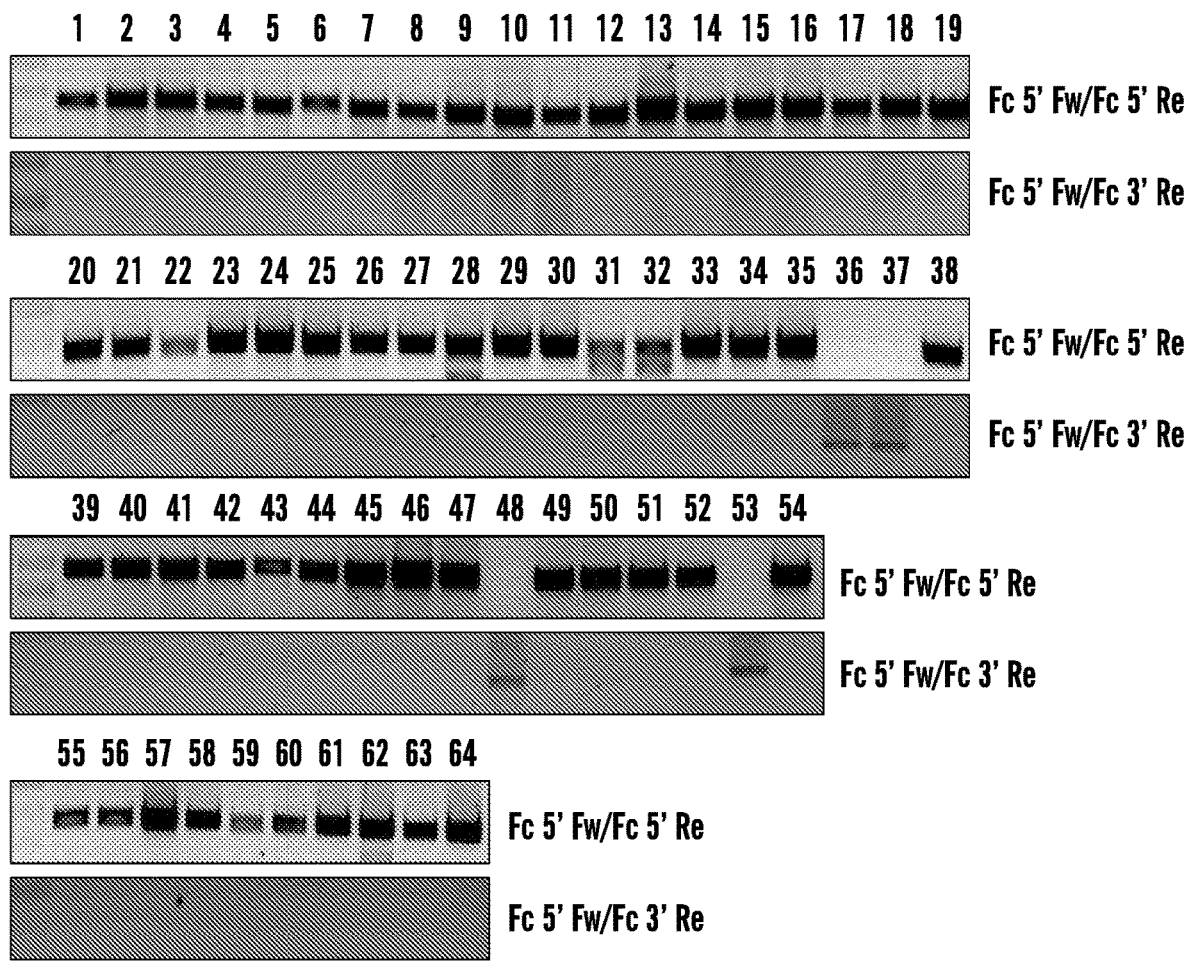
Figure 16A:
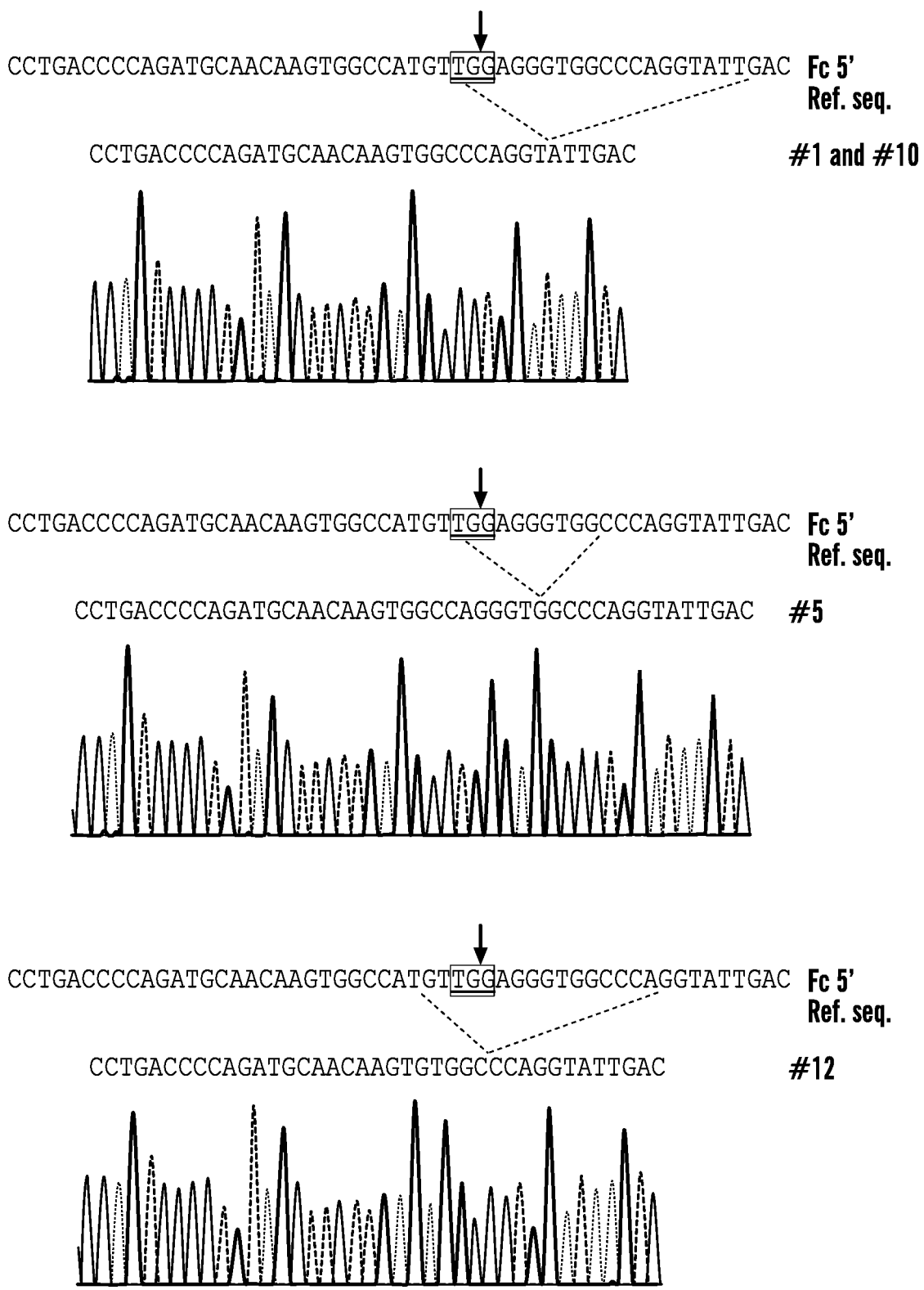
FIGS. 16A-16B. Examples Sanger sequencing of the spliced junctions in Fab' producing hybridomas clones wherein the Fab' are made with frameshift or deletion of the IgH Fc portion.
Figure 16B:
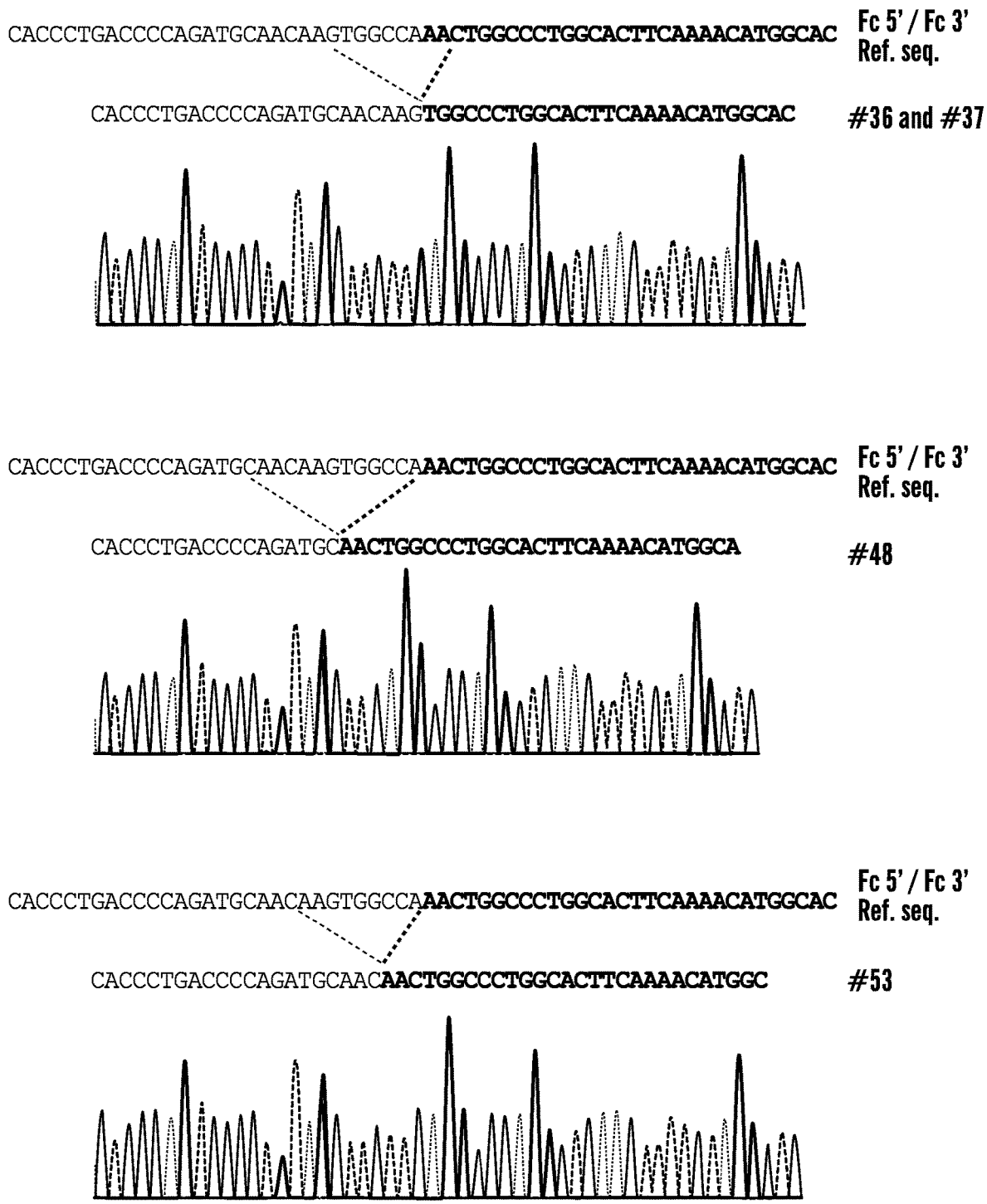
Figure 17:
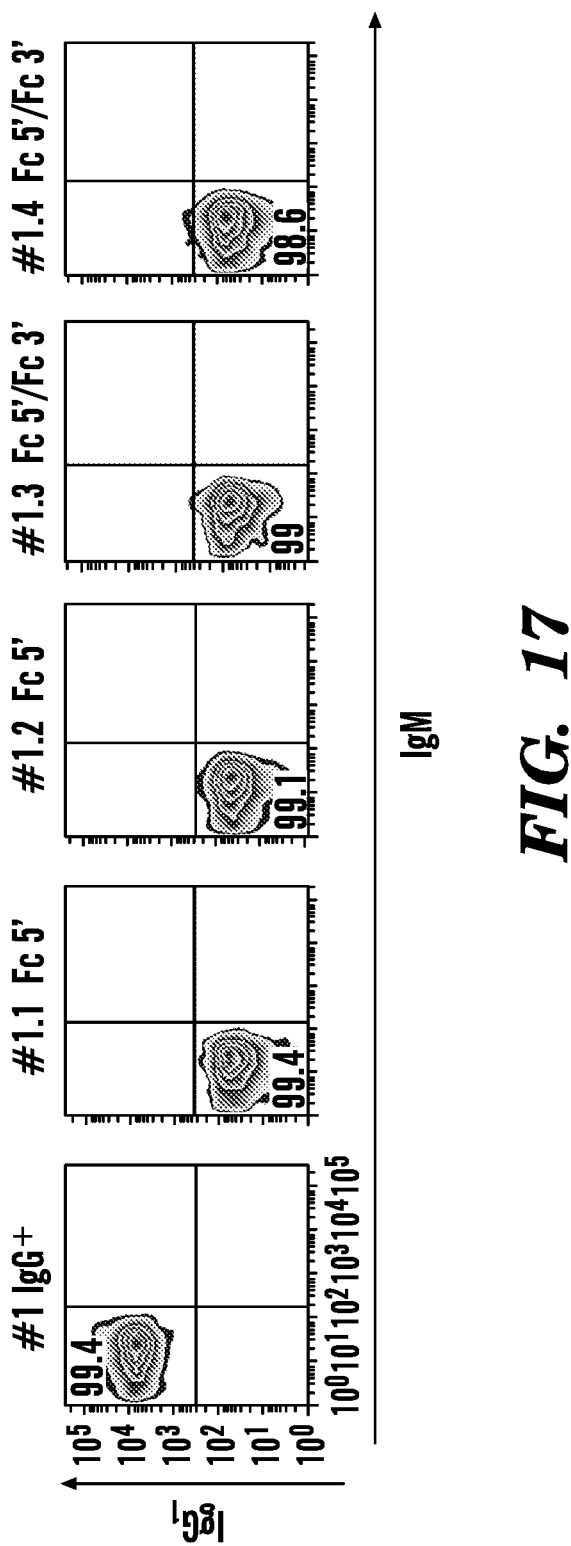
FIG. 17. Generation of hybridomas producing Fab' fragments. IgG1-expressing hybridoma (#1 from FIG. 5B) was transduced with lentivirus expressing Cas9 nuclease and gRNAs targeting Fc 5' (frameshift) or Fc 5' and Fc3' together (deletion). Cells were selected with puromycin (3 µg/ml) for 3 days, and cultured in 96-well plates to isolate IgG1-negative single cell clones expressing only Fab' fragments. Hybridomas were stained with IgM and IgG1 antibodies, and analyzed by flow cytometry. Two clones from the frameshift approach (#1.1 and 1.2) and 2 clones from deletion approach (#1.3 and #1.4) were generated with purity >99%. Data were analyzed by FlowJo software. Representative zebra plots are presented. Percentages of events are indicated in the corresponding quadrant.
Figure 18A:
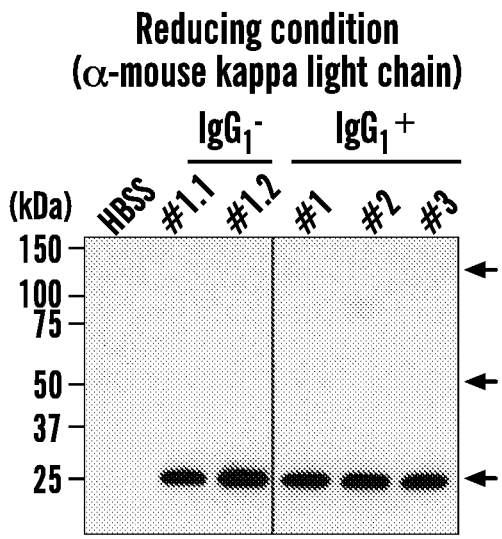
Figure 18A:
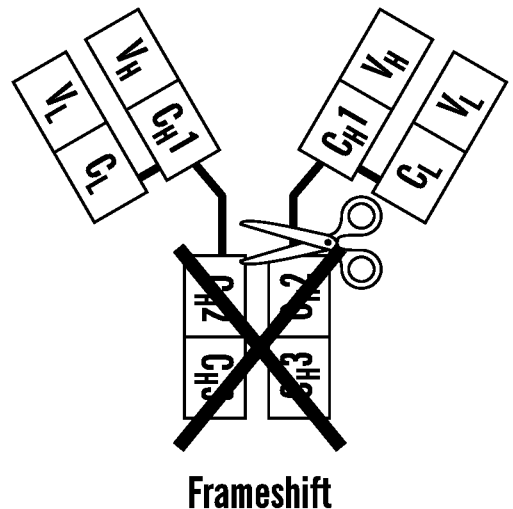
Figure 18B:
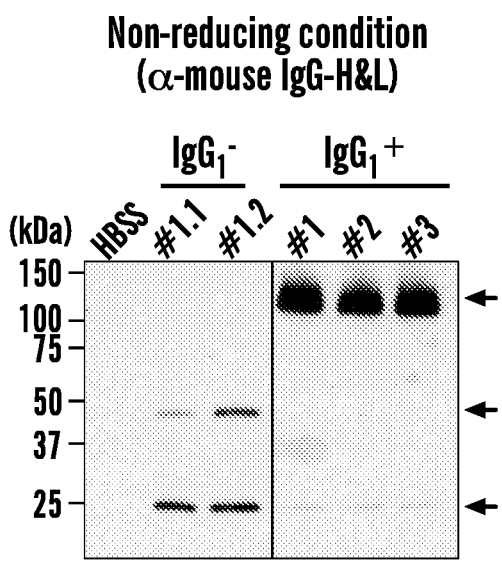
Figure 18C:
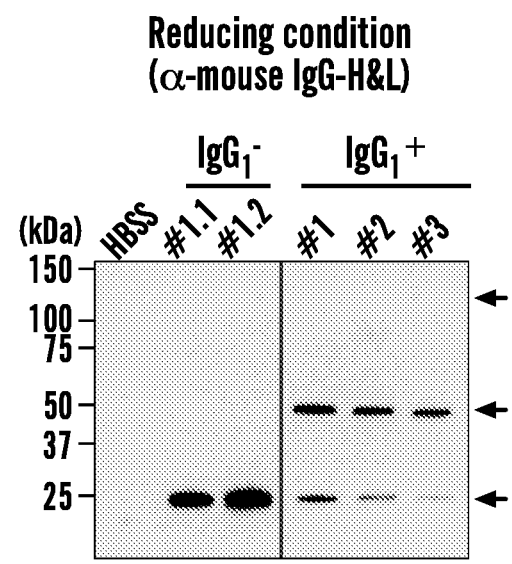

CRISPR/Cas9 mediated generation of hybridomas secreting IgH Fab' fragment. Finally, the high efficiency of CRISPR/Cas9 system to edit the IgH locus prompted the inventors to further investigate possible applications in antibody production. For several experimental or clinical applications, Fab' fragments are preferable to whole antibodies. To obtain Fab' fragments, purified antibodies are often processed by enzymatic digestion with proteases, such as papain or pepsin, followed by further purification to remove the Fc binding portion and to maintain the antigen-specific binding portion (Fab' fragment)[22]. The inventors reasoned that they could produce Fab' fragments directly in hybridoma cells by deleting the Fc coding sequence of the IgH chain. To obtain the Fc portion deletion, the inventors designed gRNAs targeting the DNA proximal to the papain cleavage site of the IgG1 coding sequence. The inventors tested either a frameshift approach where the deletion of the Fc portion is achieved by an out-of-frame NHEJ-mediated repair of the DSB introduced by Cas9 (Fc 5') or a complete deletion approach where the DNA sequence for the Fc portion is deleted by two flanking DSBs (Fc 5' and Fc 3') (FIG. 5A). As a consequence of this deletion, the hybridoma should become IgH negative because of the loss of the IgH membrane binding domain[23]. Indeed, by either approach, the inventors observed a high percentage of IgG1-negative cells (FIG. 5B-5C), likely indicating an efficient deletion of the Fc fragment. To compare the relative efficiency of the two approaches we isolated single clones from a hybridoma co-transduced with Fc 5' and Fc 3'. Out of the 64 isolated single cell clones, only 4 (6.2%) deleted the Fc coding sequence of the IgH chain, whereas in the majority of the clones the loss of the Fc coding was mediated by frameshift (FIG. 15 and FIG. 16). Next, the inventors expanded IgG1-negative clones (FIG. 17) and tested for production of Fab' fragments. The inventors collected hybridoma supernatants and separated the proteins on a SDS-PAGE gel in non-reducing conditions. By Western Blot assay with an anti-kappa light chain antibody, IgG1-negative engineered hybridomas secreted Fab' fragments together with the expected kappa-light chain[24], whereas control IgG1+ hybridomas secreted the whole IgG1 as expected (FIGS. 5D-5E). As predicted, both the Fab' fragments and the whole IgG1 completely disappeared when the SDS-PAGE gel was run in reducing conditions (FIG. 18). Thus, hybridomas producing Fab' fragments can be generated rapidly and effectively by CRISPR/Cas9 technology.

Altogether the data demonstrate the feasibility of a fast and efficient editing the Ig genes in human and mouse B cells by CRISPR/Cas9 technology. CSR was induced with equal efficiency whether the gRNA were directed to target sequences upstream or downstream the switch regions, as predicted by the current models of CSR[3, 25]. Consistent with the notion that CSR is a peculiar form of gene rearrangement in the IgH locus, when two gRNAs were introduced in the cells the inventors found additional genomic rearrangements, such as inversions and interchromosomal translocations as we and other previously described with CRISPR/Cas9 technology [11-14]. The predominance of precise junctions between the two DSBs generated by Cas9 reflects the described property of Cas9 to generate blunt ends 3 bp upstream of the PAM sequence[26]. Blunt ends are then joined by the c-NHEJ pathway, which could also be responsible for small deletions or insertions[6].

Efficiency of CSR was remarkably high in hybridoma and human B lymphoma cells. This was quite surprising but consistent with the observations made by our group and others that rearrangements occur with high frequency between two DSBs that occur at a low genomic distance on the same chromosome[7, 15, 27, 28]. The lower CSR achieved in primary mouse B cells was likely due to a lower efficiency of transduction than hybridoma and human B cells. Currently used lentiviral or retroviral CRISPR/Cas9 vectors produce relatively low viral titers due to the large size of the constructs[29]. The recent demonstration that smaller Cas9 molecules obtained by *Staphylococcus aureus* have similar efficiency to *Streptococcus pyogenes* (SpCas9) allows the design of smaller retroviral constructs that should generate more efficient viruses[30]. In addition, the cloning of two gRNAs in the same vector instead two independent vectors should further increase the efficiency of CSR by increasing the number of cells co-expressing the two gRNAs.

CRISPR/Cas9 mediated CSR in hybridoma cells was efficient, fast and easy allowing for CSR to any desired IgH subclass. Implication for the technology of antibody production could be profound. For example, IgG antibodies are preferred for applications such as western blot analysis, immunohistochemistry and ELISA whereas IgM clones are typically discarded because IgM are pentameric, more difficult to purify and less stable than IgG. In addition, different IgG subclasses have different stability, as well as biological and biochemical properties. For examples, effector functions in terms of triggering FcγR-expressing cells, activating complement, phagocytosis or antibody-dependent cell-mediated cytotoxicity are different within IgG1, IgG2, IgG3, and IgG4 subclasses[30]. By applying the approach we propose, it would be possible to easily switch hybridomas to the desired IgH subclass for any laboratory or therapeutic use. In addition, the inventors have also shown that hybridoma can be engineered to produce Fab' fragments instead of the corresponding whole IgH molecule. Fab' fragments were directly produced and secreted by hybridoma cells in culture at comparable levels to the unedited whole IgH molecules. This approach would largely simplify the method for the production of Fab' fragments that is currently based on several steps of protease cleavage followed by purification of the resulting fragments.

Finally, CSR was achieved in human B cells at high efficiency, a feat never accomplished so far. In contrast to primary mouse B cells, induction of CSR in human B cells is largely inefficient with current methods [32]. In contrast, by CRISPR/Cas9 technology the inventors were able to rapidly and efficiently induce CSR in all human B cell lines tested to any desired IgH subclass. This Cas9-mediated editing methodology provides a highly useful approach for the study of the functional activity of different IgH subclass in the physiology and pathology of human B cells as the contribution of the different IgH subclasses is largely unknown. Furthermore, unveiling the network of signaling pathways initiated by the BCR has become increasingly important to understand the physiology of normal B cells 17 as well as the pathological survival and expansion of neoplastic B cells 19. Indeed, inhibition of BCR activity has recently changed the treatment landscape for B-cell malignancies[33-38]. Inhibitors of key molecules in BCR signaling such as PI3Kδ inhibitors (idelalisib) or Bruton tyrosine kinase-BTK inhibitors (ibrutinib) have been recently approved by the FDA for the treatment of CLL or MCL39 and others are under investigation[40]. As we showed in reconstitution experiments with activated PI3Kδ constructs, modeling CSR or eliminating BCR signaling by CRISPR/Cas9 technology will provide opportunities to precisely reconstruct the contribution of single pathways or molecules to the biology of normal and neoplastic B cells.

The references cited herein and throughout the specification are incorporated herein by reference.

REFERENCES

1. Hsu, P. D., Lander, E. S. & Zhang, F. Development and applications of CRISPR-Cas9 for genome engineering. Cell 157, 1262-1278 (2014).
2. Doudna, J. A. & Charpentier, E. Genome editing. The new frontier of genome engineering with CRISPR-Cas9. Science 346, 1258096 (2014).
3. Gostissa, M., Alt, F. W. & Chiarle, R. Mechanisms that promote and suppress chromosomal translocations in lymphocytes. Annual review of immunology 29, 319-350 (2011).
4. Jung, D., Giallourakis, C., Mostoslaysky, R. & Alt, F. W. Mechanism and control of V(D)J recombination at the immunoglobulin heavy chain locus. Annual review of immunology 24, 541-570 (2006).
5. Stavnezer, J., Guikema, J. E. J. & Schrader, C. E. Mechanism and regulation of class switch recombination. Annual review of immunology 26, 261-292 (2008).
6. Boboila, C., Alt, F. W. & Schwer, B. Classical and alternative end-joining pathways for repair of lymphocyte-specific and general DNA double-strand breaks. Advances in immunology 116, 1-49 (2012).
7. Gostissa, M. et al. IgH class switching exploits a general property of two DNA breaks to be joined in cis over long chromosomal distances. Proceedings of the National Academy of Sciences of the United States of America 111, 2644-2649 (2014).
8. Zarrin, A. A. et al. Antibody class switching mediated by yeast endonuclease-generated DNA breaks. Science 315, 377-381 (2007).
9. Shalem, O., Sanjana, N. E. & Zhang, F. High-throughput functional genomics using CRISPR-Cas9. Nature reviews. Genetics 16, 299-311 (2015).
10. O'Connell, M. R. et al. Programmable RNA recognition and cleavage by CRISPR/Cas9. Nature 516, 263-266 (2014).
11. Choi, P. S. & Meyerson, M. Targeted genomic rearrangements using CRISPR/Cas technology. Nature communications 5, 3728 (2014).
12. Torres, R. et al. Engineering human tumour-associated chromosomal translocations with the RNA-guided CRISPR-Cas9 system. Nature communications 5, 3964 (2014).
13. Blasco, R. B. et al. Simple and rapid in vivo generation of chromosomal rearrangements using CRISPR/Cas9 technology. Cell reports 9, 1219-1227 (2014).
14. Maddalo, D. et al. In vivo engineering of oncogenic chromosomal rearrangements with the CRISPR/Cas9 system. Nature 516, 423-427 (2014).
15. Chiarle, R. et al. Genome-wide translocation sequencing reveals mechanisms of chromosome breaks and rearrangements in B cells. Cell 147, 107-119 (2011).
16. Carter, P. J. Potent antibody therapeutics by design. Nature reviews. Immunology 6, 343-357 (2006).
17. Srinivasan, L. et al. PI3 kinase signals BCR-dependent mature B cell survival. Cell 139, 573-586 (2009).
18. Kraus, M., Alimzhanov, M. B., Rajewsky, N. & Rajewsky, K. Survival of resting mature B lymphocytes depends on BCR signaling via the Igalpha/beta heterodimer. Cell 117, 787-800 (2004).
19. Young, R. M. & Staudt, L. M. Targeting pathological B cell receptor signalling in lymphoid malignancies. Nature reviews. Drug discovery 12, 229-243 (2013).
20. Angulo, I. et al. Phosphoinositide 3-kinase delta gene mutation predisposes to respiratory infection and airway damage. Science 342, 866-871 (2013).
21. Lucas, C. L. et al. Dominant-activating germline mutations in the gene encoding the PI(3)K catalytic subunit p110delta result in T cell senescence and human immunodeficiency. Nature immunology 15, 88-97 (2014).
22. Filpula, D. Antibody engineering and modification technologies. Biomolecular engineering 24, 201-215 (2007).
23. Feige, M. J., Hendershot, L. M. & Buchner, J. How antibodies fold. Trends in biochemical sciences 35, 189-198 (2010).
24. Couture, M. L. & Heath, C. A. Relationship between loss of heavy chains and the appearance of nonproducing hybridomas. Biotechnology and bioengineering 47, 270-275 (1995).
25. Alt, F. W., Zhang, Y., Meng, F. L., Guo, C. & Schwer, B. Mechanisms of programmed DNA lesions and genomic instability in the immune system. Cell 152, 417-429 (2013).
26. Jinek, M. et al. A programmable dual-RNA-guided DNA endonuclease in adaptive bacterial immunity. Science 337, 816-821 (2012).
27. Chiarle, R. Translocations in normal B cells and cancers: insights from new technical approaches. Advances in immunology 117, 39-71 (2013).
28. Hakim, O. et al. DNA damage defines sites of recurrent chromosomal translocations in B lymphocytes. Nature 484, 69-74 (2012).
29. Sanjana, N. E., Shalem, O. & Zhang, F. Improved vectors and genome-wide libraries for CRISPR screening. Nature methods 11, 783-784 (2014).
30. Ran, F. A. et al. In vivo genome editing using *Staphylococcus aureus* Cas9. Nature 520, 186-191 (2015).
31. Deonarain, M. P., Yahioglu, G., Stamati, I. & Marldew, J. Emerging formats for next-generation antibody drug conjugates. Expert opinion on drug discovery, 1-19 (2015).
32. Horiuchi, K. et al. Analysis of somatic hypermutations in the IgM switch region in human B cells. The Journal of allergy and clinical immunology 134, 411-419 (2014).
33. Byrd, J. C. et al. Targeting BTK with ibrutinib in relapsed chronic lymphocytic leukemia. The New England journal of medicine 369, 32-42 (2013).
34. Wang, M. L. et al. Targeting BTK with ibrutinib in relapsed or refractory mantle-cell lymphoma. The New England journal of medicine 369, 507-516 (2013).
35. Furman, R. R. et al. Idelalisib and rituximab in relapsed chronic lymphocytic leukemia. The New England journal of medicine 370, 997-1007 (2014).
36. Gopal, A. K. et al. PI3Kdelta inhibition by idelalisib in patients with relapsed indolent lymphoma. The New England journal of medicine 370, 1008-1018 (2014).
37. Wilson, W. H. et al. Targeting B cell receptor signaling with ibrutinib in diffuse large B cell lymphoma. Nature medicine (2015).
38. Hamadani, M., Balasubramanian, S. & Hari, P. N. Ibrutinib in Refractory Classic Hodgkin's Lymphoma. The New England journal of medicine 373, 1381-1382 (2015).
39. Fuman, D. A. & Cantley, L. C. Idelalisib—a PI3Kdelta inhibitor for B-cell cancers. The New England journal of medicine 370, 1061-1062 (2014). 40. Byrd, J. C. et al. Acalabrutinib (ACP-196) in Relapsed Chronic Lymphocytic Leukemia. The New England journal of medicine (2015).

TABLE 1 gRNA guide sequences and PAM sequences used in this study.

| Target | 20 nt-guide sequence | PAM | SEQ ID NO: |
|---|---|---|---|
| Mouse IgH | | | |
| Sµ 5' | GCCAGAGGCAGCCACAGCTG | TGG | 5 |
| Sµ 3' | GTCACGTTCCTGTGGCTAGA | AGG | 6 |
| Sγ1 5' | GGAAAGTGCAAGCTGCTCTG | AGG | 7 |
| Sγ1 3' | GAGAGTCGGGACATGGGAA | GGG | 8 |
| Hybridoma | | | |
| Fc 5' | GATGCAACAAGTGGCCATGT | TGG | 9 |
| Fc 3' | TGTGCTCTTCCTATGCAAAC | TGG | 10 |

TABLE 1-continued gRNA guide sequences and PAM sequences used in this study.

| Target | 20 nt-guide sequence | PAM | SEQ ID NO: |
|---|---|---|---|
| Human IgH | | | |
| Sμ 5' | ATATTCCACCCAGGTAGTGG | AGG | 11 |
| Sμ 3' | ACAGCGGGACGCAAGTAGTG | AGG | 12 |
| Sγ3 3' | TCGTGGATAGACAAGAACCG | AGG | 13 |
| Sγ1 3' | TCGCGGACAGTTAAGAACCC | AGG | 14 |
| Sα1 3' | GCTGGGTTCCTCCAGTATAG | AGG | 15 |

TABLE 2

Oligonucleotides cloned in CRISPR/Cas9 lenti- or retro-viral vectors.

| Primer | Sequence (5'-3') | SEQ ID NO: |
|---|---|---|
| Mouse IgH | | |
| Sμ 5' Fw | CACCGCCAGAGGCAGCCACAGCTG | 16 |
| Sμ 5' Re | AAACCAGCTGTGGCTGCCTCTGGC | 17 |
| Sμ 3' Fw | CACCGTCACGTTCCTGTGGCTAGA | 18 |
| Sμ 3' Re | AAACTCTAGCCACAGGAACGTGAC | 19 |
| Sγ1 5' Fw | CACCGGAAAGTGCAAGCTGCTCTG | 20 |
| Sγ1 5' Re | AAACCAGAGCAGCTTGCACTTTCC | 21 |
| Sγ1 3' Fw | CACCGAGAGTCGGGGACATGGGAA | 22 |
| Sγ1 3' Re | AAACTTCCCATGTCCCCGACTCTC | 23 |
| Hybridoma | | |
| Fc 5' Fw | CACCGATGCAACAAGTGGCCATGT | 24 |
| Fc 5' Re | AAACACATGGCCACTTGTTGCATC | 25 |
| Fc 3' Fw | CACCGTGTGCTCTTCCTATGCAAAC | 26 |
| Fc 3' Re | AAACGTTTGCATAGGAAGAGCACAC | 27 |
| Human IgH | | |
| Sμ 5' Fw | CACCGATATTCCACCCAGGTAGTGG | 28 |
| Sμ 5' Re | AAACCCACTACCTGGGTGGAATATC | 29 |
| Sμ 3' Fw | CACCGACAGCGGGACGCAAGTAGTG | 30 |
| Sμ 3' Re | AAACCACTACTTGCGTCCCGCTGTC | 31 |
| Sγ3 3' Fw | CACCGTCGTGGATAGACAAGAACCG | 32 |
| Sγ3 3' Re | AAACCGGTTCTTGTCTATCCACGAC | 33 |

TABLE 2-continued

Oligonucleotides cloned in CRISPR/Cas9 lenti- or retro-viral vectors.

| Primer | Sequence (5'-3') | SEQ ID NO: |
|---|---|---|
| Sγ1 3' Fw | CACCGTCGCGGACAGTTAAGAACCC | 34 |
| Sγ1 3' Re | AAACGGGTTCTTAACTGTCCGCGAC | 35 |
| Sα1 3' Fw | CACCGCTGGGTTCCTCCAGTATAG | 36 |
| Sα1 3' Re | AAACCTATACTGGAGGAACCCAGC | 37 |

Fw = forward; Re = reverse.

TABLE 3

PCR primers used in deletion, inversion, excision circle, and surveyor assay.

| Primer | Sequence (5'-3') | SEQ ID NO: |
|---|---|---|
| Mouse IgH (deletion inversion, excision circle, and surveyor assay) | | |
| Sμ 5' Fw | CTTATTTCGGTTGAACATGC | 38 |
| Sμ 5' Fw2 | GGACACTCAGTCAGTCAGTG | 39 |
| Sμ 5' Re | CCTGGGTCCCTCCTTACTGA | 40 |
| Sμ 3' Fw | CAGACTGTGTGCTACAGTGG | 41 |
| Sμ 3' Fw2 | AGGACCTCGTTCTATAGAGG | 42 |
| Sμ 3' Re | GGTATTCATCTGAACCTTCA | 43 |
| Sγ1 5' Fw | GCCTGGTGTCAACTAGGCAG | 44 |
| Sγ1 5' Re | GGATGCCCTGGCACTGCTCT | 45 |
| Sγ1 5' Re2 | CTTACCTGTAGCTACTCTGC | 46 |
| Sγ1 3' Fw | GGAAATGTCAAGAGCCAACG | 47 |
| Sγ1 3' Re | GCCTCACTTCTAGTGAACCC | 48 |
| Human IgH (deletion, inversion and excision circle) | | |
| Sμ 5' Fw | CTGTAGGTCATCATCGCACC | 49 |
| Sμ 5' Re | GGTGCAACTTAGCCCAGCTC | 50 |
| Sμ 3' Fw | GAGCTGAGTGTGTGCAGCAC | 51 |
| Sμ 3' Re | CTGTGCCCTGCATGACGTCC | 52 |
| Sγ3 3' Fw | CAGTGTCCACTGGTCAAGCC | 53 |
| Sγ3 3' Re | CGTTGCAGGTGTAGGTCTGG | 54 |
| Sγ1 3' Fw | CAGTGTCCACTGGTCAAGCC | 53 |
| Sγ1 3' Re | CGTTGCAGATGTAGGTCTGG | 55 |

TABLE 4

| Starting type of mammalian cell | Start or Final IgH subclass | Example gRNA guide sequences to use in regions 5'- or 3'- end of the corresponding Ig switch | PAM sequence | SEQ ID NO: | Genomic coordinates of the regions 5'- or 3'- end of the corresponding Ig switch for gRNA guide sequences design |
|---|---|---|---|---|---|
| Naïve mouse B cell and mouse hybridoma | Start: IgM | 5': GCCAGAGGCAGCCACAGCTG<br>3': GTCACGTTCCTGTGGCTAGA | TGG<br>AGG | 5<br>6 | Chromosome 12: 113,425,856-113,426,754<br>Chromosome 12: 113,422,849-113,423,944 |
| Naïve mouse B cell and mouse hybridoma | Final: IgG1 | 5': GGAAAGTGCAAGCTGCTCTG<br>3': GAGAGTCGGGGACATGGGAA | AGG<br>GGG | 7<br>8 | Chromosome 12: 113,336,399-113,337,014<br>Chromosome 12: 113,330,525-113,331,521 |
| Naïve mouse B cell and mouse hybridoma | Final: IgG2a | 5': CAGGACAGCTGAGGCAGCAG<br>3': AGAGCCTCTCCAAATATCTG | AGG<br>AGG | 56<br>57 | Chromosome 12: 113,295,139-113,295,846<br>Chromosome 12: 113,288,933-113,289,737 |
| Naïve mouse B cell and mouse hybridoma | Final: IgG2b | 5': TGACCTGACCTAGAGACTGG<br>3': CAGATCAATTGTAGAAGACA | TGG<br>CGG | 58<br>59 | Chromosome 12: 113,313,645-113,314,389<br>Chromosome 12: 113,307,934-113,308,842 |
| Naïve mouse B cell and mouse hybridoma | Final: IgG3 | 5': AAGAGGGACTCTAGGCCTGC<br>3': GCTGAACTTCCTCCAGTGCC | TGG<br>TGG | 60<br>61 | Chromosome 12: 113,365,084-113,365,911<br>Chromosome 12: 113,361,260-113,362,225 |
| Naïve mouse B cell and mouse hybridoma | Final: IgE | 5': GAAGGGACAAACAGGTTACA<br>3': TAATCAGTTCCCCATGCTGC | GGG<br>AGG | 62<br>63 | Chromosome 12: 113,276,763-113,277,438<br>Chromosome 12: 113,273,249-113,274,228 |
| Naïve mouse B cell and mouse hybridoma | Final: IgA | 5': ATCATATAAATGAAGCTCAG<br>3': CAGCTATGTGATACTCGGGCT | TGG<br>AGG | 64<br>65 | Chromosome 12: 113,265,941-113,266,690<br>Chromosome 12: 113,260,200-113,261,047 |
| Mouse Hybridoma | Fab' | GATGCAACAAGTGGCCATGT | TGG | 9 | Chromosome 12: 113,329,742-113,329,834 |
| Mouse Hybridoma | Fab' | CCTGCCTAAACCAACCAGGC | TGG | 66 | Chromosome 12: 113,329,835-113,330,211 |
| Mouse Hybridoma | F(ab')2 | TCCTAAGGTCACGTGTGTTG | TGG | 67 | Chromosome 12: 113,329,421-113,329,684 |
| Naïve human B cell | Start: IgM | 5': ATATTCCACCCAGGTAGTGG<br>3': ACAGGCGGACGCAAGTAGTG | AGG<br>AGG | 11<br>12 | Chromosome 14: 105,860,453-105,861,302<br>Chromosome 14: 105,860,453-105,861,302 |

TABLE 4-continued

| Starting type of mammalian cell | Start or Final IgH subclass | Example gRNA guide sequences to use in regions 5'- or 3'- end of the corresponding Ig switch | | PAM sequence | SEQ ID NO: | Genomic coordinates of the regions 5'- or 3'- end of the corresponding Ig switch for gRNA guide sequences design |
|---|---|---|---|---|---|---|
| Naïve human B cell | Final: IgG1 | 5': | AGCAGAGGATTCTTAGTCCT | TGG | 68 | Chromosome 14: 105,792,405-105,793,399 |
| | | 3': | TCGCCGACAGTTAAGAACCC | AGG | 14 | Chromosome 14: 105,743,090-105,743,554 |
| Naïve human B cell | Final: IgG2 | 5': | GGAGAGGCAAGATGCCAAAG | AGG | 69 | Chromosome 14: 105,764,900-105,765,392 |
| | | 3': | GCAGATAGACAAGAACCGAG | GGG | 70 | Chromosome 14: 105,644,790-105,645,355 |
| Naïve human B cell | Final: IgG3 | 5': | TTCTTGCCTCCTAGCAAAAC | AGG | 71 | Chromosome 14: 105,783,525-105,784,652 |
| | | 3': | TCGTGGATAGACAAGAACCG | AGG | 13 | Chromosome 14: 105,771,422-105,771,999 |
| Naïve human B cell | Final: IgG4 | 5': | CCGGTTCCAGTGCATGACCC | AGG | 72 | Chromosome 14: 105,633,525-105,634,594 |
| | | 3': | CCCAGACACTGGACCCTGCA | TGG | 73 | Chromosome 14: 105,626,081-105,626,807 |
| Naïve human B cell | Final: IgE | 5': | ATCCCTCACTTCTTGCTCTG | TGG | 74 | Chromosome 14: 105,614,205-105,615,103 |
| | | 3': | GCCTGATGGGCGCTGGCCTG | AGG | 75 | Chromosome 14: 105,601,738-105,602,245 |
| Naïve human B cell | Final: IgA1 | 5': | CAGCTCAGCGCTGTCATACC | TGG | 76 | Chromosome 14: 105,717,285-105,718,584 |
| | | 3': | GCTGGGTTCCTCCAGTATAG | AGG | 15 | Chromosome 14: 105,708,692-105,709,196 |
| Naïve human B cell | Final: IgA2 | 5': | GAGGTGTGAGGGCCCAGGC | GGG | 77 | Chromosome 14: 105,598,125-105,598,694 |
| | | 3': | CTCCAGTGTAGAGGAGGAGGC | AGG | 78 | Chromosome 14: 105,588,407-105,589,022 |

TABLE 5

The guide sequences of guide RNA (gRNA) identified in the 5'-end and the 3'-end of the different S regions for the mouse and human IgH locus (see Table 4 for the genome location of the S regions). These gRNA guide sequences are contiguous with a PAM having the NGG motif. The last three nucleotides of the gRNA guide sequences are the PAM sequences, shown is in bold here.

Naïve mouse B cell and mouse hybridoma: IgM 5'

1. GCCAGAGGCAGCCACAGCTG TGG (SEQ ID NO: 5)
2. CACCGCAAATGGTAAGCCAG AGG (SEQ ID NO: 79)
3. TGCCTCTGGCTTACCATTTG CGG (SEQ ID NO: 80)
4. GTAAACTGTTTCTGCTTAAG AGG (SEQ ID NO: 81)
5. TAAACTGTTTCTGCTTAAGA GGG (SEQ ID NO: 82)
6. GCCACAGCTGTGGCTGCCTC TGG (SEQ ID NO: 83)
7. AAGAGCAGCAGCCACAGCTG TGG (SEQ ID NO: 84)

Naïve mouse B cell and mouse hybridoma: IgM 3'

1. GTCACGTTCCTGTGGCTAGA AGG (SEQ ID NO: 6)
2. GGGCATGAACACCCGTTCTC AGG (SEQ ID NO: 85)
3. GGCATGAACACCCGTTCTCA GGG (SEQ ID NO: 86)
4. GCCTCTAGAGTAGGTGGATC TGG (SEQ ID NO: 87)
5. GGTGTTCATGCCCCTAGAGT TGG (SEQ ID NO: 88)
6. TAGCCACAGGAACGTGACTT TGG (SEQ ID NO: 89)
7. GGCCCTTCAGCCAACTCTAG GGG (SEQ ID NO: 90)
8. AGAGATGCCTCTAGAGTAGG TGG (SEQ ID NO: 91)
9. GGGAGAGATGCCTCTAGAGT AGG (SEQ ID NO: 92)
10. GAACACCCGTTCTCAGGGAG AGG (SEQ ID NO: 93)
11. TGGCCCTTCAGCCAACTCTA GGG (SEQ ID NO: 94)
12. CTTTGGAAGCCTTCACAGAC AGG (SEQ ID NO: 95)
13. CTAGGCCTCTCCCTGAGAAC GGG (SEQ ID NO: 96)
14. CTGGCCCTTCAGCCAACTCT AGG (SEQ ID NO: 97)
15. TTTGGAAGCCTTCACAGACA GGG (SEQ ID NO: 98)
16. ATGCCCCTAGAGTTGGCTGA AGG (SEQ ID NO: 99)

Naïve mouse B cell and mouse hybridoma: IgG1 5'

1. GGAAAGTGCAAGCTGCTCTG AGG (SEQ ID NO: 7)
2. GTCTTTCCCTCCTTCAATCC AGG (SEQ ID NO: 100)
3. GAAAGTGCAAGCTGCTCTGA GGG (SEQ ID NO: 101)
4. GTGCAAGCTGCTCTGAGGGG AGG (SEQ ID NO: 102)
5. TGCAAGCTGCTCTGAGGGGA GGG (SEQ ID NO: 103)
6. CAGAAGCAACCCTGGATTGA AGG (SEQ ID NO: 104)
7. TCTTTCCCTCCTTCAATCCA GGG (SEQ ID NO: 105)
8. TAAGGGAACAGAAGCAACCC TGG (SEQ ID NO: 106)
9. AGCAACCCTGGATTGAAGGA GGG (SEQ ID NO: 107)
10. AAGCAACCCTGGATTGAAGG AGG (SEQ ID NO: 108)
11. AAGGAGGGAAAGACAAGTAG AGG (SEQ ID NO: 109)
12. AAAGTGCAAGCTGCTCTGAG GGG (SEQ ID NO: 110)

Naïve mouse B cell and mouse hybridoma: IgG1 3'

1. GAGAGTCGGGGACATGGGAA GGG (SEQ ID NO: 8)
2. CTACTCCATGTAGAGAGTCG GGG (SEQ ID NO: 111)
3. CCCGACTCTCTACATGGAGT AGG (SEQ ID NO: 112)
4. CATGTAGAGAGTCGGGGACA TGG (SEQ ID NO: 113)
5. CCTACTCCATGTAGAGAGTC GGG (SEQ ID NO: 114)
6. ATGTAGAGAGTCGGGGACAT GGG (SEQ ID NO: 115)
7. GTAGGTGATATCCAACATTT GGG (SEQ ID NO: 116)
8. CATGTCCCCGACTCTCTACA TGG (SEQ ID NO: 117)
9. ACCAGACCAGATGAGACCTG AGG (SEQ ID NO: 118)
10. CTGGTGATCCTGACATTGAC AGG (SEQ ID NO: 119)
11. AGTAGGTGATATCCAACATT TGG (SEQ ID NO: 120)
12. CAATGGCCTCAGGTCTCATC TGG (SEQ ID NO: 121)
13. ACCTACTCCATGTAGAGAGT CGG (SEQ ID NO: 122)
14. GCCTCAGGTCTCATCTGGTC TGG (SEQ ID NO: 123)

Naïve mouse B cell and mouse hybridoma: IgG2a 5'

1. CAGGACAGCTGAGGCAGCAG AGG (SEQ ID NO: 56)
2. AAGGGTAAGGAGAGGCCTAC AGG (SEQ ID NO: 124)
3. CTCCTTACCCTTTCTACACT GGG (SEQ ID NO: 125)
4. GCCTACAGGATTGAGAGAAT AGG (SEQ ID NO: 126)
5. CTCTGCTGCCTCAGCTGTCC TGG (SEQ ID NO: 127)
6. AGTGTAGAAAGGGTAAGGAG AGG (SEQ ID NO: 128)
7. GAATAGGTAAAGAGGGAATG GGG (SEQ ID NO: 129)
8. AGAATAGGTAAAGAGGGAAT GGG (SEQ ID NO: 130)
9. GAGAATAGGTAAAGAGGGAA TGG (SEQ ID NO: 131)
10. TCTGCTGCCTCAGCTGTCCT GGG (SEQ ID NO: 132)
11. AAGAAACCCAGTGTAGAAAG GGG (SEQ ID NO: 133)
12. ATTGAGAGAATAGGTAAAGA GGG (SEQ ID NO: 134)
13. AGGTAAAGAGGGAATGGGGA AGG (SEQ ID NO: 135)
14. TCTCCTTACCCTTTCTACAC TGG (SEQ ID NO: 136)
15. GATTGAGAGAATAGGTAAAG AGG (SEQ ID NO: 137)

TABLE 5-continued

The guide sequences of guide RNA (gRNA) identified in the 5'-end and the 3'-end of the different S regions for the mouse and human IgH locus (see Table 4 for the genome location of the S regions). These gRNA guide sequences are contiguous with a PAM having the NGG motif. The last three nucleotides of the gRNA guide sequences are the PAM sequences, shown is in bold here.

Naïve mouse B cell and mouse hybridoma: IgG2a 3'

1. AGAGCCTCTCCAAATATCTG AGG (SEQ ID NO: 57)
2. GATCAGGATACACCATCAAG AGG (SEQ ID NO: 138)
3. TCAGATATTTGGAGAGGCTC TGG (SEQ ID NO: 139)
4. AAGCACCTTCCTCCTCTTGA TGG (SEQ ID NO: 140)
5. TTCTTCAATTGCTTTGAGAC AGG (SEQ ID NO: 141)
6. ATTCATGGAAAATTAAGATC AGG (SEQ ID NO: 142)
7. TCAATTGCTTTGAGACAGGC AGG (SEQ ID NO: 143)
8. CAATTGCTTTGAGACAGGCA GGG (SEQ ID NO: 144)
9. CAGGATACACCATCAAGAGG AGG (SEQ ID NO: 145)
10. ATACACCATCAAGAGGAGGA AGG (SEQ ID NO: 146)

Naïve mouse B cell and mouse hybridoma: IgG2b 5'

1. TGACCTGACCTAGAGACTGG TGG (SEQ ID NO: 58)
2. GGTCCACCAGTCTCTAGGTC AGG (SEQ ID NO: 147)
3. ACCCGCTCTCTCAATCTTGT AGG (SEQ ID NO: 148)
4. ACCTAGAGACTGGTGGACCC AGG (SEQ ID NO: 149)
5. GATTGAGAGAGCGGGTAAAG AGG (SEQ ID NO: 150)
6. GGCCTACAAGATTGAGAGAG CGG (SEQ ID NO: 151)
7. CTACCCTACCCTTTCTACAC TGG (SEQ ID NO: 152)
8. GCCTACAAGATTGAGAGAGC GGG (SEQ ID NO: 153)
9. ATTGAGAGAGCGGGTAAAGA GGG (SEQ ID NO: 154)
10. TCCTGGGTCCACCAGTCTCT AGG (SEQ ID NO: 155)
11. AAATCCAGTGTAGAAAGGGT AGG (SEQ ID NO: 156)
12. GTGTGAAAGGGTAGGGTAG AGG (SEQ ID NO: 157)

Naïve mouse B cell and mouse hybridoma: IgG2b 3'

1. CAGATCAATTGTAGAAGACA CGG (SEQ ID NO: 59)
2. TGTCTTCTACAATTGATCTG AGG (SEQ ID NO: 158)
3. TAAGGTCACAGTGCAAGCTC TGG (SEQ ID NO: 159)
4. CACATCGAAAATAAAAAACA TGG (SEQ ID NO: 160)
5. TAAAAACATGGAAAAATTA AGG (SEQ ID NO: 161)
6. GGTCACAGTGCAAGCTCTGG AGG (SEQ ID NO: 162)
7. CACAGTGCAAGCTCTGGAGG TGG (SEQ ID NO: 163)

Naïve mouse B cell and mouse hybridoma: IgG3 5'

1. AAGAGGGACTCTAGGCCTGC TGG (SEQ ID NO: 60)
2. AGTGTGGAACTCTAAGGTTT AGG (SEQ ID NO: 164)
3. GCCAAGAGTGTGGAACTCTA AGG (SEQ ID NO: 165)
4. ATACTTCTTCCTGCCCGTCT TGG (SEQ ID NO: 166)
5. AGAGGGACTCTAGGCCTGCT GGG (SEQ ID NO: 167)
6. ACCTTAGAGTTCCACACTCT TGG (SEQ ID NO: 168)
7. ACACTCTTGGCTTCCCCAGC AGG (SEQ ID NO: 169)
8. GAGGGACTCTAGGCCTGCTG GGG (SEQ ID NO: 170)
9. TGCTGGGGAAGCCAAGAGTG TGG (SEQ ID NO: 171)
10. AGTGCTGAAGAGACAAGATG AGG (SEQ ID NO: 172)

Naïve mouse B cell and mouse hybridoma: IgG3 3'

1. GCTGAACTCCTCCAGGTGCC TGG (SEQ ID NO: 61)
2. TAGGATATATCACCTAGGTC AGG (SEQ ID NO: 173)
3. GCATCATATAGCAACCTTGA TGG (SEQ ID NO: 174)
4. AGGATATATCACCTAGGTCA GGG (SEQ ID NO: 175)
5. CTTGGTCCTACAAGGATGCC AGG (SEQ ID NO: 176)
6. GCATGTAGGATATATCACCT AGG (SEQ ID NO: 177)
7. TTGGTCCTACAAGGATGCCA GGG (SEQ ID NO: 178)
8. AGTTCAGCCTTGGTCCTACA AGG (SEQ ID NO: 179)
9. GGGTTCTGCAAAGAGCATGT AGG (SEQ ID NO: 180)
10. CACCTGGAGGAGTTCAGCCT TGG (SEQ ID NO: 181)
11. TGAGGCAATTGGAACCATCA AGG (SEQ ID NO: 182)
12. GCTATATGATGCCCTGACCT AGG (SEQ ID NO: 183)

Naïve mouse B cell and mouse hybridoma: IgE 5'

1. GAAGGGACAAACAGGTTACA GGG (SEQ ID NO: 62)
2. GATAGCTGAAGGACATTCGG TGG (SEQ ID NO: 184)
3. AGGTGTCCCCTTCCCCACCC AGG (SEQ ID NO: 185)
4. TCCACATTAGAAGGCAGCCC AGG (SEQ ID NO: 186)
5. TGCAGGGAAGTGATAGCTGA AGG (SEQ ID NO: 187)
6. AGTGATAGCTGAAGGACATT AGG (SEQ ID NO: 188)
7. ACAAACAGGTTACAGGGTCC TCC (SEQ ID NO: 189)
8. AGAAGGGACAAACAGGTTAC AGG (SEQ ID NO: 190)
9. AAGAGACTGTCCACATTAGA AGG (SEQ ID NO: 191)
10. CAAACAGGTTACAGGGTCCT GGG (SEQ ID NO: 192)

Naïve mouse B cell and mouse hybridoma: IgE 3'

1. TAATCAGTTCCCCATGCTGC AGG (SEQ ID NO: 63)
2. CAGCATCCCCAACTGATTAA GGG (SEQ ID NO: 193)
3. TGGGGACCCCATTCCAGTCT AGG (SEQ ID NO: 194)

TABLE 5-continued

The guide sequences of guide RNA (gRNA) identified in the 5'-end and the 3'-end of the different S regions for the mouse and human IgH locus (see Table 4 for the genome location of the S regions). These gRNA guide sequences are contiguous with a PAM having the NGG motif. The last three nucleotides of the gRNA guide sequences are the PAM sequences, shown is in bold here.

4. GCAGCATGGGGAACTGATTA AGG (SEQ ID NO: 195)
5. TAACCATCTGTCTCCTAGAC TGG (SEQ ID NO: 196)
6. CAGATGGTTAGATTCCTTCT GGG (SEQ ID NO: 197)
7. TGATTAAGGGCAGCTGTGAC AGG (SEQ ID NO: 198)
8. ACAGATGGTTAGATTCCTTC TGG (SEQ ID NO: 199)
9. ATTCCAGTCTAGGAGACAGA TGG (SEQ ID NO: 200)
10. AGGGCAGCTGTGACAGGAGC AGG (SEQ ID NO: 201)
11. GGGCAGCTGTGACAGGAGCA GGG (SEQ ID NO: 202)
12. CTGTGACAGGAGCAGGGCTC TGG (SEQ ID NO: 203)

Naïve mouse B cell and mouse hybridoma: IgA 5'

1. ATCATATAAATGAAGCTCAG TGG (SEQ ID NO: 64)
2. AGGGCCCCTCAAAAACTGTC AGG (SEQ ID NO: 204)
3. GGGCCCCTCAAAAACTGTCA GGG (SEQ ID NO: 205)
4. GCCTACAAAGAGGGACATTG TGG (SEQ ID NO: 206)
5. CCCACAATGTCCCTCTTTGT AGG (SEQ ID NO: 207)
6. CCTACAAAGAGGGACATTGT GGG (SEQ ID NO: 208)
7. CCCTCAAAAACTGTCAGGGT AGG (SEQ ID NO: 209)
8. CTACAAAGAGGGACATTGTG GGG (SEQ ID NO: 210)
9. GGCAGAGGCAGCCTACAAAG AGG (SEQ ID NO: 211)
10. CAAGAGGGACATTGTGGGG AGG (SEQ ID NO: 212)
11. GCAGAGGCAGCCTACAAAGA GGG (SEQ ID NO: 213)
12. ATCATATAAATGAAGCTCAG TGG (SEQ ID NO: 64)

Naïve mouse B cell and mouse hybridoma: IgA 3'

1. CAGCTATGTGATACTGGGCT AGG (SEQ ID NO: 65)
2. TGTTGGTCAGCTCCGACTGC GGG (SEQ ID NO: 214)
3. CTGCATTGTGTACCCGCAGT CGG (SEQ ID NO: 215)
4. TCGGAGCTGACCAACAGTTC TGG (SEQ ID NO: 216)
5. CTGTTGGTCAGCTCCGACTG CGG (SEQ ID NO: 217)
6. GTCTATACAGCCAGAACTGT TGG (SEQ ID NO: 218)
7. TGCAGCAGCTATGTGATACT GGG (SEQ ID NO: 219)
8. ATGCAGCAGCTATGTGATAC TGG (SEQ ID NO: 220)
9. TGCCTTTCTCTTCTTTATAC AGG (SEQ ID NO: 221)
10. CTCCTGTATAAGAAGAGAAA AGG (SEQ ID NO: 222)
11. GTATAAAGAAGAGAAAGGCA TGG (SEQ ID NO: 223)

TABLE 5-continued

The guide sequences of guide RNA (gRNA) identified in the 5'-end and the 3'-end of the different S regions for the mouse and human IgH locus (see Table 4 for the genome location of the S regions). These gRNA guide sequences are contiguous with a PAM having the NGG motif. The last three nucleotides of the gRNA guide sequences are the PAM sequences, shown is in bold here.

Mouse hybridoma: Fab'

1. GATGCAACAAGTGGCCATGT TGG (SEQ ID NO: 9)
2. ACATGGCCACTTGTTGCATC TGG (SEQ ID NO: 224)
3. GGTGGAAATAGGTCAATACC TGG (SEQ ID NO: 225)
4. GTGGAAATAGGTCAATACCT GGG (SEQ ID NO: 226)
5. ATGGCCACTTGTTGCATCTG GGG (SEQ ID NO: 227)
6. CACTTGTTGCATCTGGGGTC AGG (SEQ ID NO: 228)
7. ACTTGTTGCATCTGGGGTCA GGG (SEQ ID NO: 229)
8. ACCTGGGGCACCCTCCAACA TGG (SEQ ID NO: 230)
9. ATATGTACAGGTAAGTCAGT AGG (SEQ ID NO: 231)
10. GACTTACCTGTACATATGCA AGG (SEQ ID NO: 232)
11. GCAACAAGTGGCCATGTTGG AGG (SEQ ID NO: 233)

Mouse hybridoma: Fab

1. CCTGCCTAAACCAACCAGGC TGG (SEQ ID NO: 66)
2. TTAGCCTGCCTAAACCAACC AGG (SEQ ID NO: 234)
3. CCAGCCTGGTTGGTTAGGC AGG (SEQ ID NO: 235)
4. CATTGGTTAATATCCTGGGT TGG (SEQ ID NO: 236)
5. ACACTCATTGGTTAATATCC TGG (SEQ ID NO: 237)
6. TCTATGTCCTTTACACTCAT TGG (SEQ ID NO: 238)
7. CTGTCCAGCCTGGTTGGTTT AGG (SEQ ID NO: 239)
8. TGATGGCTGTCCAGCCTGGT TGG (SEQ ID NO: 240)
9. ATATTAACCAATGAGTGTAA AGG (SEQ ID NO: 241)
10. CTGGGCTGAGATCCATTTCC TGG (SEQ ID NO: 242)
11. CCGGTGATGGCTGTCCAGCC TGG (SEQ ID NO: 243)
12. CAGGCTGGACAGCCATCACC AGG (SEQ ID NO: 244)

Mouse hybridoma: F(ab')2

1. TCCTAAGGTCACGTGTGTTG TGG (SEQ ID NO: 67)
2. CATCAGCAAGGATGATCCCG AGG (SEQ ID NO: 245)
3. CATCTACAAACCAGCTGAAC TGG (SEQ ID NO: 246)
4. AACCAGCTGAACTGGACCTC GGG (SEQ ID NO: 247)
5. CACAGCTCAGACGCAACCCC GGG (SEQ ID NO: 248)
6. ACACAGCTCAGACGCAACCC CGG (SEQ ID NO: 249)
7. CAGCTGGTTTGTAGATGATG TGG (SEQ ID NO: 250)
8. AGCTCAGACGCAACCCCGGG AGG (SEQ ID NO: 251)
9. ACCACAACACACGTGACCTT AGG (SEQ ID NO: 252)

TABLE 5-continued

The guide sequences of guide RNA (gRNA) identified in the 5'-end and the 3'-end of the different S regions for the mouse and human IgH locus (see Table 4 for the genome location of the S regions). These gRNA guide sequences are contiguous with a PAM having the NGG motif. The last three nucleotides of the gRNA guide sequences are the PAM sequences, shown is in bold here.

10. AAACCAGCTGAACTGGACCT CGG (SEQ ID NO: 253)

11. TGTTGTGGTAGACATCAGCA AGG (SEQ ID NO: 254)

12. ATCCCGAGGTCCAGTTCAGC TGG (SEQ ID NO: 255)

13. CTGGTTTGTAGATGATGTGG AGG (SEQ ID NO: 256)

Naïve human B cell: IgM 5'

1. ATATTCCACCCAGGTAGTGG AGG (SEQ ID NO: 11)

2. ATTACCACCCTCCACTACCT GGG (SEQ ID NO: 257)

3. AGGTCCCCTTGCTCTAGAAG TGG (SEQ ID NO: 258)

4. CATTACCACCCTCCACTACC TGG (SEQ ID NO: 259)

5. ACCACCCTCCACTACCTGGG TGG (SEQ ID NO: 260)

6. GAGAATGAGACCAAGAATTT AGG (SEQ ID NO: 261)

7. GTCTGTGATAAAAATGAGC AGG (SEQ ID NO: 262)

8. CCCCAGCGCCACCTGGGTTT TGG (SEQ ID NO: 263)

9. GTCCTGCCCCAGCGCCACCT GGG (SEQ ID NO: 264)

10. AGTCCTGCCCCAGCGCCACC TGG (SEQ ID NO: 265)

11. GCTCATTTTTATCACAGCAC AGG (SEQ ID NO: 266)

12. AGCACAGGCTCCTAAATTCT TGG (SEQ ID NO: 267)

Naïve human B cell: IgM 3'

1. ACAGCGGGACGCAAGTAGTG AGG (SEQ ID NO: 12)

2. CCAGACTGTCATGGCTATCA GGG (SEQ ID NO: 268)

3. ACTGTCATGGCTATCAGGGG TGG (SEQ ID NO: 269)

4. CATGGCTATCAGGGGTGGCG GGG (SEQ ID NO: 270)

5. CAGACTGTCATGGCTATCAG GGG (SEQ ID NO: 271)

6. GGTCTTTGTCCAAGGCTGCT GGG (SEQ ID NO: 272)

7. GTCTTTGTCCAAGGCTGCTG GGG (SEQ ID NO: 273)

8. AGGTCTTTGTCCAAGGCTGC TGG (SEQ ID NO: 274)

9. GTCATGGCTATCAGGGGTGG CGG (SEQ ID NO: 275)

10. CGGGGCCGTGGTGAGGCCTC AGG (SEQ ID NO: 276)

11. TCATGGCTATCAGGGGTGGC GGG (SEQ ID NO: 277)

12. AGGCCTCAGGTCTTTGTCCA AGG (SEQ ID NO: 278)

Naïve human B cell: IgG1 5'

1. AGCAGAGGATTCTTAGTCCT TGG (SEQ ID NO: 68)

2. TCTGCTACTCTTCACTCTGC CGG (SEQ ID NO: 279)

3. GTGGGCAGGGATTTTTTTCT TGG (SEQ ID NO: 280)

4. TGGTAGAAAGGGAGTGGGCA GGG (SEQ ID NO: 281)

5. TGCTTCTTTTTAATTGTCTT CGG (SEQ ID NO: 282)

6. AAATTATTCTTGTTTGAAAG TGG (SEQ ID NO: 283)

7. CTGGTAGAAAGGGAGTGGGC AGG (SEQ ID NO: 284)

8. TTTCCTGGTAGAAAGGGAGT GGG (SEQ ID NO: 285)

9. TAAAGAATCCTCTGCTTTTCC TGG (SEQ ID NO: 286)

10. CTGCCCACTCCCTTTCTACC AGG (SEQ ID NO: 287)

Naïve human B cell: IgG1 3'

1. TCGCGGACAGTTAAGAACCC AGG (SEQ ID NO: 14)

2. CACCCCCTGCCCCAAAGCCA AGG (SEQ ID NO: 288)

3. ACGGGCTTGGGTGTGCGCC TGG (SEQ ID NO: 289)

4. CCTGCCCCAAAGCCAAGGTC AGG (SEQ ID NO: 290)

5. GCATTGGGTGTGCGCCTGGC TGG (SEQ ID NO: 291)

6. GCCGGGCCTGACCTTGGCTT TGG (SEQ ID NO: 292)

7. CTGACCTTGGCTTTGGGGCA GGG (SEQ ID NO: 293)

8. GTGGGCTAAGGTGACGCAGG TGG (SEQ ID NO: 294)

Naïve human B cell: IgG2 5'

1. GGAGAGGCAAGATGCCAAAG AGG (SEQ ID NO: 69)

2. TGGCATCTTGCCTCTCCACC TGG (SEQ ID NO: 295)

3. AAGAACACGGGCACCCTCTT TGG (SEQ ID NO: 296)

4. GCCCCGCTTTCGCAAGAACA CGG (SEQ ID NO: 297)

5. GGGCCTCTGTCCAGCACTCG TGG (SEQ ID NO: 298)

6. ATGGGGGCAGCAGAGCGTGG GGG (SEQ ID NO: 299)

7. ACAGTCACGGAACGGCGTGA TGG (SEQ ID NO: 300)

8. CGGATTCTGCGTGACAGTCA CGG (SEQ ID NO: 301)

9. GGAACAAGCAGCCACTCTGG GGG (SEQ ID NO: 302)

10. GGAGAGGCAAGATGCCAAAG AGG (SEQ ID NO: 69)

Naïve human B cell: IgG2 3'

1. GCAGATAGACAAGAACCGAG GGG (SEQ ID NO: 70)

2. ACGGGCATTGGGTGTGCACC TGG (SEQ ID NO: 303)

3. GCATTGGGTGTGCACCTGGC TGG (SEQ ID NO: 304)

4. CCTGCCCCAAAGCCAAAGTC AGG (SEQ ID NO: 305)

5. CCCAAAGCCAAAGTCAGGCC CGG (SEQ ID NO: 306)

6. GTGTCTGGGCTCACGGGCAT TGG (SEQ ID NO: 307)

7. CCAGGCAGGGTCCAGTGTCT GGG (SEQ ID NO: 308)

8. TCCAGGCAGGGTCCAGTGTC TGG (SEQ ID NO: 309)

9. CGGTTCTTGTCTATCTGCGA GGG (SEQ ID NO: 310)

TABLE 5-continued

The guide sequences of guide RNA (gRNA) identified in the 5'-end and the 3'-end of the different S regions for the mouse and human IgH locus (see Table 4 for the genome location of the S regions). These gRNA guide sequences are contiguous with a PAM having the NGG motif. The last three nucleotides of the gRNA guide sequences are the PAM sequences, shown is in bold here.

10. ACTTTGGCTTTGGGGCAGGG AGG (SEQ ID NO: 311)

11. GGAGGGGGCTAAGGTGACGC AGG (SEQ ID NO: 312)

Naïve human B cell: IgG3 5'

1. TTCTTGCCTCCTAGCAAAAC AGG (SEQ ID NO: 71)

2. GATGCCCATAGCTTGACTTG GGG (SEQ ID NO: 313)

3. TAGATGCCCATAGCTTGACT TGG (SEQ ID NO: 314)

4. AGATGCCCATAGCTTGACTT GGG (SEQ ID NO: 315)

5. CCACTTGGCTCTGTGGGGAA GGG (SEQ ID NO: 316)

6. TCCACTTGGCTCTGTGGGGA AGG (SEQ ID NO: 317)

7. CTGATCCACTTGGCTCTGTG GGG (SEQ ID NO: 318)

8. GCTGATCCACTTGGCTCTGT GGG (SEQ ID NO: 319)

9. CAAAGGGTCAGGGGGAGGAG TGG (SEQ ID NO: 320)

10. CTGCTTTAGCTTGGACTCAA AGG (SEQ ID NO: 321)

11. GGCAAGAAACTGCTTTAGCT TGG (SEQ ID NO: 322)

Naïve human B cell: IgG3 3'

1. TCGTGGATAGACAAGAACCG AGG (SEQ ID NO: 13)

2. CCCAAAGCCAAGGTCAGGCC CGG (SEQ ID NO: 323)

3. GCCCGCCCCAGAAAGCTTGC AGG (SEQ ID NO: 324)

4. CCTGCCCCAAAGCCAAGGTC AGG (SEQ ID NO: 290)

5. GCATTGGGTGTGCGCCTGGC TGG (SEQ ID NO: 291)

6. ACGGGCATTGGGTGTGCGCC TGG (SEQ ID NO: 325)

7. TGTCTGGGCTCACGGGCATT GGG (SEQ ID NO: 326)

8. GTGTCTGGGCTCACGGGCAT TGG (SEQ ID NO: 307)

9. GGTCCAGTGTCTGGGCTCAC GGG (SEQ ID NO: 327)

10. CCAGGCAGGGTCCAGTGTCT GGG (SEQ ID NO: 308)

11. TCCAGGCAGGGTCCAGTGTC TGG (SEQ ID NO: 309)

12. CGGTTCTTGTCTATCCACGA GGG (SEQ ID NO: 328)

Naïve human B cell: IgG4 3'

1. CCGGTTCCAGTGCATGACCC AGG (SEQ ID NO: 72)

2. TCCACCTCCTGTCAGATCAG TGG (SEQ ID NO: 329)

3. GGCCACAGAGCAGGAGGTGA GGG (SEQ ID NO: 330)

4. GGGCCACAGAGCAGGAGGTG AGG (SEQ ID NO: 331)

5. GAACTGGGCCACAGAGCAGG AGG (SEQ ID NO: 332)

6. TAGGAACTGGGCCACAGAGC AGG (SEQ ID NO: 333)

7. TTCATGGCCTGTTAGGAACT GGG (SEQ ID NO: 334)

8. GTTCATGGCCTGTTAGGAAC TGG (SEQ ID NO: 335)

9. CCTGGGTCATGCACTGGAAC CGG (SEQ ID NO: 336)

10. CCAATCCCTGGGTCATGCAC TGG (SEQ ID NO: 337)

11. ATCTGACAGGAGGTGGAGCT CGG (SEQ ID NO: 338)

12. TCTGACAGGAGGTGGAGCTC GGG (SEQ ID NO: 339)

Naïve human B cell: IgG4 3'

1. CCCAGACACTGGACCCTGCA TGG (SEQ ID NO: 73)

2. CCCTGCCCCCAGCCAAAGTC AGG (SEQ ID NO: 340)

3. CCCCCAGCCAAAGTCAGGCC CGG (SEQ ID NO: 341)

4. ACGGGCATTGGGTGTGCGCC TGG (SEQ ID NO: 325)

5. GCATTGGGTGTGCGCCTGGC TGG (SEQ ID NO: 291)

6. TGTCTGGGCTCACGGGCATT GGG (SEQ ID NO: 326)

7. GGTCCAGTGTCTGGGCTCAC GGG (SEQ ID NO: 327)

8. GGGTCCAGTGTCTGGGCTCA CGG (SEQ ID NO: 342)

9. CTATCTGCGATGGTCCATGC AGG (SEQ ID NO: 343)

10. CGGTTCTTGTCTATCTGCGA TGG (SEQ ID NO: 344)

11. AGGCCGGGCCTGACTTTGGC TGG (SEQ ID NO: 345)

Naïve human B cell: IgE 5'

1. ATCCCTCACCTCTTGCTCTG TGG (SEQ ID NO: 74)

2. TATTGCGAGCTGCACATTCC TGG (SEQ ID NO: 346)

3. TCCACCTCCCGTCAGATCAG TGG (SEQ ID NO: 347)

4. ATTGCGAGCTGCACATTCCT GGG (SEQ ID NO: 348)

5. TGGCAGCATTAGATTCTCAT AGG (SEQ ID NO: 349)

6. GGCCACAGAGCAAGAGGTGA GGG (SEQ ID NO: 350)

7. GGGCCACAGAGCAAGAGGTG AGG (SEQ ID NO: 351)

8. TTCATGGCCTGTTAGGAACT GGG (SEQ ID NO: 334)

9. GTTCATGGCCTGTTAGGAAC TGG (SEQ ID NO: 335)

10. GAACCGGTTCATGGCCTGTT AGG (SEQ ID NO: 352)

11. CCAACCCCTGGGTCATGCAC TGG (SEQ ID NO: 353)

Naïve human B cell: IgE 3'

1. GCCTGATGGGCGCTGGCCTG AGG (SEQ ID NO: 75)

2. GTTGCTCAGCCACTATCATC AGG (SEQ ID NO: 354)

3. TCAGCCACTATCATCAGGCT GGG (SEQ ID NO: 355)

4. CTCAGCCACTATCATCAGGC TGG (SEQ ID NO: 356)

5. ACTATCATCAGGCTGGGCTC AGG (SEQ ID NO: 357)

6. TCAGGAAGGGGGGTGCCTCC AGG (SEQ ID NO: 358)

TABLE 5-continued

The guide sequences of guide RNA (gRNA) identified in the 5'-end and the 3'-end of the different S regions for the mouse and human IgH locus (see Table 4 for the genome location of the S regions). These gRNA guide sequences are contiguous with a PAM having the NGG motif. The last three nucleotides of the gRNA guide sequences are the PAM sequences, shown is in bold here.

7. CCAGGCCCAGGGCGGCTCCC AGG (SEQ ID NO: 359)

8. CATCAGGCTGGGCTCAGGAA GGG (SEQ ID NO: 360)

9. TCAGGCTGGGCTCAGGAAGG GGG (SEQ ID NO: 361)

10. TCATCAGGCTGGGCTCAGGA AGG (SEQ ID NO: 362)

11. CAGGCCCAGGGCGGCTCCCA GGG (SEQ ID NO: 363)

Naïve human B cell: IgA1 5'

1. CAGCTCAGCGCTGTCATACC TGG (SEQ ID NO: 76)

2. GGTATGACAGCGCTGAGCTG GGG (SEQ ID NO: 364)

3. CGCTGAGCTGGGGAGTCTCT GGG (SEQ ID NO: 365)

4. GCGCTGAGCTGGGGAGTCTC TGG (SEQ ID NO: 366)

5. GATTGATGGGAACCACTGCT TGG (SEQ ID NO: 367)

6. GGTGCTGAGGGGTGATTGAT GGG (SEQ ID NO: 368)

7. GCTTGGGCACTTTGGCTCTC AGG (SEQ ID NO: 369)

8. GGGTGCTGAGGGGTGATTGA TGG (SEQ ID NO: 370)

9. GGGAGTCTCTGGGGTGCTGA GGG (SEQ ID NO: 371)

10. CAGGTATGACAGCGCTGAGC TGG (SEQ ID NO: 372)

Naïve human B cell: IgA1 3'

1. GCTGGGTTCCTCCAGTATAG AGG (SEQ ID NO: 15)

2. ATGTTCAGAAACCATGTTGC TGG (SEQ ID NO: 373)

3. GCTGTCTGATCCCAGCAACA TGG (SEQ ID NO: 374)

4. TCACACAGCTCCTGCACCAC AGG (SEQ ID NO: 375)

5. TCTGAACATGCTCCTTAGAT AGG (SEQ ID NO: 376)

6. TGTTCAGAAACCATGTTGCT GGG (SEQ ID NO: 377)

7. CTGCACCACAGGCCTGCAGT TGG (SEQ ID NO: 378)

8. GAGGCCTGGTGACAGCCCCA TGG (SEQ ID NO: 379)

9. TGGAGGAACCCAGCACAGAG AGG (SEQ ID NO: 380)

10. GAACCCAGCACAGAGAGGCC TGG (SEQ ID NO: 381)

11. CTGAACATGCTCCTTAGATA GGG (SEQ ID NO: 382)

Naïve human B cell: IgA2 5'

1. GAGGTGTGAGGGCCCGAGGC GGG (SEQ ID NO: 77)

2. AGCAGGTGCAGGTCCGGCCT CGG (SEQ ID NO: 383)

3. GCAGGTGCAGGTCCGGCCTC GGG (SEQ ID NO: 384)

4. GCCCAGAGCTGGGTGCAGGT GGG (SEQ ID NO: 385)

5. GCTGCTCCAGGCCCAGAGCT GGG (SEQ ID NO: 386)

6. ACACCTCTTTCTGCTGCTCC AGG (SEQ ID NO: 387)

7. GTCATCAGCAGGTGCAGGTC CGG (SEQ ID NO: 388)

8. CCCGGGTCATCAGCAGGTGC AGG (SEQ ID NO: 389)

9. AGCCCACCTGCAGGGAGCTC TGG (SEQ ID NO: 390)

10. GGGCCTGGAGCAGCAGAAAG AGG (SEQ ID NO: 391)

Naïve human B cell: IgA2 3'

1. CTCCAGTGTAGAGGAGAGGC AGG (SEQ ID NO: 78)

2. ATGTTCAGAAACTGTGTCGC TGG (SEQ ID NO: 392)

3. TTACACAGCTCCTGCACCAT GGG (SEQ ID NO: 393)

4. CTGCACCATGGGCCTGCGGT TGG (SEQ ID NO: 394)

5. CTGCCTCTCCTCTACACTGG AGG (SEQ ID NO: 395)

6. GTTACACAGCTCCTGCACCA TGG (SEQ ID NO: 396)

7. TACCTGCCTCTCCTCTACAC TGG (SEQ ID NO: 397)

8. GCTCCTGCACCATGGGCCTG CGG (SEQ ID NO: 398)

9. GAGGCCTGGTGACAGCCCCA AGG (SEQ ID NO: 399)

10. TGGAGGAACCCAGCACAGAG AGG (SEQ ID NO: 380)

11. GAACCCAGCACAGAGAGGCC TGG (SEQ ID NO: 381)

---

What is claimed is:

1. A composition for directing class switch recombination (CSR) of an immunoglobulin heavy (IgH) chain in a mammalian cell to a different IgH subclass, the composition comprising a vector comprising a nucleic acid encoding a Cas9 nuclease or nickase and nucleic acids encoding at least two guide RNAs (gRNA), wherein the at least two gRNA are selected from SEQ ID NOs 5-8, 11-15, 56-65, 68-223, and 257-399.

2. The composition of claim 1, wherein the Cas9 nuclease or nickase is a human codon-optimized *S. pyogenes* Cas9 (hSpCas9) nuclease, a human codon-optimized *S. aureus* Cas9 (hSaCas9) nuclease, a hSpCas9 nickase, a hSaCas9 nickase or a catalytically inactive Cas9 (dCas9)-FokI nuclease.

3. The composition of claim 1, wherein the gRNA sequence binds a target sequence that is within or flanks a switch (S) region which is upstream from a gene segment/nucleic acid sequence that encode a constant region of an antibody heavy chain.

4. The composition of claim 1, wherein the gRNA sequence binds a target sequence that flanks a gene segment/nucleic acid sequence that encode a constant region of an antibody heavy chain.

5. The composition of claim 4, wherein the constant region is an exon constant region gene segment in the IgH gene.

6. The composition of claim 5, wherein the exon constant region gene segment in the IgH gene is selected from the group consisting of μ, δ,γ, α, or γ.

7. The composition of claim 1, wherein the different IgH subclass is selected from the group consisting of IgA1, IgA2, IgM, IgE, IgD, IgG1, IgG2, and IgG3 and IgG4.

8. A method for directing class switch recombination (CSR) of the immunoglobulin heavy (IgH) chain in a mammalian cell to a different IgH subclass comprising contacting the mammalian cell with a vector comprising a nucleic acid encoding a Cas9 nuclease or nickase and nucleic acids encoding at least two guide RNAs (gRNA), or contacting with a composition comprising said vector, wherein the at least two gRNA is selected from SEQ ID NOs 5-8, 11-15, 56-65, 68-223, and 257-399.

9. The method of claim 8, wherein the Cas9 nuclease or nickase is a hSpCas9 nuclease, a hSaCas9 nuclease, a hSpCas9 nickase, a hSaCas9 nickase or a dCas9-FokI nuclease.

10. The method of claim 8, wherein the gRNA sequence binds a target sequence that is within or flanks a switch (S) region which is upstream from a gene segment/nucleic acid sequence that encode a constant region of an antibody heavy chain.

11. The method of claim 8, wherein gRNA sequence binds a target sequence that flanks a gene segment/nucleic acid sequence that encode a constant region of an antibody heavy chain.

12. The composition of claim 11, wherein the constant region is an exon constant region gene segment in the IgH gene.

13. The method of claim 12, wherein the exon constant region gene segment in the IgH gene is selected from the group consisting of μ, δ,γ, α,ε.

14. The method of claim 8, wherein the mammalian cell is a naïve B lymphocyte, an activated B lymphocyte, or a hybridoma.

15. The method of claim 8, wherein the different IgH subclass is selected from the group consisting of IgA1, IgA2, IgM, IgE, IgD, IgG1, IgG2, and IgG3 and IgG4.

16. The method of claim 8, wherein the vector expresses the Cas9 nuclease or nickase and the at least two gRNA in vivo in the mammalian cell.

* * * * *

SEQUENCE LISTING

<160> NUMBER OF SEQ ID NOS: 438

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
gatgcaacaa gtggccatgt          20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgtgctcttc ctatgcaaac                                               20

<210> SEQ ID NO 3
<211> LENGTH: 94
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
taagggatcc ggcgcaacaa acttctctct gctgaaacaa gccggagatg tcgaagagaa   60
tcctggaccg gtgagcaagg gcgaggagct gttc                               94

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
taagatcgat ggccgcttta cttgtacagc tcgtccatgc                         40

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gccagaggca gccacagctg tgg                                           23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtcacgttcc tgtggctaga agg                                           23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
ggaaagtgca agctgctctg agg                                               23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gagagtcggg gacatgggaa ggg                                               23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gatgcaacaa gtggccatgt tgg                                               23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tgtgctcttc ctatgcaaac tgg                                               23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
atattccacc caggtagtgg agg                                               23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
acagcgggac gcaagtagtg agg                                               23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tcgtggatag acaagaaccg agg                                               23
```

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tcgcggacag ttaagaaccc agg                                          23

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gctgggttcc tccagtatag agg                                          23

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
caccgccaga ggcagccaca gctg                                         24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aaaccagctg tggctgcctc tggc                                         24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
caccgtcacg ttcctgtggc taga                                         24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aaactctagc cacaggaacg tgac                                         24

```
<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
caccggaaag tgcaagctgc tctg                                              24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aaaccagagc agcttgcact ttcc                                              24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
caccgagagt cggggacatg ggaa                                              24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aaacttccca tgtccccgac tctc                                              24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
caccgatgca acaagtggcc atgt                                              24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaacacatgg ccacttgttg catc                                              24
```

```
<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
caccgtgtgc tcttcctatg caaac                                           25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
aaacgtttgc ataggaagag cacac                                           25

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
caccgatatt ccacccaggt agtgg                                           25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aaacccacta cctgggtgga atatc                                           25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
caccgacagc gggacgcaag tagtg                                           25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aaaccactac ttgcgtcccg ctgtc                                           25

<210> SEQ ID NO 32
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
caccgtcgtg gatagacaag aaccg                                         25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aaaccggttc ttgtctatcc acgac                                         25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
caccgtcgcg gacagttaag aaccc                                         25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
aaacgggttc ttaactgtcc gcgac                                         25

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
caccgctggg ttcctccagt atag                                          24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aaacctatac tggaggaacc cagc                                          24

<210> SEQ ID NO 38
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cttatttcgg ttgaacatgc                                               20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggacactcag tcagtcagtg                                               20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cctgggtccc tccttactga                                               20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cagactgtgt gctacagtgg                                               20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aggacctcgt tctatagagg                                               20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ggtattcatc tgaaccttca                                               20

<210> SEQ ID NO 44
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 44
gcctggtgtc aactaggcag                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggatgccctg gcactgctct                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cttacctgta gctactctgc                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggaaatgtca agagccaacg                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcctcacttc tagtgaaccc                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ctgtaggtca tcatcgcacc                                              20

<210> SEQ ID NO 50
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 50
ggtgcaactt agcccagctc                                               20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gagctgagtg tgtgcagcac                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ctgtgccctg catgacgtcc                                               20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cagtgtccac tggtcaagcc                                               20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cgttgcaggt gtaggtctgg                                               20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cgttgcagat gtaggtctgg                                               20

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 56
caggacagct gaggcagcag agg                                               23

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
agagcctctc caaatatctg agg                                               23

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tgacctgacc tagagactgg tgg                                               23

<210> SEQ ID NO 59
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cagatcaatt gtagaagaca cgg                                               23

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
aagagggact ctaggcctgc tgg                                               23

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gctgaactcc tccaggtgcc tgg                                               23

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 62
gaagggacaa acaggttaca ggg                                              23

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
taatcagttc cccatgctgc agg                                              23

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
atcatataaa tgaagctcag tgg                                              23

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cagctatgtg atactgggct agg                                              23

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cctgcctaaa ccaaccaggc tgg                                              23

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tcctaaggtc acgtgtgttg tgg                                              23

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 68
agcagaggat tcttagtcct tgg                                              23

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ggagaggcaa gatgccaaag agg                                              23

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gcagatagac aagaaccgag ggg                                              23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ttcttgcctc ctagcaaaac agg                                              23

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ccggttccag tgcatgaccc agg                                              23

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cccagacact ggaccctgca tgg                                              23

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
atccctcacc tcttgctctg tgg                                          23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gcctgatggg cgctggcctg agg                                          23

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cagctcagcg ctgtcatacc tgg                                          23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
gaggtgtgag ggcccgaggc ggg                                          23

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ctccagtgta gaggagaggc agg                                          23

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
caccgcaaat ggtaagccag agg                                          23

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tgcctctggc ttaccatttg cgg                                              23

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gtaaactgtt tctgcttaag agg                                              23

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
taaactgttt ctgcttaaga ggg                                              23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gccacagctg tggctgcctc tgg                                              23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
aagagcagca gccacagctg tgg                                              23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gggcatgaac acccgttctc agg                                              23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ggcatgaaca cccgttctca ggg                                              23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gcctctagag taggtggatc tgg                                           23

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
ggtgttcatg cccctagagt tgg                                           23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
tagccacagg aacgtgactt tgg                                           23

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ggcccttcag ccaactctag ggg                                           23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
agagatgcct ctagagtagg tgg                                           23

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gggagagatg cctctagagt agg                                           23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gaacacccgt tctcagggag agg                                           23

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tggcccttca gccaactcta ggg                                           23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ctttggaagc cttcacagac agg                                           23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ctaggcctct ccctgagaac ggg                                           23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ctggcccttc agccaactct agg                                           23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tttggaagcc ttcacagaca ggg                                           23

```
<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
atgcccctag agttggctga agg                                               23

<210> SEQ ID NO 100
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
gtctttccct ccttcaatcc agg                                               23

<210> SEQ ID NO 101
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gaaagtgcaa gctgctctga ggg                                               23

<210> SEQ ID NO 102
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gtgcaagctg ctctgagggg agg                                               23

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tgcaagctgc tctgagggga ggg                                               23

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
cagaagcaac cctggattga agg                                               23

<210> SEQ ID NO 105
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
tctttccctc cttcaatcca ggg                                             23

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
taagggaaca gaagcaaccc tgg                                             23

<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
agcaaccctg gattgaagga ggg                                             23

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
aagcaaccct ggattgaagg agg                                             23

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
aaggagggaa agacaagtag agg                                             23

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
aaagtgcaag ctgctctgag ggg                                             23

<210> SEQ ID NO 111
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ctactccatg tagagagtcg ggg                                              23

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
cccgactctc tacatggagt agg                                              23

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
catgtagaga gtcggggaca tgg                                              23

<210> SEQ ID NO 114
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
cctactccat gtagagagtc ggg                                              23

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
atgtagagag tcggggacat ggg                                              23

<210> SEQ ID NO 116
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gtaggtgata tccaacattt ggg                                              23

<210> SEQ ID NO 117
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 117
catgtccccg actctctaca tgg                                              23

<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
accagaccag atgagacctg agg                                              23

<210> SEQ ID NO 119
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ctggtgatcc tgacattgac agg                                              23

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
agtaggtgat atccaacatt tgg                                              23

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
caatggcctc aggtctcatc tgg                                              23

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
acctactcca tgtagagagt cgg                                              23

<210> SEQ ID NO 123
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 123
gcctcaggtc tcatctggtc tgg                                              23

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
aagggtaagg agaggcctac agg                                              23

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
ctccttaccc tttctacact ggg                                              23

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gcctacagga ttgagagaat agg                                              23

<210> SEQ ID NO 127
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
ctctgctgcc tcagctgtcc tgg                                              23

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
agtgtagaaa gggtaaggag agg                                              23

<210> SEQ ID NO 129
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 129
gaataggtaa agagggaatg ggg                                              23

<210> SEQ ID NO 130
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
agaataggta aagagggaat ggg                                              23

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gagaataggt aaagagggaa tgg                                              23

<210> SEQ ID NO 132
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tctgctgcct cagctgtcct ggg                                              23

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
aagaaaaccc agtgtagaaa ggg                                              23

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
attgagagaa taggtaaaga ggg                                              23

<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 135
aggtaaagag ggaatgggga agg                                            23

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
tctccttacc ctttctacac tgg                                            23

<210> SEQ ID NO 137
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gattgagaga ataggtaaag agg                                            23

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gatcaggata caccatcaag agg                                            23

<210> SEQ ID NO 139
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
tcagatattt ggagaggctc tgg                                            23

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
aagcaccttc ctcctcttga tgg                                            23

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ttcttcaatt gctttgagac agg                               23

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
attcatggaa aattaagatc agg                               23

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
tcaattgctt tgagacaggc agg                               23

<210> SEQ ID NO 144
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
caattgcttt gagacaggca ggg                               23

<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
caggatacac catcaagagg agg                               23

<210> SEQ ID NO 146
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
atacaccatc aagaggagga agg                               23

<210> SEQ ID NO 147
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ggtccaccag tctctaggtc agg                                           23

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
acccgctctc tcaatcttgt agg                                           23

<210> SEQ ID NO 149
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
acctagagac tggtggaccc agg                                           23

<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gattgagaga gcgggtaaag agg                                           23

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ggcctacaag attgagagag cgg                                           23

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ctaccctacc ctttctacac tgg                                           23

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gcctacaaga ttgagagagc ggg                                          23

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
attgagagag cgggtaaaga ggg                                          23

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tcctgggtcc accagtctct agg                                          23

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
aaatccagtg tagaaagggt agg                                          23

<210> SEQ ID NO 157
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gtgtgaaagg gtagggtaga gg                                           22

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tgtcttctac aattgatctg agg                                          23

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
taaggtcaca gtgcaagctc tgg                                           23

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
cacatcgaaa ataaaaaaca tgg                                           23

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
taaaaaacat ggaaaaatta agg                                           23

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
ggtcacagtg caagctctgg agg                                           23

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
cacagtgcaa gctctggagg tgg                                           23

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
agtgtggaac tctaaggttt agg                                           23

<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gccaagagtg tggaactcta agg                                           23

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
atacttcttc ctgcccgtct tgg                                              23

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
agagggactc taggcctgct ggg                                              23

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
accttagagt tccacactct tgg                                              23

<210> SEQ ID NO 169
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
acactcttgg cttccccagc agg                                              23

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gagggactct aggcctgctg ggg                                              23

<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
tgctggggaa gccaagagtg tgg                                              23

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
agtgctgaag agacaagatg agg                                              23

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
taggatatat cacctaggtc agg                                              23

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gcatcatata gcaaccttga tgg                                              23

<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
aggatatatc acctaggtca ggg                                              23

<210> SEQ ID NO 176
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
cttggtccta caaggatgcc agg                                              23

<210> SEQ ID NO 177
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
gcatgtagga tatatcacct agg                                              23

```
<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ttggtcctac aaggatgcca ggg                                              23

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
agttcagcct tggtcctaca agg                                              23

<210> SEQ ID NO 180
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
gggttctgca aagagcatgt agg                                              23

<210> SEQ ID NO 181
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
cacctggagg agttcagcct tgg                                              23

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tgaggcaatt ggaaccatca agg                                              23

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gctatatgat gccctgacct agg                                              23

<210> SEQ ID NO 184
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gatagctgaa ggacattcgg tgg                                             23

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
aggtgtcccc ttccccaccc agg                                             23

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
tccacattag aaggcagccc agg                                             23

<210> SEQ ID NO 187
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tgcagggaag tgatagctga agg                                             23

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
agtgatagct gaaggacatt agg                                             23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
acaaacaggt tacagggtcc tcc                                             23

<210> SEQ ID NO 190
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
agaagggaca aacaggttac agg                                            23

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
aagagactgt ccacattaga agg                                            23

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
caaacaggtt acagggtcct ggg                                            23

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
cagcatcccc aactgattaa ggg                                            23

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
tggggacccc attccagtct agg                                            23

<210> SEQ ID NO 195
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gcagcatggg gaactgatta agg                                            23

<210> SEQ ID NO 196
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 196
taaccatctg tctcctagac tgg                                           23

<210> SEQ ID NO 197
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
cagatggtta gattccttct ggg                                           23

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
tgattaaggg cagctgtgac agg                                           23

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
acagatggtt agattccttc tgg                                           23

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
attccagtct aggagacaga tgg                                           23

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
agggcagctg tgacaggagc agg                                           23

<210> SEQ ID NO 202
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 202
gggcagctgt gacaggagca ggg                                           23

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ctgtgacagg agcagggctc tgg                                           23

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
agggcccctc aaaaactgtc agg                                           23

<210> SEQ ID NO 205
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
gggcccctca aaaactgtca ggg                                           23

<210> SEQ ID NO 206
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
gcctacaaag agggacattg tgg                                           23

<210> SEQ ID NO 207
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
cccacaatgt ccctctttgt agg                                           23

<210> SEQ ID NO 208
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 208
cctacaaaga gggacattgt ggg                                             23

<210> SEQ ID NO 209
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ccctcaaaaa ctgtcagggt agg                                             23

<210> SEQ ID NO 210
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ctacaaagag ggacattgtg ggg                                             23

<210> SEQ ID NO 211
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ggcagaggca gcctacaaag agg                                             23

<210> SEQ ID NO 212
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
caagagggac attgtgggga gg                                              22

<210> SEQ ID NO 213
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
gcagaggcag cctacaaaga ggg                                             23

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic

```
      oligonucleotide

<400> SEQUENCE: 214
tgttggtcag ctccgactgc ggg                                              23

<210> SEQ ID NO 215
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
ctgcattgtg tacccgcagt cgg                                              23

<210> SEQ ID NO 216
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
tcggagctga ccaacagttc tgg                                              23

<210> SEQ ID NO 217
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
ctgttggtca gctccgactg cgg                                              23

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
gtctatacag ccagaactgt tgg                                              23

<210> SEQ ID NO 219
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
tgcagcagct atgtgatact ggg                                              23

<210> SEQ ID NO 220
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 220
atgcagcagc tatgtgatac tgg                                              23

<210> SEQ ID NO 221
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
tgcctttctc ttctttatac agg                                              23

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
ctcctgtata aagaagagaa agg                                              23

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
gtataaagaa gagaaaggca tgg                                              23

<210> SEQ ID NO 224
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
acatggccac ttgttgcatc tgg                                              23

<210> SEQ ID NO 225
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
ggtggaaata ggtcaatacc tgg                                              23

<210> SEQ ID NO 226
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
gtggaaatag gtcaataacct ggg                                              23

<210> SEQ ID NO 227
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
atggccactt gttgcatctg ggg                                               23

<210> SEQ ID NO 228
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
cacttgttgc atctggggtc agg                                               23

<210> SEQ ID NO 229
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
acttgttgca tctggggtca ggg                                               23

<210> SEQ ID NO 230
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
acctgggcca ccctccaaca tgg                                               23

<210> SEQ ID NO 231
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
atatgtacag gtaagtcagt agg                                               23

<210> SEQ ID NO 232
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
gacttacctg tacatatgca agg                                          23

<210> SEQ ID NO 233
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gcaacaagtg gccatgttgg agg                                          23

<210> SEQ ID NO 234
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ttagcctgcc taaaccaacc agg                                          23

<210> SEQ ID NO 235
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
ccagcctggt tggtttaggc agg                                          23

<210> SEQ ID NO 236
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
cattggttaa tatcctgggt tgg                                          23

<210> SEQ ID NO 237
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
acactcattg gttaatatcc tgg                                          23

<210> SEQ ID NO 238
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
tctatgtcct ttacactcat tgg                                           23

<210> SEQ ID NO 239
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
ctgtccagcc tggttggttt agg                                           23

<210> SEQ ID NO 240
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
tgatggctgt ccagcctggt tgg                                           23

<210> SEQ ID NO 241
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
atattaacca atgagtgtaa agg                                           23

<210> SEQ ID NO 242
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
ctgggctgag atccatttcc tgg                                           23

<210> SEQ ID NO 243
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
ccggtgatgg ctgtccagcc tgg                                           23

<210> SEQ ID NO 244
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
caggctggac agccatcacc agg                                           23

<210> SEQ ID NO 245
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
catcagcaag gatgatcccg agg                                              23

<210> SEQ ID NO 246
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
catctacaaa ccagctgaac tgg                                              23

<210> SEQ ID NO 247
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
aaccagctga actggacctc ggg                                              23

<210> SEQ ID NO 248
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
cacagctcag acgcaacccc ggg                                              23

<210> SEQ ID NO 249
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
acacagctca gacgcaaccc cgg                                              23

<210> SEQ ID NO 250
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
cagctggttt gtagatgatg tgg                                              23

```
<210> SEQ ID NO 251
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
agctcagacg caaccccggg agg                                               23

<210> SEQ ID NO 252
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
accacaacac acgtgacctt agg                                               23

<210> SEQ ID NO 253
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
aaaccagctg aactggacct cgg                                               23

<210> SEQ ID NO 254
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
tgttgtggta gacatcagca agg                                               23

<210> SEQ ID NO 255
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
atcccgaggt ccagttcagc tgg                                               23

<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
ctggtttgta gatgatgtgg agg                                               23
```

```
<210> SEQ ID NO 257
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
attaccaccc tccactacct ggg                                              23

<210> SEQ ID NO 258
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
aggtcccctt gctctagaag tgg                                              23

<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
cattaccacc ctccactacc tgg                                              23

<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
accaccctcc actacctggg tgg                                              23

<210> SEQ ID NO 261
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
gagaatgaga ccaagaattt agg                                              23

<210> SEQ ID NO 262
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
gtctgtgata aaaatgagca gg                                               22

<210> SEQ ID NO 263
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
ccccagcgcc acctgggttt tgg                                          23

<210> SEQ ID NO 264
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
gtcctgcccc agcgccacct ggg                                          23

<210> SEQ ID NO 265
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
agtcctgccc cagcgccacc tgg                                          23

<210> SEQ ID NO 266
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
gctcattttt atcacagcac agg                                          23

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
agcacaggct cctaaattct tgg                                          23

<210> SEQ ID NO 268
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ccagactgtc atggctatca ggg                                          23

<210> SEQ ID NO 269
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
actgtcatgg ctatcagggg tgg                                           23

<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
catggctatc aggggtggcg ggg                                           23

<210> SEQ ID NO 271
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
cagactgtca tggctatcag ggg                                           23

<210> SEQ ID NO 272
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ggtctttgtc caaggctgct ggg                                           23

<210> SEQ ID NO 273
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
gtctttgtcc aaggctgctg ggg                                           23

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
aggtctttgt ccaaggctgc tgg                                           23

<210> SEQ ID NO 275
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 275
gtcatggcta tcaggggtgg cgg                                           23

<210> SEQ ID NO 276
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
cggggccgtg gtgaggcctc agg                                           23

<210> SEQ ID NO 277
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
tcatggctat cagggtggc ggg                                            23

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
aggcctcagg tctttgtcca agg                                           23

<210> SEQ ID NO 279
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
tctgctactc ttcactctgc cgg                                           23

<210> SEQ ID NO 280
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
gtgggcaggg attttttctt tgg                                           23

<210> SEQ ID NO 281
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 281
tggtagaaag ggagtgggca ggg                                               23

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
tgcttctttt taattgtctt cgg                                               23

<210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
aaattattct tgtttgaaag tgg                                               23

<210> SEQ ID NO 284
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ctggtagaaa gggagtgggc agg                                               23

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
tttcctggta gaagggagt ggg                                                23

<210> SEQ ID NO 286
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
taaagaatcc tctgcttttc ctgg                                              24

<210> SEQ ID NO 287
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 287
ctgcccactc cctttctacc agg                                              23

<210> SEQ ID NO 288
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288 cacccctgc cccaaagcca agg                                               23

<210> SEQ ID NO 289
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
acgggcttgg gtgtgcgcct gg                                               22

<210> SEQ ID NO 290
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
cctgccccaa agccaaggtc agg                                              23

<210> SEQ ID NO 291
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
gcattgggtg tgcgcctggc tgg                                              23

<210> SEQ ID NO 292
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
gccgggcctg accttggctt tgg                                              23

<210> SEQ ID NO 293
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 293
ctgaccttgg ctttggggca ggg                                              23

<210> SEQ ID NO 294
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
gtgggctaag gtgacgcagg tgg                                              23

<210> SEQ ID NO 295
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
tggcatcttg cctctccacc tgg                                              23

<210> SEQ ID NO 296
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
aagaacacgg gcaccctctt tgg                                              23

<210> SEQ ID NO 297
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
gccccgcttt cgcaagaaca cgg                                              23

<210> SEQ ID NO 298
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
gggcctctgt ccagcactcg tgg                                              23

<210> SEQ ID NO 299
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 299
atgggggcag cagagcgtgg ggg                                             23

<210> SEQ ID NO 300
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
acagtcacgg aacggcgtga tgg                                             23

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
cggattctgc gtgacagtca cgg                                             23

<210> SEQ ID NO 302
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
ggaacaagca gccactctgg ggg                                             23

<210> SEQ ID NO 303
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
acgggcattg ggtgtgcacc tgg                                             23

<210> SEQ ID NO 304
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
gcattgggtg tgcacctggc tgg                                             23

<210> SEQ ID NO 305
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 305
cctgccccaa agccaaagtc agg                                              23

<210> SEQ ID NO 306
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
cccaaagcca aagtcaggcc cgg                                              23

<210> SEQ ID NO 307
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
gtgtctgggc tcacgggcat tgg                                              23

<210> SEQ ID NO 308
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
ccaggcaggg tccagtgtct ggg                                              23

<210> SEQ ID NO 309
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
tccaggcagg gtccagtgtc tgg                                              23

<210> SEQ ID NO 310
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
cggttcttgt ctatctgcga ggg                                              23

<210> SEQ ID NO 311
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
```
actttggctt tggggcaggg agg                                        23

<210> SEQ ID NO 312
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312 ggaggggget aaggtgacgc agg                                        23

<210> SEQ ID NO 313
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
gatgcccata gcttgacttg ggg                                        23

<210> SEQ ID NO 314
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
tagatgccca tagcttgact tgg                                        23

<210> SEQ ID NO 315
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
agatgcccat agcttgactt ggg                                        23

<210> SEQ ID NO 316
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
ccacttggct ctgtggggaa ggg                                        23

<210> SEQ ID NO 317
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317

```
tccacttggc tctgtgggga agg                                              23
```

<210> SEQ ID NO 318
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318

```
ctgatccact tggctctgtg ggg                                              23
```

<210> SEQ ID NO 319
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319

```
gctgatccac ttggctctgt ggg                                              23
```

<210> SEQ ID NO 320
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320

```
caaagggtca gggggaggag tgg                                              23
```

<210> SEQ ID NO 321
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321

```
ctgctttagc ttggactcaa agg                                              23
```

<210> SEQ ID NO 322
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322

```
ggcaagaaac tgctttagct tgg                                              23
```

<210> SEQ ID NO 323
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323

```
cccaaagcca aggtcaggcc cgg                                              23
```

<210> SEQ ID NO 324
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
gcccgcccca gaaagcttgc agg                                          23

<210> SEQ ID NO 325
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
acgggcattg ggtgtgcgcc tgg                                          23

<210> SEQ ID NO 326
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
tgtctgggct cacgggcatt ggg                                          23

<210> SEQ ID NO 327
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
ggtccagtgt ctgggctcac ggg                                          23

<210> SEQ ID NO 328
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
cggttcttgt ctatccacga ggg                                          23

<210> SEQ ID NO 329
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
tccacctcct gtcagatcag tgg                                          23

<210> SEQ ID NO 330
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
ggccacagag caggaggtga ggg                                             23

<210> SEQ ID NO 331
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
gggccacaga gcaggaggtg agg                                             23

<210> SEQ ID NO 332
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
gaactgggcc acagagcagg agg                                             23

<210> SEQ ID NO 333
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
taggaactgg gccacagagc agg                                             23

<210> SEQ ID NO 334
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
ttcatggcct gttaggaact ggg                                             23

<210> SEQ ID NO 335
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
gttcatggcc tgttaggaac tgg                                             23

```
<210> SEQ ID NO 336
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
cctgggtcat gcactggaac cgg                                             23

<210> SEQ ID NO 337
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
ccaatccctg ggtcatgcac tgg                                             23

<210> SEQ ID NO 338
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
atctgacagg aggtggagct cgg                                             23

<210> SEQ ID NO 339
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
tctgacagga ggtggagctc ggg                                             23

<210> SEQ ID NO 340
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
ccctgccccc agccaaagtc agg                                             23

<210> SEQ ID NO 341
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
cccccagcca aagtcaggcc cgg                                             23

<210> SEQ ID NO 342
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gggtccagtg tctgggctca cgg                                              23

<210> SEQ ID NO 343
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
ctatctgcga tggtccatgc agg                                              23

<210> SEQ ID NO 344
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
cggttcttgt ctatctgcga tgg                                              23

<210> SEQ ID NO 345
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
aggccgggcc tgactttggc tgg                                              23

<210> SEQ ID NO 346
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
tattgcgagc tgcacattcc tgg                                              23

<210> SEQ ID NO 347
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
tccacctccc gtcagatcag tgg                                              23

<210> SEQ ID NO 348
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
attgcgagct gcacattcct ggg                                              23

<210> SEQ ID NO 349
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
tggcagcatt agattctcat agg                                              23

<210> SEQ ID NO 350
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
ggccacagag caagaggtga ggg                                              23

<210> SEQ ID NO 351
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
gggccacaga gcaagaggtg agg                                              23

<210> SEQ ID NO 352
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
gaaccggttc atggcctgtt agg                                              23

<210> SEQ ID NO 353
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
ccaacccctg ggtcatgcac tgg                                              23

<210> SEQ ID NO 354
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 354
gttgctcagc cactatcatc agg                                             23

<210> SEQ ID NO 355
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
tcagccacta tcatcaggct ggg                                             23

<210> SEQ ID NO 356
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
ctcagccact atcatcaggc tgg                                             23

<210> SEQ ID NO 357
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
actatcatca ggctgggctc agg                                             23

<210> SEQ ID NO 358
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
tcaggaaggg gggtgcctcc agg                                             23

<210> SEQ ID NO 359
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
ccaggcccag ggcggctccc agg                                             23

<210> SEQ ID NO 360
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 360
catcaggctg ggctcaggaa ggg                                              23

<210> SEQ ID NO 361
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
tcaggctggg ctcaggaagg ggg                                              23

<210> SEQ ID NO 362
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
tcatcaggct gggctcagga agg                                              23

<210> SEQ ID NO 363
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
caggcccagg gcggctccca ggg                                              23

<210> SEQ ID NO 364
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
ggtatgacag cgctgagctg ggg                                              23

<210> SEQ ID NO 365
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
cgctgagctg gggagtctct ggg                                              23

<210> SEQ ID NO 366
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 366
gcgctgagct ggggagtctc tgg                                               23

<210> SEQ ID NO 367
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
gattgatggg aaccactgct tgg                                               23

<210> SEQ ID NO 368
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
ggtgctgagg ggtgattgat ggg                                               23

<210> SEQ ID NO 369
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
gcttgggcac tttggctctc agg                                               23

<210> SEQ ID NO 370
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
gggtgctgag gggtgattga tgg                                               23

<210> SEQ ID NO 371
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
gggagtctct ggggtgctga ggg                                               23

<210> SEQ ID NO 372
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 372
caggtatgac agcgctgagc tgg                                         23

<210> SEQ ID NO 373
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
atgttcagaa accatgttgc tgg                                         23

<210> SEQ ID NO 374
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gctgtctgat cccagcaaca tgg                                         23

<210> SEQ ID NO 375
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
tcacacagct cctgcaccac agg                                         23

<210> SEQ ID NO 376
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
tctgaacatg ctccttagat agg                                         23

<210> SEQ ID NO 377
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
tgttcagaaa ccatgttgct ggg                                         23

<210> SEQ ID NO 378
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
ctgcaccaca ggcctgcagt tgg                                          23

<210> SEQ ID NO 379
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
gaggcctggt gacagcccca tgg                                          23

<210> SEQ ID NO 380
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
tggaggaacc cagcacagag agg                                          23

<210> SEQ ID NO 381
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
gaacccagca cagagaggcc tgg                                          23

<210> SEQ ID NO 382
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
ctgaacatgc tccttagata ggg                                          23

<210> SEQ ID NO 383
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
agcaggtgca ggtccggcct cgg                                          23

<210> SEQ ID NO 384
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
gcaggtgcag gtccggcctc ggg                                           23

<210> SEQ ID NO 385
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
gcccagagct gggtgcaggt ggg                                           23

<210> SEQ ID NO 386
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
gctgctccag gcccagagct ggg                                           23

<210> SEQ ID NO 387
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
acacctcttt ctgctgctcc agg                                           23

<210> SEQ ID NO 388
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
gtcatcagca ggtgcaggtc cgg                                           23

<210> SEQ ID NO 389
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
cccgggtcat cagcaggtgc agg                                           23

<210> SEQ ID NO 390
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
agcccacctg cagggagctc tgg                                                23

<210> SEQ ID NO 391
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
gggcctggag cagcagaaag agg                                                23

<210> SEQ ID NO 392
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
atgttcagaa actgtgtcgc tgg                                                23

<210> SEQ ID NO 393
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
ttacacagct cctgcaccat ggg                                                23

<210> SEQ ID NO 394
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
ctgcaccatg ggcctgcggt tgg                                                23

<210> SEQ ID NO 395
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
ctgcctctcc tctacactgg agg                                                23

<210> SEQ ID NO 396
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396

```
gttacacagc tcctgcacca tgg                                          23

<210> SEQ ID NO 397
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
tacctgcctc tcctctacac tgg                                          23

<210> SEQ ID NO 398
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
gctcctgcac catgggcctg cgg                                          23

<210> SEQ ID NO 399
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
gaggcctggt gacagcccca agg                                          23

<210> SEQ ID NO 400
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
accgcaaatg gtaagccaga ggcagccaca ggaagggtgc aaaagagcgg cc          52

<210> SEQ ID NO 401
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
accgcaaatg gtaagccaga ggcagagggt gcaaaagagc ggcc                   44

<210> SEQ ID NO 402
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
accgcaaatg gtaagccaga gcggcc                                       26
```

<210> SEQ ID NO 403
<211> LENGTH: 30
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 403
accgcaaatg gtaagccaga ggcagcggcc                              30

<210> SEQ ID NO 404
<211> LENGTH: 35
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 404
accgcaaatg gtaagccaga ggcaaaagag cggcc                        35

<210> SEQ ID NO 405
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 405
accggaggtg caaaagagcg gcc                                     23

<210> SEQ ID NO 406
<211> LENGTH: 48
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 406
accgcaaatg gtaagccaga ggcagccaca aaaagcaaaa gagcggcc          48

<210> SEQ ID NO 407
<211> LENGTH: 52
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 407
accgcaaatg gtaagccaga ggcagccaca gggaagggtg caaaagagcg gc     52

<210> SEQ ID NO 408
<211> LENGTH: 45
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 408
tggggcagcc acagcgggac gcaagtaccc aggggcctct gcgcc             45

<210> SEQ ID NO 409
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 409
tggggcagcc acagcgggac gcaagtacag gggcctctgc gcc                    43

<210> SEQ ID NO 410
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 410
tggggcagcc acagcgggac gcaagtccca ggggcctctg cgcc                   44

<210> SEQ ID NO 411
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 411
tggggcagcc acagcgggac gcaagtaggg gcctctgcgc c                      41

<210> SEQ ID NO 412
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 412
tggggcagcc acagcgggac gcaagtcggg gcctctgcgc c                      41

<210> SEQ ID NO 413
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 413
tggggcagcc acagcgggac gcaacccagg ggcctctgcg cc                     42

<210> SEQ ID NO 414
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 414
tggggcagcc acagcgggac gcaacgcc                                     28

```
<210> SEQ ID NO 415
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
tggggcagcc acagcgggac gctgcgcc                                            28

<210> SEQ ID NO 416
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
tggggcagcc acagcgggac cccaggggcc tctgcgcc                                 38

<210> SEQ ID NO 417
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
tgggggggcc tctgcgcc                                                       18

<210> SEQ ID NO 418
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
gatgcaacaa gtggccatgt tggagg                                              26

<210> SEQ ID NO 419
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
cacagcggga cgcaagtata gaggagag                                            28

<210> SEQ ID NO 420
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
cacagcggga cgcaagttag aggagag                                             27

<210> SEQ ID NO 421
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
cacagcggga cgcaagtaga ggagag                                              26

<210> SEQ ID NO 422
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
cacagcggga cgcaagtaga g                                                   21

<210> SEQ ID NO 423
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
cacagcggga tagaggagag                                                     20

<210> SEQ ID NO 424
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
cacagcgggg agag                                                           14

<210> SEQ ID NO 425
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
cacatagagg agag                                                           14

<210> SEQ ID NO 426
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
cacagcggga cgcaagtaat agaggaga                                            28

<210> SEQ ID NO 427
<211> LENGTH: 28
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
cacagcggga cgcaagtaca gaggagag                                            28

<210> SEQ ID NO 428
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
cctgacccca gatgcaacaa gtggccatgt tggagggtgg cccaggtatt gac               53

<210> SEQ ID NO 429
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
cctgacccca gatgcaacaa gtggcccagg tattgac                                 37

<210> SEQ ID NO 430
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
cctgacccca gatgcaacaa gtggccaggg tggcccaggt attgac                       46

<210> SEQ ID NO 431
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
cctgacccca gatgcaacaa gtgtggccca ggtattgac                               39

<210> SEQ ID NO 432
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
caccctgacc ccagatgcaa caagtggcca aactggccct ggcacttcaa aacatggcac       60

<210> SEQ ID NO 433
<211> LENGTH: 51
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 433
caccctgacc ccagatgcaa caagtggccc tggcacttca aacatggca c                    51

<210> SEQ ID NO 434
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
caccctgacc ccagatgcaa ctggccctgg cacttcaaaa catggcac                       48

<210> SEQ ID NO 435
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
caccctgacc ccagatgcaa caactggccc tggcacttca aacatggca c                    51

<210> SEQ ID NO 436
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Pro Ala Ala Pro Arg Trp Thr Arg Lys Leu
1               5                   10

<210> SEQ ID NO 437
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Val Pro Arg Asp Cys Gly Cys Lys Pro Cys Ile Cys Thr
1               5                   10

<210> SEQ ID NO 438
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Val Pro Glu Val Ser Ser Val Phe Ile Phe
1               5                   10
```